United States Patent
Kumon et al.

(10) Patent No.: US 9,644,013 B2
(45) Date of Patent: May 9, 2017

(54) PARTIAL REGION POLYPEPTIDE OF REIC/DKK-3 PROTEIN

(71) Applicants: NATIONAL UNIVERSITY CORPORATION OKAYAMA UNIVERSITY, Okayama-shi, Okayama (JP); Momotaro-Gene Inc., Okayama-shi, Okayama (JP)

(72) Inventors: Hiromi Kumon, Okayama (JP); Masami Watanabe, Okayama (JP); Junichiro Futami, Okayama (JP); Yasuyuki Fujii, Okayama (JP); Hideo Ueki, Okayama (JP); Kazuhiko Ochiai, Tokyo (JP)

(73) Assignees: NATIONAL UNIVERSITY CORPORATION OKAYAMA UNIVERSITY, Okayama (JP); MOMOTARO-GENE INC., Okayama (JP)

( * ) Notice: Subject to any disclaimer, the term of this patent is extended or adjusted under 35 U.S.C. 154(b) by 0 days.

(21) Appl. No.: 14/997,186

(22) Filed: Jan. 15, 2016

(65) Prior Publication Data

US 2016/0176938 A1 Jun. 23, 2016

Related U.S. Application Data

(62) Division of application No. 13/807,747, filed as application No. PCT/JP2011/065644 on Jul. 1, 2011, now abandoned.

(30) Foreign Application Priority Data

Jul. 1, 2010 (JP) .................................. 2010-150935
Jan. 26, 2011 (JP) .................................. 2011-014319

(51) Int. Cl.
| | | |
|---|---|---|
| C07H 21/04 | (2006.01) | |
| C07K 14/47 | (2006.01) | |
| A61K 38/00 | (2006.01) | |
| A61K 48/00 | (2006.01) | |

(52) U.S. Cl.
CPC .......... C07K 14/4747 (2013.01); C07K 14/47 (2013.01); C07K 14/4703 (2013.01); A61K 38/00 (2013.01); A61K 48/00 (2013.01)

(58) Field of Classification Search
None
See application file for complete search history.

(56) References Cited

U.S. PATENT DOCUMENTS

| | | |
|---|---|---|
| 2002/0161178 A1 | 10/2002 | Bass et al. |
| 2003/0068312 A1 | 4/2003 | McCarthy |
| 2009/0005538 A1* | 1/2009 | Kumon .............. C07K 14/4747 530/350 |
| 2012/0034251 A1 | 2/2012 | Kumon et al. |
| 2013/0274199 A1 | 10/2013 | Kumon et al. |

FOREIGN PATENT DOCUMENTS

| | | |
|---|---|---|
| EP | 2090654 A1 | 8/2009 |
| WO | 00/52047 A2 | 9/2000 |
| WO | 00/52047 A3 | 9/2000 |
| WO | 2008/050898 A1 | 5/2008 |
| WO | 2009/119874 A1 | 10/2009 |

OTHER PUBLICATIONS

International Search Report dated Oct. 4, 2011, issued in Japanese Patent Application PCT/JP2011/065644.
Sen-Yung Hsieh et al., "Dickkopf-3/REIC functions as a suppressor gene of tumor growth," Oncogene, 2004, 23(57, pp. 9183-9189.
Valery E. Krupnik et al., "Functional and structural diversity of the human Dickkopf gene family," Gene, 1999, 238(2), pp. 301-313.
Supplemental European Search Report dated Nov. 20, 2013, issued in European Application No. 11801037.0.
Database Geneseq [on line], "Human dicckopf-3 protein, SEQ ID No. 6" XP002715922, Jun. 2, 2005 (retreived from EBI accession No. GSP:ADY86168, 1-page.
Masami Watanabe et al. "Immunological aspects of REIC/Dkk-3 in monocyte differentiation and tumor regression," International Journal of Oncology, vol. 34, No. 3, Mar. 1, 2009, pp. 657-663.
Office Action with an English Translation issued in China dated Jul. 22, 2014 Application No. 20118004601.1.
Abrazza et al. An N-terminal 78 amino acid truncation of REIC/Dkk-3 effectively induces apoptosis, Biochemical and Biophysical Research Communications, 375:614-618 (2008).
GenBank AAS86757.1, 2004.
Japanese Office Action dated Jul. 14, 2015 in JP application 2012-522733.

\* cited by examiner

*Primary Examiner* — Amy Juedes
(74) *Attorney, Agent, or Firm* — Fitch, Even, Tabin & Flannery, LLP

(57) ABSTRACT

A polypeptide capable of strongly inducing and activating dendritic-cell-like cells for treating or prevent cancer by immunotherapy, and DNA encoding the polypeptide. The polypeptide is a polypeptide (a) or (b) consisting of a partial region of the REIC/Dkk-3 protein.

6 Claims, 51 Drawing Sheets
(42 of 51 Drawing Sheet(s) Filed in Color)

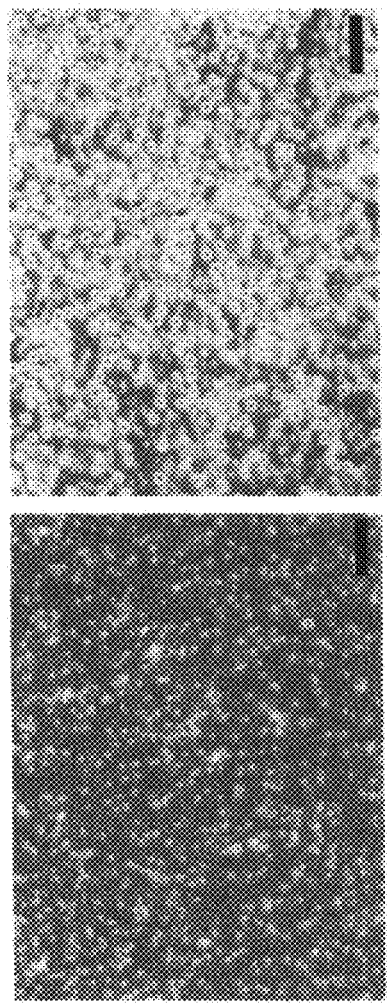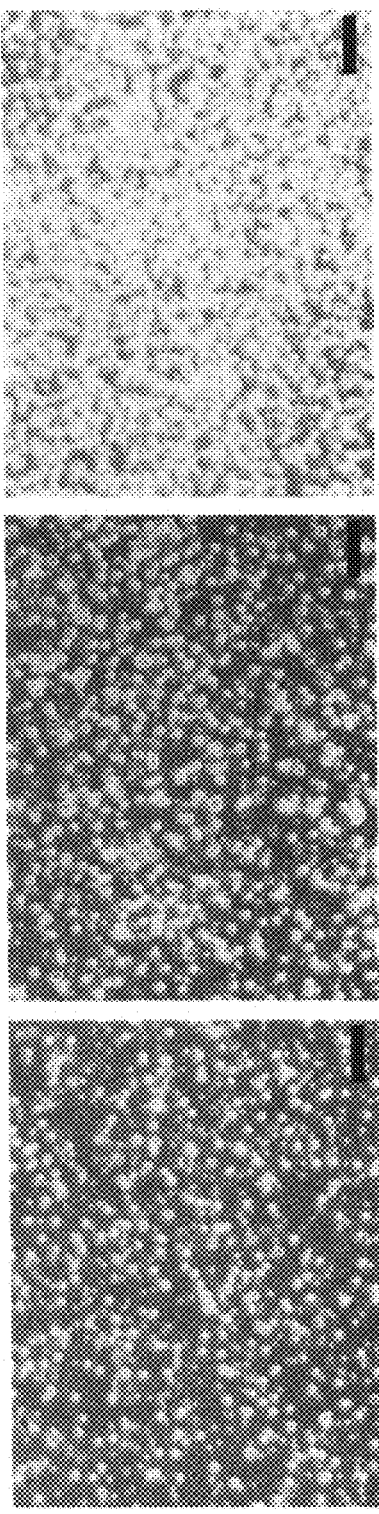

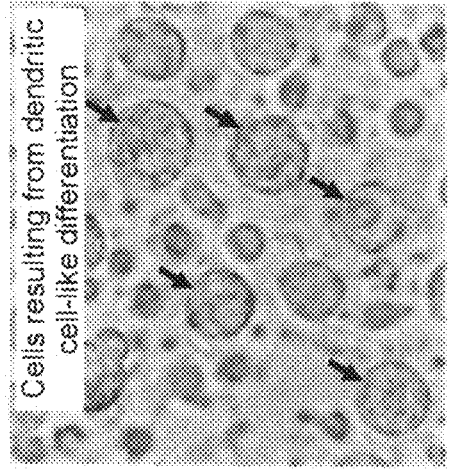
FIG. 3A  Day 7, No addition (Lymphocytes)
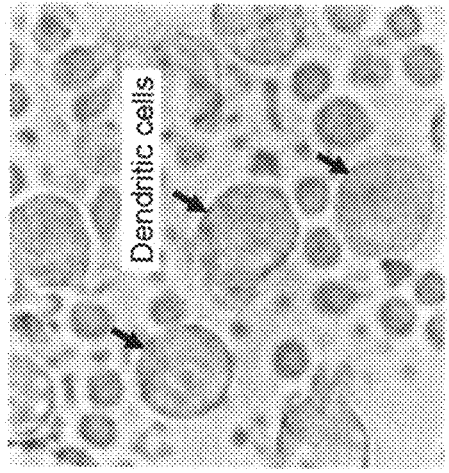
FIG. 3B  Day 7, IL-4 (2 ng/ml) + GM-CSF (2 ng/ml) (Dendritic cells)
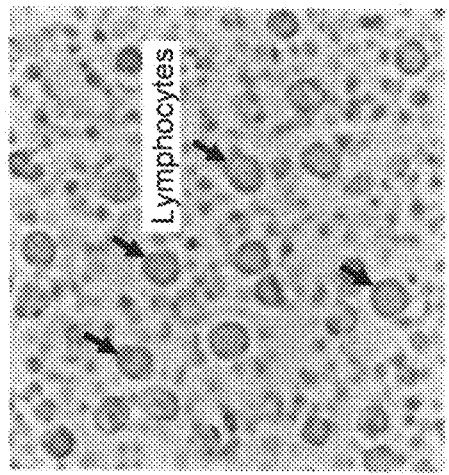
FIG. 3C  Day 7, REIC partial region 2 [Gly 184-Ile 329], (10 μg/ml) (Cells resulting from dendritic cell-like differentiation)

Day 7, REIC partial region 3 [Ser 114-Phe 267], (10 μg/ml)
Bar = 100 μm

Day 7, REIC partial region 1 [Arg 121-Ile 329], (10 μg/ml)

Day 7, No addition

Slightly expanded photographs

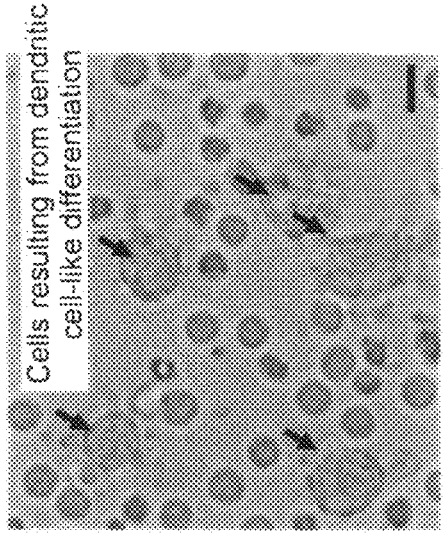
FIG. 7A — Day 7, No addition (Lymphocytes)
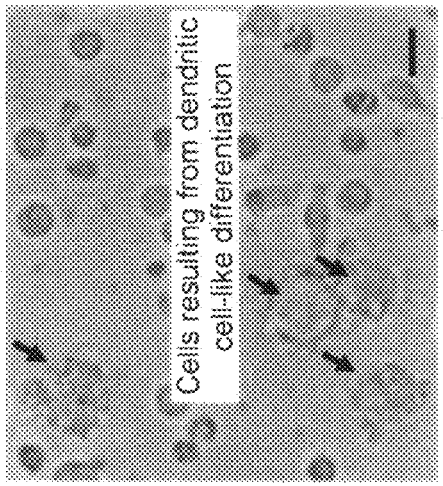
FIG. 7B — Day 7, REIC partial region 1 [Arg 121-Ile 329], (10 µg/ml) — Cells resulting from dendritic cell-like differentiation
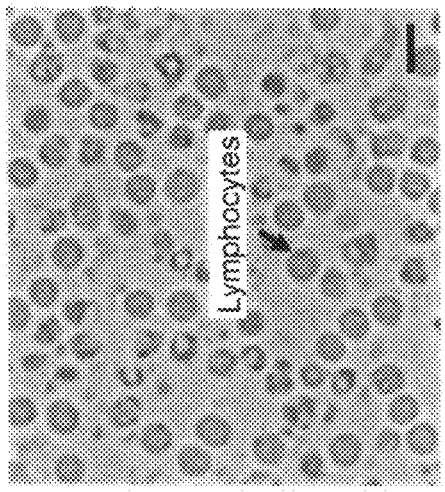
FIG. 7C — Day 7, REIC partial region 3 [Ser 114-Phe 267], (10 µg/ml) — Cells resulting from dendritic cell-like differentiation
Bar = 10 µm
Significantly expanded photographs

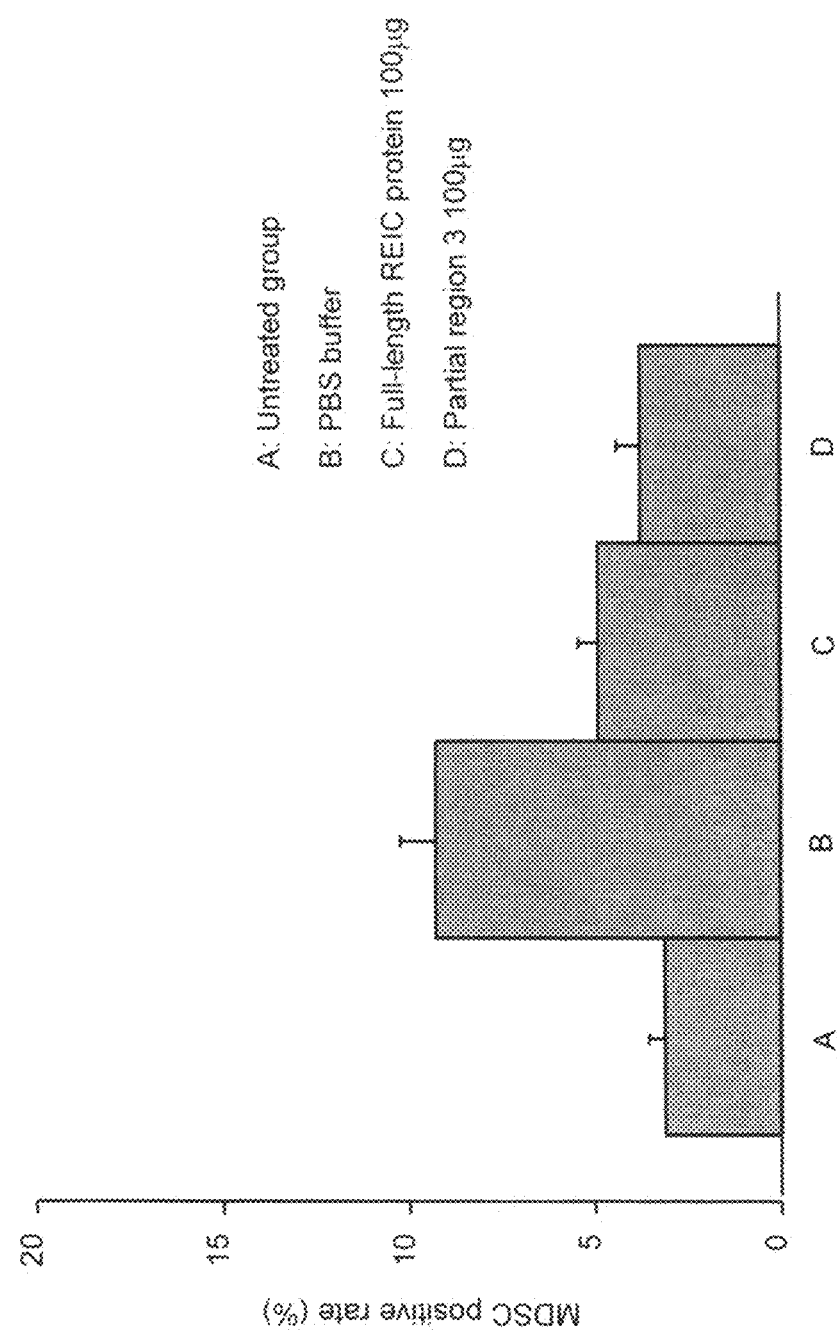

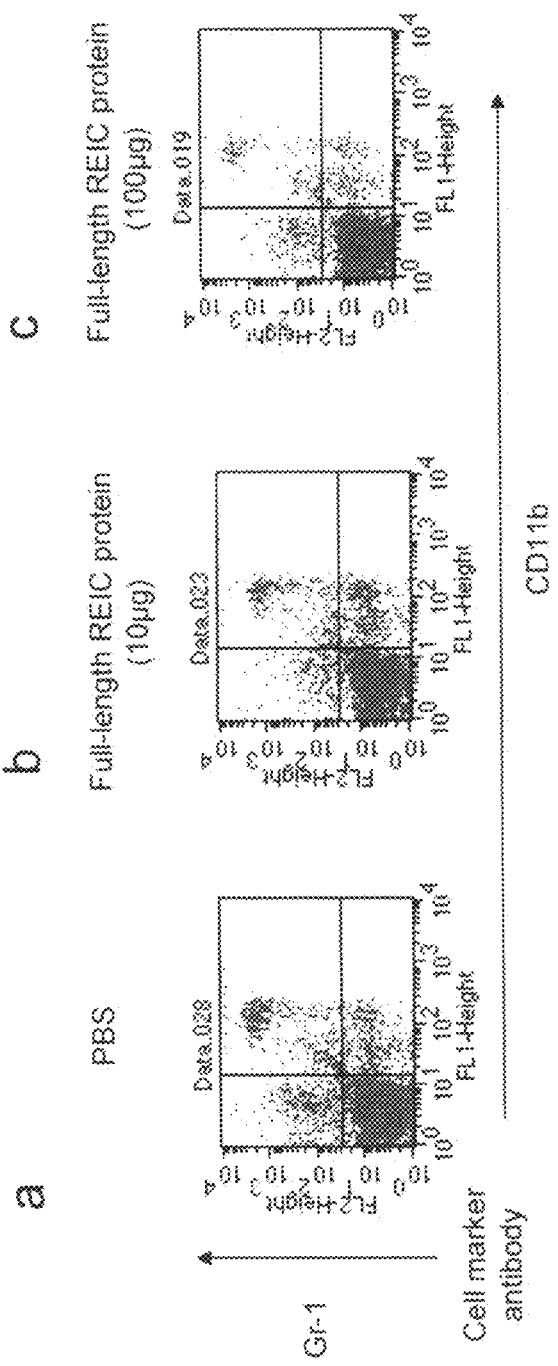

Fig. 20A

REIC ¹³⁴ TSVGDEEGRRSHECIIDEDCGPSMY ¹⁵⁸ (SEQ ID NO: 19)
DIC  ¹²⁰ SDSELGRRLHKLGVSKVTQVDFL ¹⁴² (SEQ ID NO: 16)

Fig. 20B

```
                    -R/K-R/K-X-X-R/K-        (SEQ ID NO: 20)

REIC       134 TSVGDEEGRRSHECIIDEDCGPSMY 158 (SEQ ID NO: 19)
DIC        120 SDSELGRRLHKLGVSKVTQVDFL 142 (SEQ ID NO: 18)
DOC2α        1 MRGRRGDRMTINIQE 15 (SEQ ID NO: 21)
DOC2β        1 MTLRRRGEKATISIQE 16 (SEQ ID NO: 22)
CD5        376 CGPLVYKKLVKKFRQKKQ 393 (SEQ ID NO: 23)
Peropsin   295 VAAHKKFRKAMLAMFK 310 (SEQ ID NO: 24)
Gβ1-4       42 RIQMRTRRTLRGHLAKIY 59 (SEQ ID NO: 25)
Gβ5         50 QFVMKTRRTLKGHGNKVL 67 (SEQ ID NO: 26)
CD155α     362 GIYFYWSKCSREVLWHCH 379 (SEQ ID NO: 27)
PTHR       478 TLALDFKRKARSGSSSYS 395 (SEQ ID NO: 28)
```

SEQUENCE LISTING

```
<160> NUMBER OF SEQ ID NOS: 28

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1 atg cag cgg ctt ggg gcc acc ctg ctg tgc ctg cta ctg gcg gcg gcg      48
Met Gln Arg Leu Gly Ala Thr Leu Leu Cys Leu Leu Leu Ala Ala Ala
1               5                   10                  15 gtc ccc acg gcc ccc gcg ccc gct ccg acg gcg acc tcg gct cca gtc      96
Val Pro Thr Ala Pro Ala Pro Ala Pro Thr Ala Thr Ser Ala Pro Val
                20                  25                  30 aag ccc ggc ccg gct ctc agc tac ccg cag gag gag gcc acc ctc aat     144
Lys Pro Gly Pro Ala Leu Ser Tyr Pro Gln Glu Glu Ala Thr Leu Asn
            35                  40                  45 gag atg ttc cgc gag gtt gag gaa ctg gtg gag gac acg cag cac aaa     192
Glu Met Phe Arg Glu Val Glu Glu Leu Val Glu Asp Thr Gln His Lys
        50                  55                  60 ttg cgc agc gcg gtg gaa gag atg gag gca gaa gaa gct gct gct aaa     240
Leu Arg Ser Ala Val Glu Glu Met Glu Ala Glu Glu Ala Ala Ala Lys
65                  70                  75                  80 gca tca tca gaa gtg aac ctg gca aac tta cct ccc agc tat cac aat     288
Ala Ser Ser Glu Val Asn Leu Ala Asn Leu Pro Pro Ser Tyr His Asn
                85                  90                  95 gag acc aac aca gac acg aag gtt gga aat aat acc atc cat gtg cac     336
Glu Thr Asn Thr Asp Thr Lys Val Gly Asn Asn Thr Ile His Val His
                100                 105                 110 cga gaa att cac aag ata acc aac aac cag gct cga caa atg gtc ttt     384
Arg Glu Ile His Lys Ile Thr Asn Asn Gln Ala Arg Gln Met Val Phe
            115                 120                 125 tca gag aca gtt atc aca tct gtg gga gac gaa gaa ggc aga agg agc     432
Ser Glu Thr Val Ile Thr Ser Val Gly Asp Glu Glu Gly Arg Arg Ser
        130                 135                 140
```

```
cac gag tgc atc atc gac gag gac tgt ggg ccc agc atg tac tgc cag    480
His Glu Cys Ile Ile Asp Glu Asp Cys Gly Pro Ser Met Tyr Cys Gln
145                 150                 155                 160 ttt gcc agc ttc cag tac acc tgc cag cca tgc cgg ggc cag agg atg    528
Phe Ala Ser Phe Gln Tyr Thr Cys Gln Pro Cys Arg Gly Gln Arg Met
                165                 170                 175 ctc tgc acc cgg gac agt gag tgc tgt gga gac cag ctg tgt gtc tgg    576
Leu Cys Thr Arg Asp Ser Glu Cys Cys Gly Asp Gln Leu Cys Val Trp
            180                 185                 190 ggt cac tgc acc aaa atg gcc acc agg ggc agc aat ggg acc atc tgt    624
Gly His Cys Thr Lys Met Ala Thr Arg Gly Ser Asn Gly Thr Ile Cys
        195                 200                 205 gac aac cag agg gac tgc cag ccg ggg ctg tgt tgt gcc ttc cag aga    672
Asp Asn Gln Arg Asp Cys Gln Pro Gly Leu Cys Cys Ala Phe Gln Arg
    210                 215                 220 ggc ctg ctg ttc cct gtg tgc ata ccc ctg ccc gtg gag ggc gag ctt    720
Gly Leu Leu Phe Pro Val Cys Ile Pro Leu Pro Val Glu Gly Glu Leu
225                 230                 235                 240 tgc cat gac ccc gcc agc cgg ctt ctg gac ctc atc acc tgg gag cta    768
Cys His Asp Pro Ala Ser Arg Leu Leu Asp Leu Ile Thr Trp Glu Leu
                245                 250                 255 gag cct gat gga gcc ttg gac cga tgc cct tgt gcc agt ggc ctc ctc    816
Glu Pro Asp Gly Ala Leu Asp Arg Cys Pro Cys Ala Ser Gly Leu Leu
            260                 265                 270 tgc cag ccc cac agc cac agc ctg gtg tat gtg tgc aag ccg acc ttc    864
Cys Gln Pro His Ser His Ser Leu Val Tyr Val Cys Lys Pro Thr Phe
        275                 280                 285 gtg ggg agc cgt gac caa gat ggg gag atc ctg ctg ccc aga gag gtc    912
Val Gly Ser Arg Asp Gln Asp Gly Glu Ile Leu Leu Pro Arg Glu Val
    290                 295                 300 ccc gat gag tat gaa gtt ggc agc ttc atg gag gag gtg cgc cag gag    960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag   1008
Leu Glu Asp Leu Glu Arg Ser Leu Thr Glu Glu Met Ala Leu Gly Glu
                325                 330                 335 cct gcg gct gcc gcc gct gca ctg ctg gga ggg gaa gag att tag       1053
Pro Ala Ala Ala Ala Ala Leu Leu Gly Gly Glu Glu Ile
            340                 345                 350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
                20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Val Glu Asp Thr Gln His Lys
        50                  55                  60

Leu Arg Ser Ala Val Glu Glu Met Glu Ala Glu Glu Ala Ala Ala Lys
65                  70                  75                  80

Ala Ser Ser Glu Val Asn Leu Ala Asn Leu Pro Pro Ser Tyr His Asn
                85                  90                  95
```

```
Glu Thr Asn Thr Asp Thr Lys Val Gly Asn Asn Thr Ile His Val His
                100                 105                 110

Arg Glu Ile His Lys Ile Thr Asn Asn Gln Ala Arg Gln Met Val Phe
            115                 120                 125

Ser Glu Thr Val Ile Thr Ser Val Gly Asp Glu Glu Gly Arg Arg Ser
        130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Ala Leu Leu Gly Gly Glu Glu Ile
            340                 345                 350

<210> SEQ ID NO 3
<211> LENGTH: 146
<212> TYPE: PRT
<213> ORGANISM: Homo sapiens

<400> SEQUENCE: 3

Gly Thr Ile Cys Asp Asn Gln Arg Asp Cys Gln Pro Gly Leu Cys Cys
1               5                   10                  15

Ala Phe Gln Arg Gly Leu Leu Phe Pro Val Cys Ile Pro Leu Pro Val
            20                  25                  30

Glu Gly Glu Leu Cys His Asp Pro Ala Ser Arg Leu Leu Asp Leu Ile
        35                  40                  45

Thr Trp Glu Leu Glu Pro Asp Gly Ala Leu Asp Arg Cys Pro Cys Ala
    50                  55                  60

Ser Gly Leu Leu Cys Gln Pro His Ser His Ser Leu Val Tyr Val Cys
65                  70                  75                  80

Lys Pro Thr Phe Val Gly Ser Arg Asp Gln Asp Gly Glu Ile Leu Leu
                85                  90                  95

Pro Arg Glu Val Pro Asp Glu Tyr Glu Val Gly Ser Phe Met Glu Glu
            100                 105                 110
```

```
Val Arg Gln Glu Leu Glu Asp Leu Glu Arg Ser Leu Thr Glu Glu Met
            115                 120                 125

Ala Leu Gly Glu Pro Ala Ala Ala Ala Ala Leu Leu Gly Gly Glu
130                 135                 140

Glu Ile
145

<210> SEQ ID NO 4
<211> LENGTH: 438
<212> TYPE: DNA
<213> ORGANISM: Homo sapiens

<400> SEQUENCE: 4
gggaccatct gtgacaacca gagggactgc cagccggggc tgtgctgtgc cttccagaga      60
ggcctgctgt tccctgtgtg catacccctg cccgtggagg gcgagctttg ccatgacccc     120
gccagccggc ttctggacct catcacctgg gagctagagc ctgatggagc cttggaccga     180
tgcccttgtg ccagtggcct cctctgccag ccccacagcc acagcctggt gtatgtgtgc     240
aagccgacct tcgtggggag ccgtgaccaa gatggggaga tcctgctgcc cagagaggtc     300
cccgatgagt atgaagttgg cagcttcatg gaggaggtgc gccaggagct ggaggacctg     360
gagaggagcc tgactgaaga gatggcgctg ggggagcctg cggctgccgc cgctgcactg     420
ctgggagggg aagagatt                                                   438

<210> SEQ ID NO 5
<211> LENGTH: 209
<212> TYPE: PRT
<213> ORGANISM: Homo sapiens

<400> SEQUENCE: 5

Arg Arg Ser His Glu Cys Ile Ile Asp Glu Asp Cys Gly Pro Ser Met
1               5                   10                  15

Tyr Cys Gln Phe Ala Ser Phe Gln Tyr Thr Cys Gln Pro Cys Arg Gly
            20                  25                  30

Gln Arg Met Leu Cys Thr Arg Asp Ser Glu Cys Cys Gly Asp Gln Leu
        35                  40                  45

Cys Val Trp Gly His Cys Thr Lys Met Ala Thr Arg Gly Ser Asn Gly
    50                  55                  60

Thr Ile Cys Asp Asn Gln Arg Asp Cys Gln Pro Gly Leu Cys Cys Ala
65                  70                  75                  80

Phe Gln Arg Gly Leu Leu Phe Pro Val Cys Ile Pro Leu Pro Val Glu
                85                  90                  95

Gly Glu Leu Cys His Asp Pro Ala Ser Arg Leu Leu Asp Leu Ile Thr
            100                 105                 110

Trp Glu Leu Glu Pro Asp Gly Ala Leu Asp Arg Cys Pro Cys Ala Ser
        115                 120                 125

Gly Leu Leu Cys Gln Pro His Ser His Ser Leu Val Tyr Val Cys Lys
    130                 135                 140

Pro Thr Phe Val Gly Ser Arg Asp Gln Asp Gly Glu Ile Leu Leu Pro
145                 150                 155                 160

Arg Glu Val Pro Asp Glu Tyr Glu Val Gly Ser Phe Met Glu Glu Val
                165                 170                 175

Arg Gln Glu Leu Glu Asp Leu Glu Arg Ser Leu Thr Glu Glu Met Ala
            180                 185                 190
```

```
Leu Gly Glu Pro Ala Ala Ala Ala Ala Leu Leu Gly Gly Glu Glu
    195                 200                 205

Ile

<210> SEQ ID NO 6
<211> LENGTH: 627
<212> TYPE: DNA
<213> ORGANISM: Homo sapiens

<400> SEQUENCE: 6
agaaggagcc acgagtgcat catcgacgag gactgtgggc ccagcatgta ctgccagttt        60
gccagcttcc agtacacctg ccagccatgc cggggccaga ggatgctctg cacccgggac       120
agtgagtgct gtggagacca gctgtgtgtc tggggtcact gcaccaaaat ggccaccagg       180
ggcagcaatg gaccatctg tgacaaccag agggactgcc agccggggct gtgctgtgcc        240
ttccagagag gcctgctgtt ccctgtgtgc atacccctgc ccgtggaggg cgagctttgc       300
catgaccccg ccagccggct tctggacctc atcacctggg agctagagcc tgatggagcc       360
ttggaccgat gcccttgtgc cagtggcctc ctctgccagc cccacagcca cagcctggtg       420
tatgtgtgca gccgacctt cgtggggagc cgtgaccaag atggggagat cctgctgccc        480
agagaggtcc ccgatgagta tgaagttggc agcttcatgg aggaggtgcg ccaggagctg       540
gaggacctgg agaggagcct gactgaagag atggcgctgg gggagcctgc ggctgccgcc       600
gctgcactgc tgggagggga agagatt                                            627

<210> SEQ ID NO 7
<211> LENGTH: 154
<212> TYPE: PRT
<213> ORGANISM: Homo sapiens

<400> SEQUENCE: 7

Ser Val Gly Asp Glu Glu Gly Arg Arg Ser His Glu Cys Ile Ile Asp
1               5                   10                  15

Glu Asp Cys Gly Pro Ser Met Tyr Cys Gln Phe Ala Ser Phe Gln Tyr
            20                  25                  30

Thr Cys Gln Pro Cys Arg Gly Gln Arg Met Leu Cys Thr Arg Asp Ser
        35                  40                  45

Glu Cys Cys Gly Asp Gln Leu Cys Val Trp Gly His Cys Thr Lys Met
    50                  55                  60

Ala Thr Arg Gly Ser Asn Gly Thr Ile Cys Asp Asn Gln Arg Asp Cys
65                  70                  75                  80

Gln Pro Gly Leu Cys Cys Ala Phe Gln Arg Gly Leu Leu Phe Pro Val
                85                  90                  95

Cys Thr Pro Leu Pro Val Glu Gly Glu Leu Cys His Asp Pro Ala Ser
            100                 105                 110

Arg Leu Leu Asp Leu Ile Thr Trp Glu Leu Glu Pro Asp Gly Ala Leu
        115                 120                 125

Asp Arg Cys Pro Cys Ala Ser Gly Leu Leu Cys Gln Pro His Ser His
    130                 135                 140

Ser Leu Val Tyr Val Cys Lys Pro Thr Phe
145                 150

<210> SEQ ID NO 8
<211> LENGTH: 462
<212> TYPE: DNA
<213> ORGANISM: Homo sapiens
```

-continued

<400> SEQUENCE: 8

```
tctgtgggag acgaagaagg cagaaggagc cacgagtgca tcatcgacga ggactgtggg      60
cccagcatgt actgccagtt tgccagcttc cagtacacct gccagccatg ccggggccag     120
aggatgctct gcacccggga cagtgagtgc tgtggagacc agctgtgtgt ctggggtcac     180
tgcaccaaaa tggccaccag ggcagcaat gggaccatct gtgacaacca gagggactgc     240
cagccggggc tgtgctgtgc cttccagaga ggcctgctgt tccctgtgtg catacccctg     300
cccgtggagg gcgagctttg ccatgacccc gccagccggc ttctggacct catcacctgg     360
gagctagagc ctgatggagc cttggaccga tgcccttgtg ccagtggcct cctctgccag     420
ccccacagcc acagcctggt gtatgtgtgc aagccgacct tc                        462
```

<210> SEQ ID NO 9
<211> LENGTH: 84
<212> TYPE: PRT
<213> ORGANISM: Homo sapiens

<400> SEQUENCE: 9

Gly Thr Ile Cys Asp Asn Gln Arg Asp Cys Gln Pro Gly Leu Cys Cys
1               5                   10                  15

Ala Phe Gln Arg Gly Leu Leu Phe Pro Val Cys Ile Pro Leu Pro Val
            20                  25                  30

Glu Gly Glu Leu Cys His Asp Pro Ala Ser Arg Leu Leu Asp Leu Ile
        35                  40                  45

Thr Trp Glu Leu Glu Pro Asp Gly Ala Leu Asp Arg Cys Pro Cys Ala
    50                  55                  60

Ser Gly Leu Leu Cys Gln Pro His Ser His Ser Leu Val Tyr Val Cys
65                  70                  75                  80

Lys Pro Thr Phe

<210> SEQ ID NO 10
<211> LENGTH: 252
<212> TYPE: DNA
<213> ORGANISM: Homo sapiens

<400> SEQUENCE: 10

```
gggaccatct gtgacaacca gagggactgc cagccggggc tgtgctgtgc cttccagaga      60
ggcctgctgt tccctgtgtg catacccctg cccgtggagg gcgagctttg ccatgacccc     120
gccagccggc ttctggacct catcacctgg gagctagagc ctgatggagc cttggaccga     180
tgcccttgtg ccagtggcct cctctgccag ccccacagcc acagcctggt gtatgtgtgc     240
aagccgacct tc                                                         252
```

<210> SEQ ID NO 11
<211> LENGTH: 36
<212> TYPE: PRT
<213> ORGANISM: Artificial
<220> FEATURE:
<223> OTHER INFORMATION: synthetic

<400> SEQUENCE: 11

Met Gly Ser Ser His His His His His His Ser Gly Leu Val Pro
1               5                   10                  15

Arg Gly Ser His Met Ala Ser Met Thr Gly Gly Gln Gln Met Gly Arg
            20                  25                  30

Asp Pro Asn Ser
        35

```
<210> SEQ ID NO 12
<211> LENGTH: 31
<212> TYPE: DNA
<213> ORGANISM: Artificial
<220> FEATURE:
<223> OTHER INFORMATION: primer

<400> SEQUENCE: 12
acgcgtcgac catgcagcgg cttggggcca c                                31

<210> SEQ ID NO 13
<211> LENGTH: 37
<212> TYPE: DNA
<213> ORGANISM: Artificial
<220> FEATURE:
<223> OTHER INFORMATION: primer

<400> SEQUENCE: 13
ttcctttttt gcggccgcta aatctcttcc cctccca                          37

<210> SEQ ID NO 14
<211> LENGTH: 29
<212> TYPE: DNA
<213> ORGANISM: Artificial
<220> FEATURE:
<223> OTHER INFORMATION: primer

<400> SEQUENCE: 14
ccggaattca tggaagacta ccaggctgc                                   29

<210> SEQ ID NO 15
<211> LENGTH: 29
<212> TYPE: DNA
<213> ORGANISM: Artificial
<220> FEATURE:
<223> OTHER INFORMATION: primer

<400> SEQUENCE: 15
gggaagcttt caaatagaca gtccgaagg                                   29

<210> SEQ ID NO 16
<211> LENGTH: 23
<212> TYPE: PRT
<213> ORGANISM: Artificial
<220> FEATURE:
<223> OTHER INFORMATION: synthetic

<400> SEQUENCE: 16

Ser Asp Ser Glu Leu Gly Arg Arg Leu His Lys Leu Gly Val Ser Lys
1               5                   10                  15

Val Thr Gln Val Asp Phe Leu
            20

<210> SEQ ID NO 17
<211> LENGTH: 22
<212> TYPE: PRT
<213> ORGANISM: Artificial
<220> FEATURE:
<223> OTHER INFORMATION: synthetic

<400> SEQUENCE: 17

Val Gly Asp Glu Glu Gly Arg Arg Ser His Glu Cys Ile Ile Asp Glu
1               5                   10                  15

Asp Cys Gly Pro Ser Met
            20
```

```
<210> SEQ ID NO 18
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 18

Glu Xaa Gly Arg Arg Xaa His
1               5

<210> SEQ ID NO 19
<211> LENGTH: 25
<212> TYPE: PRT
<213> ORGANISM: Artificial
<220> FEATURE:
<223> OTHER INFORMATION: synthetic

<400> SEQUENCE: 19

Thr Ser Val Gly Asp Glu Gly Arg Arg Ser His Glu Cys Ile Ile
1               5                   10                  15

Asp Glu Asp Cys Gly Pro Ser Met Tyr
            20                  25

<210> SEQ ID NO 20
<211> LENGTH: 5
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(2)
<223> OTHER INFORMATION: Xaa is r or k
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is r or k

<400> SEQUENCE: 20

Xaa Xaa Xaa Xaa Xaa
1               5

<210> SEQ ID NO 21
<211> LENGTH: 15
<212> TYPE: PRT
<213> ORGANISM: Artificial
<220> FEATURE:
<223> OTHER INFORMATION: synthetic

<400> SEQUENCE: 21

Met Arg Gly Arg Arg Gly Asp Arg Met Thr Ile Asn Ile Gln Glu
1               5                   10                  15

<210> SEQ ID NO 22
<211> LENGTH: 16
<212> TYPE: PRT
<213> ORGANISM: Artificial
```

<220> FEATURE:
<223> OTHER INFORMATION: synthetic

<400> SEQUENCE: 22

Met Thr Leu Arg Arg Arg Gly Glu Lys Ala Thr Ile Ser Ile Gln Glu
1               5                   10                  15

<210> SEQ ID NO 23
<211> LENGTH: 18
<212> TYPE: PRT
<213> ORGANISM: Artificial
<220> FEATURE:
<223> OTHER INFORMATION: synthetic

<400> SEQUENCE: 23

Cys Gly Pro Leu Val Tyr Lys Lys Leu Val Lys Lys Phe Arg Gln Lys
1               5                   10                  15

Lys Gln

<210> SEQ ID NO 24
<211> LENGTH: 16
<212> TYPE: PRT
<213> ORGANISM: Artificial
<220> FEATURE:
<223> OTHER INFORMATION: synthetic

<400> SEQUENCE: 24

Val Ala Ala His Lys Lys Phe Arg Lys Ala Met Leu Ala Met Phe Lys
1               5                   10                  15

<210> SEQ ID NO 25
<211> LENGTH: 18
<212> TYPE: PRT
<213> ORGANISM: Artificial
<220> FEATURE:
<223> OTHER INFORMATION: synthetic

<400> SEQUENCE: 25

Arg Ile Gln Met Arg Thr Arg Thr Leu Arg Gly His Leu Ala Lys
1               5                   10                  15

Ile Tyr

<210> SEQ ID NO 26
<211> LENGTH: 18
<212> TYPE: PRT
<213> ORGANISM: Artificial
<220> FEATURE:
<223> OTHER INFORMATION: synthetic

<400> SEQUENCE: 26

Gln Phe Val Met Lys Thr Arg Arg Thr Leu Lys Gly His Gly Asn Lys
1               5                   10                  15

Val Leu

<210> SEQ ID NO 27
<211> LENGTH: 18
<212> TYPE: PRT
<213> ORGANISM: Artificial
<220> FEATURE:
<223> OTHER INFORMATION: synthetic

```
<400> SEQUENCE: 27

Gly Ile Tyr Phe Tyr Trp Ser Lys Cys Ser Arg Glu Val Leu Trp His
1               5                   10                  15

Cys His

<210> SEQ ID NO 28
<211> LENGTH: 18
<212> TYPE: PRT
<213> ORGANISM: Artificial
<220> FEATURE:
<223> OTHER INFORMATION: synthetic

<400> SEQUENCE: 28

Thr Leu Ala Leu Asp Phe Lys Arg Lys Ala Arg Ser Gly Ser Ser Ser
1               5                   10                  15

Tyr Ser
```

US 9,644,013 B2

PARTIAL REGION POLYPEPTIDE OF REIC/DKK-3 PROTEIN

CROSS-REFERENCE TO RELATED APPLICATIONS

This Application is as Division of U.S. patent application Ser. No. 13/807,747 filed Dec. 31, 2012, which is a U.S. National Stage Application filed under 35 U.S.C. §371 of International Application PCT/JP2011/065644, filed Jul. 1, 2011, designating the United States, which claims priority from Japanese Patent Application 2010-150935, filed Jul. 1, 2010, and Japanese Patent Application 2011-014319, filed Jan. 26, 2011, the complete disclosures of which, including sequence listings, photographs and color figures, are hereby incorporated herein by reference in their entirety for all purposes.

TECHNICAL FIELD

The present invention relates to a pharmaceutical composition for treating or preventing cancer, which enhances anticancer immune activity.

BACKGROUND ART

The REIC/Dkk-3 gene is known to be associated with cell immortalization, and suppression of expression of such genes in cancer cells has been reported (International Publication WO01/038523 pamphlet, Tsuji, T. et al., Biochem Biophys Res Commun 268, 20-4 (2000), Tsuji, T. et al., Biochem Biophys Res Commun 289, 257-63 (2001), Nozaki, I. et al., Int J Oncol 19, 117-21 (2001) and Kurose, K. et al., J Urol 171, 1314-8 (2004)).

The REIC/Dkk-3 gene is a member of the Dkk family, and it is suggested that such gene inhibits Wnt signal transduction via a Wnt receptor (Bafico, A. et al., Nat Cell Biol 3, 683-6 (2001) and Hoang, B. H. et al., Cancer Res 64, 2734-9 (2004)). It is reported that the Wnt gene plays multiple roles in important biological conditions, such as cell growth, differentiation, and canceration (Moon, R. T. et al., Science 296, 1644-6 (2002)).

It has been reported concerning REIC/Dkk-3 that when the full-length REIC/Dkk-3 protein is added at a concentration of 10 µg/ml to a culture solution in which peripheral blood mononuclear cells (monocytes) are cultured, the cells differentiate into dendritic-cell-like cells (International Publication WO09/119874 pamphlet).

In general, there are only a small number of references that disclose substances recognized as having the ability to induce dendritic cell(-like) differentiation from blood precursor cells. Most such substances are well-known cytokines. For instance, there are many reports on the combined use of GM-CSF and IL-4; that is, the induction of dendritic cell differentiation from monocytes through the addition of GM-CSF and IL-4 to the culture solution. This combination is called the "gold standard" for dendritic cell differentiation. In addition, as substances capable of inducing dendritic cell differentiation when used alone or in combination, TNF-alpha, IL-2, IL-3, IL-6, IL-7, IL-12, IL-13, IL-15, HGF (hepatocyte growth factor), a CD40 ligand, M-CSF, an Flt3 ligand, and TGF-β have been reported. Among these proteins, known examples of a substance capable of inducing precursor cells to differentiate into dendritic cell(-like) cells when used alone include IL-2, IL-15, HGF, and a CD40 ligand, as in the case of the full-length REIC/Dkk-3 protein. Of these, only IL-2 has been confirmed to have in vivo anticancer effects. A possible reason why GM-CSF is unable to exhibit such effects is that it induces not only anticancer immunity, but also the differentiation of immunosuppressive cells represented by bone marrow-derived immunosuppressive cells (myeloid-derived suppressor cells (MDSC)) or immunoregulatory T cells (Treg) so as to activate a "negative immune system" (Parmiani, G et al., Annals of Oncology 18, 226-32 (2007)).

SUMMARY OF THE INVENTION

An object of the present invention is to provide a polypeptide capable of strongly inducing and activating dendritic-cell-like cells, so as to be able to treat or prevent cancer by immunotherapy, and DNA encoding the polypeptide.

The present inventors have revealed the usability/superiority of a full-length REIC/Dkk-3 protein in in vivo immune/inflammatory phenomena and the possible use thereof in wide-ranging fields and diseases (International Publication WO09/119874 pamphlet).

The present inventors have further examined the activity of a partial region of the REIC/Dkk-3 protein, and thus discovered that such a specific partial region thereof has strong bioactivity to induce dendritic cell-like differentiation from monocytes and that the bioactivity is significantly higher than that of the full-length REIC/Dkk-3 protein. This demonstrates that the specific partial region of the REIC/Dkk-3 protein induces dendritic-cell-like cell differentiation from monocytes, and can be used for treating or preventing cancer by activating anticancer immunity.

It has been reported that as such an immunological cancer therapeutic agent, an IL-2 protein may have therapeutic effects on specific types of cancer such as renal cell carcinoma. However, it is a clinically known fact that the types of cancer to which the IL-2 protein can be appropriately administered and the effects thereof are limited. It has been confirmed that the REIC/Dkk-3 protein is expressed and secreted at decreased levels in almost all types of cancer. Hence, the REIC/Dkk-3 protein may be used as a cancer therapeutic agent having the effect of activating anticancer immunity for various types of cancer, and the therapeutic effects thereof can be superior to those of IL-2.

As described above, the present inventors have discovered that a specific partial region of the REIC/Dkk-3 protein has stronger "bioactivity to induce dendritic cell-like differentiation from monocytes" than the full-length REIC/Dkk-3 protein, and thus they have completed the present invention.

Specifically, the present invention is as follows.

[1] A polypeptide that is any one of the following polypeptides (a) to (e), which consists of a partial region of a REIC/Dkk-3 protein:

(a) a polypeptide consisting of a partial region of the REIC/Dkk-3 protein, which consists of an amino acid sequence selected from the group consisting of the amino acid sequences shown in SEQ ID NO: 3, SEQ ID NO: 5, SEQ ID NO: 7 and SEQ ID NO: 9, and the amino acid sequence of a polypeptide that contains the partial region consisting of Gly at position 205 to Phe at position 288 of the amino acid sequence shown in SEQ ID NO: 2, and consists of a fragment of the partial region consisting of Ser at position 135 to Ile at position 350 of the amino acid sequence shown in SEQ ID NO: 2;

(b) a polypeptide having activity of inducing dendritic-cell-like cell differentiation from monocytes, which is a polypeptide protein consisting of an amino acid sequence that has a substitution, a deletion, or an addition of 1 or several amino acids with respect to an amino acid sequence selected from the group consisting of the amino acid sequences shown in SEQ ID NO: 3, SEQ ID NO: 5, SEQ ID NO: 7 and SEQ ID NO: 9, and the amino acid sequence of a polypeptide that contains the partial region consisting of Gly at position 205 to Phe at position 288 of the amino acid sequence shown in SEQ ID NO: 2, and consists of a fragment of the partial region consisting of Ser at position 135 to Ile at position 350 of the amino acid sequence shown in SEQ ID NO: 2;

(c) a polypeptide consisting of a partial region of the REIC/Dkk-3 protein, which can bind to a Tctex-1 protein and consists of the amino acid sequence shown in SEQ ID NO: 17, and;

(d) a polypeptide consisting of an amino acid sequence having a substitution, a deletion, or an addition of 1 or several amino acids with respect to the amino acid sequence shown in SEQ ID NO: 17 and having the activity of binding to the Tctex-1 protein; and (e) a polypeptide consisting of a partial region of the REIC/Dkk-3 protein and being capable of binding to the Tctex-1 protein, which contains the consensus sequence shown in SEQ ID NO: 18 and consists of 7 to 22 amino acid residues.

[2] DNA that is any one of the following DNAs (0 to (1), which encodes a polypeptide consisting of a partial region of a REIC/Dkk-3 protein;

(f) DNA consisting of a nucleotide sequence selected from the group consisting of the nucleotide sequences shown in SEQ ID NO: 4, SEQ ID NO: 6, SEQ ID NO: 8 and SEQ ID NO: 10, and a nucleotide sequence that contains the partial sequence consisting of g at position 613 to c at position 864 of the nucleotide sequence shown in SEQ ID NO: 1, and consists of a fragment of the partial sequence consisting of t at position 403 to t at position 1050 of the nucleotide sequence shown in SEQ ID NO: 1;

(g) DNA hybridizing under stringent conditions to DNA consisting of a nucleotide sequence complementary to a nucleotide sequence selected from the group consisting of the nucleotide sequences shown in SEQ ID NO: 4, SEQ ID NO: 6, SEQ ID NO: 8 and SEQ ID NO: 10, and a nucleotide sequence that contains the partial sequence consisting of g at position 613 to c at position 864 of the nucleotide sequence shown in SEQ ID NO: 1, and consists of a fragment of the partial sequence consisting of t at position 403 to t at position 1050 of the nucleotide sequence shown in SEQ ID NO: 1, and encoding a polypeptide having activity of inducing dendritic-cell-like cell differentiation from monocytes;

(h) DNA consisting of a nucleotide sequence having a deletion, a substitution, or an addition of 1 or several nucleotides with respect to a nucleotide sequence selected from the group consisting of the nucleotide sequences shown in SEQ ID NO: 4, SEQ ID NO: 6, SEQ ID NO: 8 and SEQ ID NO: 10, and a nucleotide sequence that contains the partial sequence consisting of g at position 613 to c at position 864 of the nucleotide sequence shown in SEQ ID NO: 1, and consists of a fragment of the partial sequence consisting of t at position 403 to t at position 1050 of the nucleotide sequence shown in SEQ ID NO: 1, and encoding a polypeptide having activity of inducing dendritic-cell-like cell differentiation from monocytes;

(i) DNA consisting of a DNA sequence that encodes an amino acid sequence selected from the group consisting of the amino acid sequences shown in SEQ ID NO: 3, SEQ ID NO: 5, SEQ ID NO: 7 and SEQ ID NO: 9, and the amino acid sequence of a polypeptide that contains the partial region consisting of Gly at position 205 to Phe at position 288 of the amino acid sequence shown in SEQ ID NO: 2, and consists of a fragment of the partial region consisting of the Ser at position 135 to Ile at position 350 of the amino acid sequence shown in SEQ ID NO: 2, and encoding a polypeptide having activity of inducing dendritic-cell-like cell differentiation from monocytes;

(j) DNA encoding a polypeptide that consists of a partial region of the REIC/Dkk-3 protein and is capable of binding to the Tctex-1 protein, which consists of the nucleotide sequence consisting of g at position 4 to g at position 69 of the nucleotide sequence shown in SEQ ID NO: 8;

(k) DNA hybridizing under stringent conditions to DNA consisting of a nucleotide sequence complementary to the nucleotide sequence consisting of g at position 4 to g at position 69 of the nucleotide sequence shown in SEQ ID NO: 8, and encoding a polypeptide having activity of binding to the Tctex-1 protein; and (l) DNA encoding a polypeptide that consists of a partial region of the REIC/Dkk-3 protein, is capable of binding to the Tctex-1 protein, consists of the DNA sequence encoding the amino acid sequence shown in SEQ ID NO: 17, and has activity of binding to the Tctex-1 protein.

[3] A vector, containing the DNA of [2].

[4] The vector of [3], wherein the vector is an adenovirus vector.

[5] An agent for inducing dendritic-cell-like cell differentiation from monocytes, containing the polypeptide of [1] consisting of a partial region of the REIC/Dkk-3 protein as an active ingredient.

[6] An agent for accelerating the induction of differentiation to immunoactivation cells selected from the group consisting of dendritic cells, helper T cells, CTL, and NK cells, containing the polypeptide of [1] consisting of a partial region of the REIC/Dkk-3 protein as an active ingredient.

[7] An agent for inhibiting the induction of differentiation to immunosuppressively functioning cells that are myeloid-derived suppressor cells (MDSC) or immunoregulatory T cells (Treg), containing the polypeptide of [1] consisting of a partial region of the REIC/Dkk-3 protein as an active ingredient.

[8] An anticancer agent, containing the polypeptide of [1] consisting of a partial region of the REIC/Dkk-3 protein as an active ingredient.

[9] An agent for inducing dendritic-cell-like cell differentiation from monocytes, containing the DNA of [2] that encodes the polypeptide consisting of a partial region of the REIC/Dkk-3 protein or the vector of [3] or [4] as an active ingredient.

[10] An agent for accelerating the induction of differentiation to immunoactivation cells selected from the group consisting of dendritic cells, helper T cells, CTL, and NK cells, containing the DNA of [2] encoding the polypeptide consisting of a partial region of the REIC/Dkk-3 protein or the vector of [3] or [4] as an active ingredient.

[11] An agent for inhibiting the induction of differentiation to immunosuppressive cells that are myeloid-derived suppressor cells (MDSC) or immunoregulatory T cells (Treg), containing the DNA of [2] encoding the polypeptide consisting of a partial region of the REIC/Dkk-3 protein or the vector of [3] or [4] as an active ingredient.

[12] An anticancer agent, containing the DNA of [2] encoding the polypeptide consisting of a partial region of the REIC/Dkk-3 protein or the vector of [3] or [4] as an active ingredient.

[13] A method for inducing dendritic-cell-like cell differentiation from CD14 positive monocytes, comprising culturing monocytes collected from an animal in vitro in the presence of the polypeptide of [1] consisting of a partial region of the REIC/Dkk-3 protein.

[14] The method of [13], wherein the monocytes are peripheral blood monocytes.

This description includes part or all of the contents as disclosed in the description and/or drawings of Japanese Patent Application Nos. 2010-150935 and 2011-014319, which are priority documents of the present application.

BRIEF DESCRIPTION OF THE DRAWINGS

The patent or application file contains drawings executed in color. Copies of this patent or patent application publication with color drawing(s) will be provided by the Office upon request and payment of the necessary fee.

FIG. 2 shows photographs showing phase contrast microscopic images of PBMCs cultured alone (no addition) (FIG. 2A), cultured in the presence of GM-CSF+IL-4 (FIG. 2B)(2 ng/ml each), the full-length human REIC/Dkk-3 protein (FIG. 2C), the partial region 1 [Arg 121-Ile 329] (FIG. 2D), and the partial region 2 [Gly 184-Ile 329] (FIG. 2E) (10 µg/ml) thereof, for 7 days (slightly expanded images), respectively.

FIG. 3 shows the phase contrast microscopic images of PBMCs cultured alone (no addition) (FIG. 3A), cultured in the presence of GM-CSF+IL-4 (FIG. 3B) (2 ng/ml each), and the partial region 2 [Gly 184-Ile 329] (10 µg/ml) (FIG. 3C) for 7 days (significantly expanded images), respectively.

FIG. 5-1 shows protocols for a production method and a purification method for the partial region 3 [Ser 114-Phe 267] of a REIC/Dkk-3 protein.

FIG. 5-2 shows a chart of purification by 1st ion exchange chromatography upon purification of the partial region 3 [Ser 114-Phe 267] of the REIC/Dkk-3 protein.

FIG. 5-3 shows a chart of purification by $2^{nd}$ ion exchange chromatography upon purification of the partial region 3 [Ser 114-Phe 267] of the REIC/Dkk-3 protein.

FIG. 7 shows photographs showing the induction of dendritic cell-like differentiation from peripheral blood monocytes through the addition of the human REIC protein expressed by human tissue-derived cultured cells. Specifically, these photographs are significantly expanded phase-contrast microscopic images of dendritic-cell-like cells (on day 7) resulting from differentiation induction with the presence of cells alone (no addition) (FIG. 7A), the partial region 1 [Arg 121-Ile 329](10 µg/ml) (FIG. 7B) or the partial region 3 [Ser 114-Phe 267] (10 µg/ml) (FIG. 7C) of the REIC/Dkk-3 protein.

FIG. 11C-a shows the result of administration of PBS, FIG. 11C-b shows the result of administration of the human full-length REIC/Dkk-3 protein, and FIG. 11C-c shows the result of administration of the partial region 3.

FIG. 12A is a graph showing the positive rate (%) of myeloid-derived suppressor cells in each type of peripheral blood at the time (immediately before euthanasia) of completion of an experiment of treatment with a REIC/Dkk-3 protein (full-length or partial region 3), in an untreated group, or in a group treated with PBS buffer.

FIG. 17A-1 shows the result (cytogram) of measuring by flow cytometric analysis the positive rate (%) of MDSC (Gr-1+, CD11b+) in each type of peripheral blood collected at the time (immediately before euthanasia) of completion of an experiment of treatment with the full-length REIC/Dkk-3 protein (10 µg, 100 µg) or from a group treated with PBS buffer. FIG. 17A-1a shows the results of using PBS, FIG. 17A-1b shows the results of using the full-length REIC/Dkk-3 protein (10 µg), and FIG. 17A-1c shows the results of using the full-length REIC/Dkk-3 protein (100 µg).

FIG. 17A-2 shows the result (graph showing positive rate (%)) of measuring by flow cytometric analysis the positive rate (%) of MDSC (Gr-1+, CD11b+) in each type of peripheral blood collected at the time (immediately before euthanasia) of completion of an experiment of treatment with the full-length REIC/Dkk-3 protein (10 µg, 100 µg) or collected from a group treated with PBS buffer.

FIG. 17B-1 shows the result (cytogram) of measuring by flow cytometric analysis the positive rate of dendritic cells (CD11c+, CD80+) in each type of peripheral blood collected at the time (immediately before euthanasia) of completion of an experiment of treatment with the full-length REIC/Dkk-3 protein (10 µg, 100 µg) or collected from a group treated with PBS buffer. FIG. 17B-1a shows the result of using PBS, FIG. 17B-1b shows the result of using the full-length REIC/Dkk-3 protein (10 µg), and FIG. 17B-1c shows the result of using the full-length REIC/Dkk-3 protein (100 µg).

FIG. 17B-2 shows the result (graph of positive rates) of measuring by flow cytometric analysis the positive rate of dendritic cells (CD11c+, CD80+) in each type of peripheral blood collected at the time (immediately before euthanasia) of completion of an experiment of the treatment with full-length REIC/Dkk-3 protein (10 µg, 100 µg) or collected from a group treated with PBS buffer.

FIG. 17C-1 shows the result (cytogram) of measuring by flow cytometric analysis the positive rate of Treg (CD4+, Foxp3+) in each type of peripheral blood collected at the time (immediately before euthanasia) of completion of an experiment of treatment with the full-length REIC/Dkk-3 protein (10 µg, 100 µg) or from a group treated with PBS buffer. FIG. 17C-1a shows the result of using PBS, FIG. 17C-1b shows the result of using the full-length REIC/Dkk-3 protein (10 µg), and FIG. 17C-1c shows the result of using the full-length REIC/Dkk-3 protein (100 µg).

FIG. 17C-2 shows the result (graph of positive rates) of measuring by flow cytometric analysis the positive rate of Treg (CD4+, Foxp3+) in each type of peripheral blood collected at the time (immediately before euthanasia) of completion of an experiment of treatment with the full-length REIC/Dkk-3 protein (10 µg, 100 µg) or collected from a group treated with PBS buffer.

FIG. 17D-1 shows the result (cytogram) of measuring by flow cytometric analysis the positive rate of activated CTL (CD8+, CD69) in each type of peripheral blood collected at the time (immediately before euthanasia) of completion of an experiment of treatment with the full-length REIC/Dkk-3 protein (10 µg, 100 µg) or collected from a group treated with PBS buffer. FIG. 17D-1a shows the result of using PBS, FIG. 17D-1b shows the result of using the full-length REIC/Dkk-3 protein (10 µg), and FIG. 17D-1c shows the result of using the full-length REIC/Dkk-3 protein (100 µg).

FIG. 17D-2 shows the result (graph of positive rates) of measuring by flow cytometric analysis the positive rate of activated CTL (CD8+, CD69+) in each type of peripheral blood collected at the time (immediately before euthanasia) of completion of an experiment of treatment with the full-length REIC/Dkk-3 protein (10 µg, 100 µg) or collected from a group treated with PBS buffer.

FIG. 17E-1 shows the result (cytogram) of measuring by flow cytometric analysis the positive rate of NK cells (CD3e+, NK1.1+) in each type of peripheral blood collected at the time (immediately before euthanasia) of completion of an experiment of treatment with the full-length REIC/Dkk-3 protein (10 µg, 100 µg) or collected from a group treated with PBS buffer. FIG. 17E-1a shows the result of using PBS, FIG. 17E-1b shows the result of using the full-length REIC/Dkk-3 protein (10 µg), and FIG. 17E-1c shows the result of using the full-length REIC/Dkk-3 protein (100 µg).

FIG. 17E-2 shows the result (graph of positive rates) of measuring by flow cytometric analysis the positive rate of NK cells (CD3e+, NK1.1+) in each type of peripheral blood collected at the time (immediately before euthanasia) of completion of an experiment of treatment with the full-length REIC/Dkk-3 protein (10 µg, 100 µg) or collected from a group treated with PBS buffer.

In FIG. 18A, blue colonies indicate the presence of the interaction between the REIC/Dkk-3 protein and the Tctex-1 protein.

FIG. 20A shows the amino acid sequence alignment of a REIC/Dkk-3 protein with a TcTex-1 binding region of a dynein intermediate chain (DIC).

FIG. 20B shows the amino acid sequence alignment of the Tctex binding domain of the REIC/Dkk-3 protein with a known binding protein.

EMBODIMENTS FOR CARRYING OUT THE INVENTION

Figure 1:
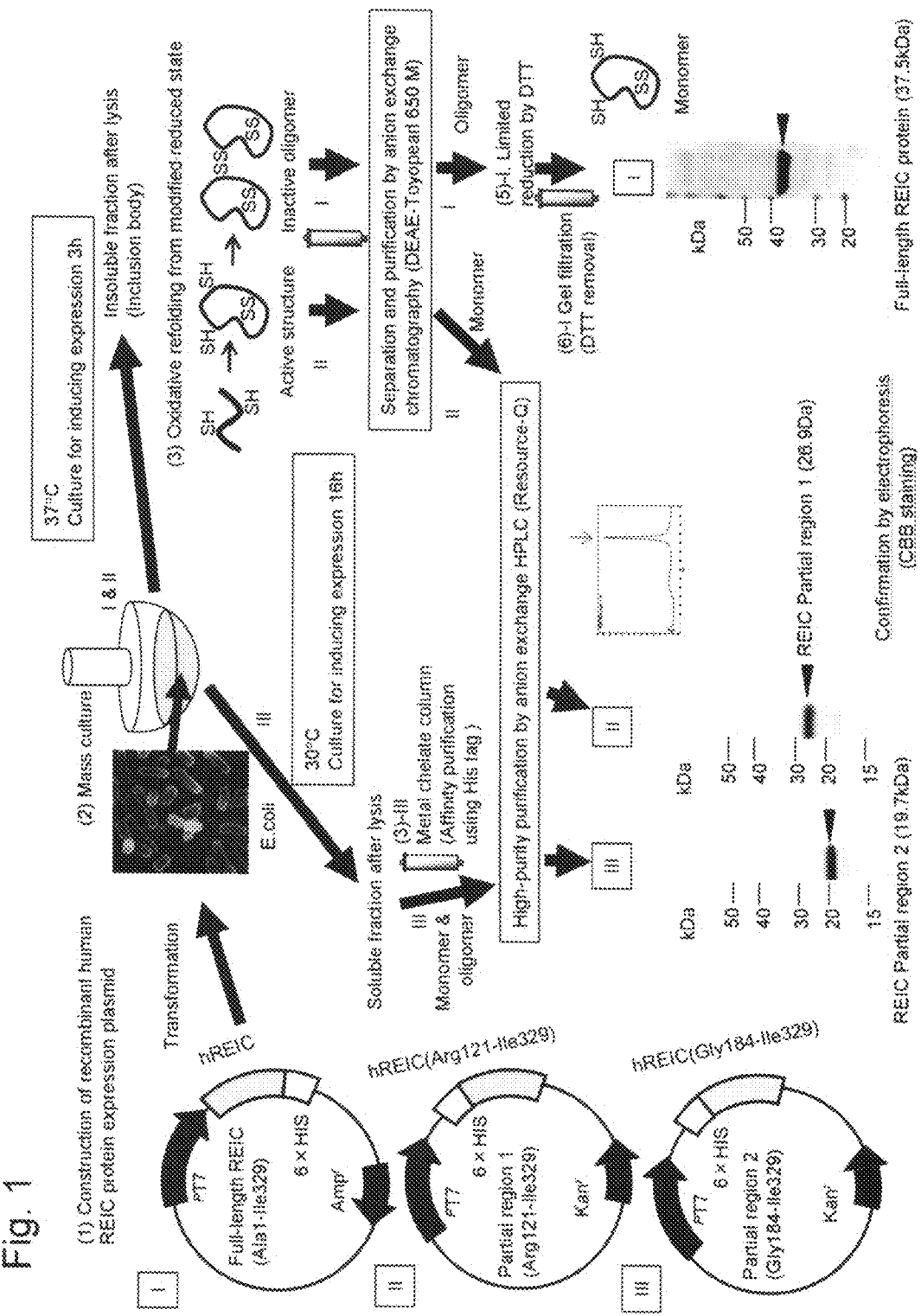
FIG. 1 shows a method for preparing the full-length human REIC/Dkk-3 protein and the partial regions 1 [Arg121-329] and 2 [Gly184-Ile329] thereof.

Hereafter, the present invention is described in detail.

The full-length nucleotide sequence of a REIC/Dkk-3 gene (REIC gene) and the amino acid sequence of the protein encoded by the gene are shown in SEQ ID NO: 1 and SEQ ID NO: 2, respectively. In the amino acid sequence shown in SEQ ID NO: 2, the sequence consisting of amino acids 1 to 21 is predicted to be a signal sequence. The REIC/Dkk-3 gene can be obtained from human cells, human tissues, and the like based on the sequence information of SEQ ID NO: 1. The REIC/Dkk-3 gene can also be obtained according to the International Publication WO01/038523 pamphlet.

Examples of the polypeptide consisting of a partial region of the REIC/Dkk-3 protein (REIC protein) of the present invention include the following polypeptides.

(1) A polypeptide consists of 209 amino acids containing the partial region consisting of Arg at position 121 to Ile at position 329 prepared by removing a signal sequence portion from the REIC/Dkk-3 protein. The polypeptide consists of Arg at position 142 to Ile at position 350 of the amino acid sequence shown in SEQ ID NO: 2. The polypeptide of the present invention may also be referred to as the partial region [Arg 121-Ile 329 (Arg at position 121-Ile at position 329] of the REIC/Dkk-3 protein. The amino acid sequence of the partial region [Arg 121-Ile 329] of the REIC/Dkk-3 protein of the present invention is shown in SEQ ID NO: 5 and the nucleotide sequence encoding the amino acid sequence is shown in SEQ ID NO: 6.

(2) A polypeptide consists of 146 amino acids containing the partial region consisting of Gly at position 184 to Ile at position 329 prepared by removing a signal sequence portion from the REIC/Dkk-3 protein. The polypeptide consists of Gly at position 205 to Ile at position 350 of the amino acid sequence shown in SEQ ID NO: 2. The polypeptide of the present invention may also be referred to as the partial region [Gly 184-Ile 329] of the REIC/Dkk-3 protein. The amino acid sequence of the partial region [Gly 184-Ile 329] of the REIC/Dkk-3 protein of the present invention is shown in SEQ ID NO: 3 and the nucleotide sequence encoding the amino acid sequence is shown in SEQ ID NO: 4.

(3) A polypeptide consists of 154 amino acids containing the partial region consisting of Ser at position 114 to Phe at position 267 prepared by removing a signal sequence portion from the REIC/Dkk-3 protein. The polypeptide consists of Ser at position 135 to Phe at position 288 of the amino acid sequence shown in SEQ ID NO: 2. The polypeptide of the present invention may also be referred to as the partial region [Ser 114-Phe 267] of the REIC/Dkk-3 protein. The amino acid sequence of the partial region [Ser 114-Phe 267] of the REIC/Dkk-3 protein of the present invention is shown in SEQ ID NO: 7 and the nucleotide sequence encoding the amino acid sequence is shown in SEQ ID NO: 8.

(4) The polypeptide consists of 83 amino acids containing the partial region consisting of Gly at position 184 to Phe at position 267 prepared by removing a signal sequence portion from the REIC/Dkk-3 protein. The polypeptide consists of the consensus sequence of the 3 above types of polypeptide, and is thought to play a core part of bioactivity. The polypeptide consists of Gly at position 205 to Phe at position 288 of the amino acid sequence shown in SEQ ID NO: 2. The polypeptide of the present invention may also be referred to as the partial region [Gly 184-Phe 267] of the REIC/Dkk-3 protein. The amino acid sequence of the partial region [Gly 184-Phe 267] of the REIC/Dkk-3 protein of the present invention is shown in SEQ ID NO: 9 and the nucleotide sequence encoding the amino acid sequence is shown in SEQ ID NO: 10.

(5) Another example of the polypeptide of the present invention consisting of a partial region of the REIC/Dkk-3 protein (REIC protein) is a polypeptide containing the partial region consisting of Gly at position 184 to Phe at position 267 prepared by removing a signal sequence portion from the REIC/Dkk-3 protein, and consists of a fragment of the partial region consisting of Ser at position 114 to Ile at position 329. The polypeptide contains the partial region consisting of Gly at position 205 to Phe at position 288 of the amino acid sequence shown in SEQ ID NO: 2, and consists of a fragment of the partial region consisting of Ser at position 135 to Ile at position 350 of the amino acid sequence shown in SEQ ID NO: 2. Also, the nucleotide sequence encoding the polypeptide contains the partial sequence consisting of g at position 613 to c at position 864 of the nucleotide sequence shown in SEQ ID NO: 1, and consists of a fragment of the partial sequence consisting of t at position 403 to t at position 1050 of the nucleotide sequence shown in SEQ ID NO: 1. The number of amino acid residues of the polypeptide ranges from 83 to 216.

Furthermore, the REIC/Dkk-3 protein interacts (association) with a Tctex-1 (t-complex testis expressed-1) protein to act. The Tctex-1 protein is a light chain protein (dynein light chain) composing a dynein motor complex, and plays an important role as an intervening molecule between the dynein motor and vesicular load through association with a Tctex-1 binding protein.

Both REIC/Dkk-3 protein and Tctex-1 protein are localized around the endoplasmic reticulum. The Tctex-1 protein accelerates the capacity of the REIC/Dkk-3 protein to induce apoptosis. The partial region of the REIC/Dkk-3 protein consists of 22 amino acids consisting of Val at position 136 to Met at position 157 of the amino acid sequence shown in SEQ ID NO: 2 and interacts with the Tctex-1 protein. The partial region polypeptide corresponds to the partial region consisting of Val at position 115 to Met at position 136 prepared by removing the signal sequence portion from the REIC/Dkk-3 protein. The amino acid sequence of the partial region is shown in SEQ ID NO: 17.

In the amino acid sequence of the partial region, EXGR-RXH (corresponds to the sequence consisting of amino acids 4 to 10 of SEQ ID NO: 18 and SEQ ID NO: 17) (X denotes an arbitrary natural amino acid) is a consensus sequence (consensus motif) involved in binding with the Tctex-1 protein.

The present invention encompasses the partial region peptide of the REIC/Dkk-3 protein interacting with the above Tctex-1 protein and the above consensus motif.

Therefore, an example of the polypeptide of the present invention consisting of a partial region of the REIC/Dkk-3 protein (REIC protein) is a polypeptide consisting of a partial region of the REIC/Dkk-3 protein, being capable of binding to the Tctex-1 protein, and consisting of the amino acid sequence shown in SEQ ID NO: 17. Another example thereof is a polypeptide consisting of 7 to 22 amino acid residues containing the sequence of the consensus motif shown in the above EXGRRXH (SEQ ID NO: 18). The polypeptide consists of continuous 7 to 22 amino acid residues in the amino acid sequence shown in SEQ ID NO: 17 and contains the amino acid sequence consisting of 7 amino acid residues of Glu at position 4 to His at position 10. In this case, Glu at position 5 and Ser at position 9 may be substituted with any other natural amino acids.

The partial region polypeptide of the REIC/Dkk-3 protein of the present invention contains the above amino acid sequence; that is, the amino acid sequence shown in SEQ ID NO: 3, SEQ ID NO: 5, SEQ ID NO: 7, or SEQ ID NO: 9, or the partial region consisting of Gly at position 184 to Phe at position 267 prepared by removing a signal sequence portion from the REIC/Dkk-3 protein, has the amino acid sequence of a polypeptide consisting of a fragment of the partial region consisting of Ser at position 114 to Ile at position 329 or an amino acid sequence substantially the same as the amino acid sequence, and has activity of inducing dendritic-cell-like cell differentiation. Also, the partial region polypeptide of the REIC/Dkk-3 protein of the present invention has the amino acid sequence shown in SEQ ID NO: 17 or an amino acid sequence substantially the same as the amino acid sequence, and has activity of binding to the Tctex-1 protein. Here, examples of such an amino acid sequence substantially the same as the above-mentioned amino acid sequence include: an amino acid sequence having a substitution, a deletion and/or an addition of 1 or a plurality of or several (1 to 10, preferably 1 to 5, and further preferably 1 or 2) amino acids with respect to the amino acid sequence, and an amino acid sequence having at least 85% or more, preferably 90% or more, further preferably 95% or more, and particularly preferably 97% or more identity with the amino acid sequence when calculated using BLAST (Basic Local Alignment Search Tool at the National Center for Biological Information (the basic local alignment search tool (BLAST) of the National Center for Biotechnology Information (NCBI))) or the like (e.g., using default; that is, initially set parameters).

The polypeptide of the present invention has activity of inducing dendritic-cell-like cell differentiation from monocytes, has activity of inducing the differentiation to immunoactivation cells such as CTL cells, NK cells, and helper T cells, and further has activity of suppressing MDSC and Treg cell differentiation. The polypeptide of the present invention has activity of inducing or suppressing differentiation to these cells, and thus it is able to inhibit the immunosuppression system. Therefore, the polypeptide of the present invention can be used as an anticancer immunostimulator, an anticancer agent, an antitumor agent, an agent for inducing or suppressing immune cell differentiation, or the like.

DNA encoding the partial region polypeptide of the REIC/Dkk-3 protein of the present invention encodes a protein having activity of: inducing dendritic-cell-like cell differentiation; inducing the differentiation to immunoactivation cells such as CTL cells, NK cells, and helper T cells; or suppressing MDSC and Treg cell differentiation, and is: DNA containing the nucleotide sequence shown in SEQ ID NO: 4, SEQ ID NO: 6, SEQ ID NO: 8, or SEQ ID NO: 10, the nucleotide sequence consisting of g at position 4 to g at position 69 of the nucleotide sequence shown in SEQ ID NO: 8, or the partial sequence consisting of g at position 613 to c at position 864 of the nucleotide sequence shown in SEQ ID NO: 1, and hybridizing under stringent conditions to DNA having a nucleotide sequence complementary to the nucleotide sequence consisting of a fragment of the partial sequence consisting of t at position 403 to t at position 1050 of the nucleotide sequence shown in SEQ ID NO: 1;

DNA containing the nucleotide sequence consisting of g at position 4 to g at position 69 of the nucleotide sequence shown in SEQ ID NO: 4, SEQ ID NO: 6, SEQ ID NO: 8, or SEQ ID NO: 10, or the partial sequence consisting of g at position 613 to c at position 864 of the nucleotide sequence shown in SEQ ID NO: 1, and having at least 85%, preferably 90% or more, further preferably 95% or more, and particularly preferably 97% or more identity with the nucleotide sequence consisting of a fragment of the partial sequence consisting of t at position 403 to t at position 1050 of the nucleotide sequence shown in SEQ ID NO: 1 when calculated using BLAST (Basic Local Alignment Search Tool at the National Center for Biological Information (the basic local alignment search tool (BLAST) of the National Center for Biotechnology Information (NCBI))) or the like (e.g., using default; that is, initially set parameters); or DNA encoding a protein consisting of an amino acid sequence having a substitution, a deletion and/or an addition of 1 or a plurality of or several (1 to 10, preferably 1 to 5, and further preferably 1 or 2) amino acids with respect to the amino acid sequence of the protein encoded by the above DNA. Here, the term "stringent conditions" refers to conditions of about "1×SSC, 0.1% SDS, and 37° C.," more stringent conditions refers to conditions of about "0.5×SSC, 0.1% SDS, and 42° C.," and further stringent conditions refers to conditions of about "0.2×SSC, 0.1% SDS, and 65° C."

A partial region polypeptide of the REIC/Dkk-3 protein can be obtained by chemical synthesis based on the above sequence information. Also, a partial region polypeptide of the REIC/Dkk-3 protein can be obtained as a recombinant polypeptide by a genetic engineering technique. Specifically, DNA encoding a partial region polypeptide of the REIC/Dkk-3 protein of the present invention is introduced into an appropriate vector, the vector is inserted into a host, the host is cultured, and then the polypeptide can be obtained from the culture product. Examples of a vector to be used for insertion of the DNA of the present invention are not particularly limited as long as it is replicable within a host and include plasmid DNA and phage DNA. Known vectors can be used herein. At this time, as hosts, eukaryotic cell lines or prokaryotic cell lines can be used. Examples of eukaryotic cells include animal cells such as established mammalian (e.g., human or rodent) cell lines, insect cell lines, fungal cells (e.g., filamentous cells) and yeast cells. Examples of prokaryotic cells include bacterial cells such as *Escherichia coli* cells. Host cells containing DNA encoding the partial region polypeptide of the REIC/Dkk-3 protein of the present invention are cultured in vitro or in vivo; that is, the host is cultured by a known method, so that a partial region polypeptide of the REIC/Dkk-3 protein can be obtained from the culture product. Here, the term "culture product" refers to any of a culture supernatant, cultured cells, cultured microorganisms, disrupted cells, and disrupted microorganisms. The thus expressed and produced polypeptide can be purified from the culture product. Purification may be performed by a general purification method employed for proteins. For example, purification can be performed by appropriately selecting and combining ion exchange chromatography, affinity chromatography, gel filtration, ultrafiltration, salting-out, dialysis, and the like. Moreover, the partial region polypeptide of the REIC/Dkk-3 protein of the present invention can also be obtained according to WO01/038523.

Among examples of the partial region polypeptide of the REIC/Dkk-3 protein of the present invention, particularly the partial region [Gly 184-Phe 267] of the REIC/Dkk-3 protein is stable such that it is not degraded even when stored at room temperature to an about high temperature of 37° C. The partial region polypeptide is also stable against various reagents such as PEG.

The present invention further encompasses a vector containing the above DNA encoding the partial region polypeptide of the REIC/Dkk-3 protein. The vector is introduced into a subject, the partial region polypeptide of the REIC/Dkk-3 protein is expressed in vivo within the subject, and thus the partial region polypeptide can exhibit bioactivity in vivo.

The partial region polypeptide of the REIC/Dkk-3 protein induces apoptosis in cancer cells.

In genetic therapy, the target gene (DNA) can be introduced into the subject in accordance with a known technique. Examples of techniques for introducing a gene into a subject include a method involving the use of a virus vector and a method involving the use of a non-virus vector. Various techniques are known (Bessatsu Jikken-Igaku, Idenshi-Chiryo-No-Kisogijutsu (Basic Techniques for Gene Therapy), Yodosha Co., Ltd., 1996; Bessatsu Jikken Igaku (Separate volume, Experimental Medicine), Idenshi donyu & hatsugen kaiseki jikken-hou (Experimentation of gene introduction & expression analysis), Yodosha, Co., Ltd. 1997; and the Japan Society of Gene Therapy (ed.), "Idenshi chiryo kaihatsu kenkyu handbook (the Handbook for research and development of gene therapy)," N.T.S., 1999).

Representative examples of virus vectors used for gene introduction include an adenovirus vector, an adeno-associated virus vector, and a retrovirus vector. A target gene may be introduced into a cell by introducing a target gene into a DNA or RNA virus, such as a detoxicated retrovirus, herpes virus, vaccinia virus, poxvirus, poliovirus, Sindbis virus, Sendai virus, SV40, or HIV, and infecting the cell with such virus.

When the gene according to the present invention is used for genetic therapy using a virus, an adenovirus vector is preferably used. An adenovirus vector is characterized in that: (1) it can introduce genes into many types of cells; (2) it can efficiently introduce genes into cells at the period of growth arrest; (3) it enables concentration via centrifugation to yield high-titer viruses (10 to 11 PFU/ml or more); and (4) it is suitable for direct gene introduction into tissue cells in vivo. As adenovirus vectors used for genetic therapy, a first-generation adenovirus vector lacking the E1/E3 region (Miyake, S. et al., Proc. Natl. Acad. Sci., U.S.A., 93, 1320, 1996), the second-generation adenovirus vector prepared from the first-generation adenovirus vector by deleting the E2 or E4 region in addition to the E1/E3 region (Lieber, A. et al., J. Virol., 70, 8944, 1996; Mizuguchi, H. & Kay, M. A., Hum. Gene Ther., 10, 2013, 1999), and the third-generation adenovirus vector lacking substantially all the adenovirus genome (GUTLESS) (Steinwaerder, D. S., et al., J. Virol., 73, 9303, 1999) have been developed. The gene according to the present invention can be introduced with the use of any of such adenovirus vectors without particular limitation. Further, the adeno-AAV hybrid vector to which the capacity for incorporating the gene into the AAV chromosome has been imparted (Recchia, A. et al., Proc. Natl. Acad. Sci., U.S.A., 96, 2615, 1999) or an adenovirus vector capable of incorporating the gene into the chromosome with the use of a transposon gene may be used, so that such vector can be applied to long-term gene expression. Also, a peptide sequence exhibiting tissue-specific transferability to the H1 loop of the adenovirus fiber may be inserted to impart tissue specificity to the adenovirus vector (Mizuguchi, H. & Hayakawa, T., Nippon Rinsho, 7, 1544, 2000).

Alternatively, the target gene can be introduced into a cell or tissue using a recombinant expression vector into which a gene expression vector, such as a plasmid vector, has been incorporated, without the use of the above viruses. For example, a gene can be introduced into a cell via lipofection, calcium phosphate coprecipitation, a DEAE-dextran method, or direct injection of DNA using a micro glass tube. Also, a recombinant expression vector can be incorporated into a cell via, for example, gene introduction using an internal liposome, gene introduction using an electorostatic type liposome, a method using HVJ-liposome, a method using a modified HVJ-liposome (i.e., the HVJ-AVE liposome method), a method using an HVJ-E (envelope) vector, receptor-mediated gene introduction, a method in which a particle gun is used to introduce DNA molecules in a cell with a carrier (i.e., a metal particle), direct introduction of naked-DNA, or gene introduction using various types of polymers. In such a case, any expression vector can be used, provided that such vector can express the target gene in vivo.

Examples of such vectors include pCAGGS (Gene 108, 193-200, 1991), pBK-CMV, pcDNA3, 1, and pZeoSV (Invitrogen, Stratagene), and pVAX1 vectors.

A vector comprising DNA encoding a partial region polypeptide of the REIC/Dkk-3 protein may adequately comprise a promoter or enhancer for transcribing the gene, poly A signal, a marker gene for labeling and/or selecting the cell into which the gene has been introduced, and the like. In such a case, a known promoter can be used.

A gene therapeutic agent containing DNA encoding a partial region polypeptide of the REIC/Dkk-3 protein of the present invention may be introduced into a subject by, for example, the in vivo method wherein a gene therapeutic agent is directly introduced into a body or the ex vivo method wherein a given cell is extracted from a human, a gene therapeutic agent is introduced into the cell ex vivo, and the cell is then returned into the body (Nikkei Science, April 1994, pp. 20-45; Gekkan Yakuji (Japan Medicine Monthly), 36(1), 23-48, 1994; Jikken igaku zoukan (special issue, Experimental Medicine), 12(15), 1994; the Japan Society of Gene Therapy (ed.), Idenshi chiryo kaihatsu kenkyu (Studies for Development of Gene Therapy) handbook, N. T. S., 1999).

The partial region polypeptide of the REIC/Dkk-3 protein, DNA encoding the polypeptide, and the vector containing the DNA of the present invention can be used as remedies or reagents.

The partial region polypeptide of the REIC/Dkk-3 protein of the present invention, DNA encoding the polypeptide, and a vector containing the DNA can induce dendritic-cell-like cell differentiation from monocytes, can enhance anticancer immune activity, and can be used for cancer treatment.

The partial region polypeptide of the REIC/Dkk-3 protein of the present invention, DNA encoding the polypeptide, and a vector containing the DNA can be used as agents for inducing dendritic-cell-like cell differentiation from monocytes, agents for activating cancer immunity, and pharmaceutical compositions having the effect of activating cancer immunity for cancer treatment or cancer prevention. Here, the term "activity of inducing dendritic-cell-like cell differentiation from monocytes" refers to activity of acting on monocytes to differentiate them into dendritic-cell-like cells. Whether or not dendritic-cell-like cell differentiation is induced by the addition of the partial region polypeptide of the REIC/Dkk-3 protein can be detected based on morphological features and surface antigens. Specifically, such features of the dendritic-cell-like cells are: the cells have morphologically dendrites; and the cells are found to be positive for dendritic cell markers, CD11c, CD40, CD80, CD86, and HLA-DR as surface antigens, as analyzed by flow cytometry.

Furthermore, a vector containing DNA encoding the partial region polypeptide of the REIC/Dkk-3 protein is introduced into a subject, the partial region polypeptide of the REIC/Dkk-3 protein is expressed in vivo within the subject, and thus the partial region polypeptide can exhibit an effect of inducing dendritic-cell-like cell differentiation from monocytes and an effect of treating or preventing cancer by the effect of activating cancer immunity and the action of activating cancer immunity.

Monocytes used in the present invention include peripheral blood-derived monocytes, bone marrow-derived monocytes, splenocyte-derived monocytes, and umbilical cord blood-derived monocytes. Of these, peripheral blood-derived monocytes are preferable. When specific monocytes such as CD14 positive monocytes are collected from a living body and induced by the partial region polypeptide of the REIC/Dkk-3 protein to differentiate into dendritic cell-like cells, such monocytes can be collected by an FACS (fluorescent activated cell sorter), a flow cytometer, or the like with the use of the presence of CD14 as an index. The animal species that is the origin of monocytes is not limited. Examples of animals that can be used include mammals such as mice, rats, guinea pigs, hamsters, rabbits, cats, dogs, sheep, pigs, bovines, horses, goats, monkeys, and humans. Isolation of a specific cell population by an FACS can be carried out by a known method. As an FACS or a flow cytometer, an FACS vantage (Becton, Dickinson and Company), an FACS Calibur (Becton, Dickinson and Company), or the like can be used, for example.

Monocytes can be cultured by a known technique for culturing human lymphoid cells. For a culture solution, for example, a known base medium such as RPMI1640 or DMEM can be used. Culture may be carried out by adding an appropriate antibiotic, animal serum, or the like to such base medium. Culture vessels used herein are not limited. Commercially available plates, dishes, and flasks can be adequately selected and used depending on the culture scale.

The present invention includes a method for culturing monocytes in vitro in the presence of the REIC protein and inducing dendritic cell-like cell differentiation from monocytes. In the method of the present invention, for example, culture may be carried out using monocytes at a concentration of $10^4$ to $10^7$ cells/ml with the addition of the partial region polypeptide of the REIC/Dkk-3 protein at a concentration of 1 to 20 µg/ml.

Dendritic cells play a very important role in the mechanisms of cancer immunity, inflammation, and the like in vivo. Dendritic cell-like cells induced to differentiate by the REIC/Dkk-3 protein according to the method of the present invention are morphologically similar to dendritic cells induced by IL-4+GM-CSF. However, to be exact, the dendritic cell-like cells differ from such dendritic cells, and therefore they are novel dendritic cell-like cells. Dendritic cell-like cells induced by the partial region polypeptide of the REIC/Dkk-3 protein are in dendritic forms. In addition, the dendritic cell-like cells are positive for dendritic cell markers such as CD11c, CD40, CD80, CD86, and HLA-DR. In this regard, novel dendritic cell-like cells of the present invention can be classified as dendritic cells. However, they are negative for CD1a, which is a dendritic cell marker, and positive for CD14, for which dendritic cells are generally supposed to be negative.

In the case of induction from CD14 positive monocytes with stimulation with the partial region polypeptide of the REIC/Dkk-3 protein, it refers to "dendritic cell-like differentiated cells that have been activated by the REIC protein (REIC activated monocytes with dendritic cell features)."

The partial region polypeptide of the REIC/Dkk-3 protein of the present invention has the capacity of inducing dendritic-cell-like cell differentiation higher than that of the full-length REIC/Dkk-3 protein.

The present invention encompasses dendritic cell-like cells induced from CD14 positive monocytes by the partial region polypeptide of the REIC/Dkk-3 protein.

Dendritic cell-like cells obtained via induction by the partial region polypeptide of the REIC/Dkk-3 protein can be used for cancer immunotherapy. Specifically, monocytes are collected from a subject, the monocytes are cultured with the partial region polypeptide of the REIC/Dkk-3 protein, the dendritic cell-like cells are induced, and then the obtained dendritic cell-like cells are returned to the subject. Thus, dendritic cell-like cells themselves can be used for cancer treatment or prevention, or the like. In such case, dendritic cell-like cells induced by the partial region polypeptide of the REIC/Dkk-3 protein act in a non-cancer-type-specific manner and exhibit cancer immunotherapeutic effects. However, it is also possible to add a cancer-type specific tumor antigen or an autologous tumor lysate upon induction of dendritic cell-like cells. In addition, induced dendritic cell-like cells can be cocultured with a specific tumor antigen or an autologous tumor lysate. It becomes possible to attack cancer cells in a tumor-specific manner by stimulating dendritic cell-like cells with a cancer-type-specific tumor antigen or an autologous tumor lysate.

Dendritic cell-like cells can be intradermally, subcutaneously, intravenously, or intralymphaticaly administered.

In addition, the partial region polypeptide of the REIC/Dkk-3 protein is thought to have a cytokine-like activity such that it acts on cells in an extracellular manner so as to control cell differentiation. Therefore, it is believed that the partial region polypeptide of the REIC/Dkk-3 protein widely functions in vivo in relation to immunity and inflammation. Thus, the partial region polypeptide of the REIC/Dkk-3 protein or DNA encoding the same can be administered to a subject as an agent for inducing differentiation into dendritic cell-like cells or an agent for activating dendritic cell-like cells for in vivo use. The partial region polypeptide of the REIC/Dkk-3 protein induces dendritic cell-like cells in a subject. As a result, the dendritic cell-like cells systematically activate lymphocytes having anticancer activity in the subject, resulting in the exhibition of cancer immune effects. Therefore, the partial region polypeptide of the REIC/Dkk-3 protein or DNA encoding the same can be used as an agent for activating cancer immunity. Further, since the partial region polypeptide of the REIC/Dkk-3 protein-induced dendritic cell-like cells have cancer immune effects, the partial region polypeptide of the REIC/Dkk-3 protein or DNA encoding the same can be used as a pharmaceutical composition for cancer treatment or prevention (a cancer immunotherapeutic agent). In such case, the partial region polypeptide of the REIC/Dkk-3 protein or DNA encoding the same may be administered alone. In this case, the effects are exhibited in a non-cancer-type-specific manner. Alternatively, it may be administered with a specific tumor antigen. In such a case, the effects can be exhibited in a cancer-type-specific manner.

Also, the REIC/Dkk-3 protein concentration in tissue in which canceration progresses is low, anticancer immune activity is unlikely to be induced in cancer tissue, so that the presence of cancer is not detected through the biological immunity (cancer cell immunological tolerance), resulting in proliferation or worsening of cancer. Under such circumstances, the partial region polypeptide of the REIC/Dkk-3 protein of the present invention is not only useful as a cancer therapeutic agent (an anticancer agent or an antitumor agent), but also useful as an agent for preventing canceration/carcinogenesis through anticancer immune activation. The partial region polypeptide is also useful as a cancer immunotherapeutic agent.

Furthermore, the partial region polypeptide of the REIC/Dkk-3 protein, DNA encoding the polypeptide, and a vector containing the DNA have activity of inducing the differentiation to immunoactivation cells such as CTL (cytotoxic T lymphocyte), NK (Natural killer) cells, and helper T cells, and activity of suppressing the differentiation to MDSC (myeloid derived suppressor cells: myelocyte-derived suppressor cells) and Treg cells (regulatory T cells). The polypeptide of the present invention can enhance anticancer immune activity, can be used for cancer treatment, and can exhibit anticancer effects on local and metastatic foci of cancer. Specifically, the polypeptide of the present invention can be used as an anticancer agent, an antitumor agent, an agent for activating anticancer immunity, an agent for potentiating systemic immunity or an agent for inducing the differentiation to immunoactivation cells, which involves accelerated induction of the differentiation to immunoactivation cells represented by dendritic cells, helper T cells, CTL, and NK cells, and as an agent for inhibiting the induction of differentiation to immunosuppressive cells represented by MDSC and Treg cells.

Examples of a cancer that is treated or prevented using the remedy of the present invention include cranial nerve tumor, skin cancer, gastric cancer, lung cancer, hepatic cancer, lymphoma/leukemia, colon cancer, pancreatic cancer, anal/rectal cancer, esophageal cancer, uterine cancer, breast cancer, adrenal cancer, kidney cancer, renal pelvic and ureteral cancer, bladder cancer, prostate cancer, urethral cancer, penile cancer, testicular cancer, osteoma/osteosarcoma, leiomyoma, rhabdomyoma, and mesoepithelioma. In particular, breast cancer and bladder cancer are preferable.

The remedy of the present invention contains DNA encoding the partial region polypeptide of the REIC/Dkk-3 protein, a vector containing the DNA, or the polypeptide encoded by the DNA, and a pharmacologically acceptable carrier, diluent, or excipient. The remedy of the present invention for cancer treatment or prevention can be administered in a variety of dosage forms. Examples of dosage forms include: tablets, capsules, granules, powders, and syrups for peroral administration; and injection preparations (e.g., for subcutaneous injection, intravenous injection, intramuscular injection, and intraperitoneal injection), drops, suppositories, spray, eye drops, transnasal preparations, transdermal preparations, transmucosal preparations, transpulmonary preparations, and adhesive preparations for parenteral administration.

The remedy of the present invention can also be used for systemic medication through injection or the like, or, can also be used for local administration. For example, the remedy is administered to a cancer site via injection, so as to be able to exhibit its effects. In particular, in the case of local administration of a vector containing DNA encoding the partial region polypeptide of the REIC/Dkk-3 protein, the peptide is produced by the vector for a long period of time at the cancer site, so as to be able to exhibit the effects.

Preferably, the remedy is directly injected locally to a cancer lesion once or multiple times so that the agent reaches all parts of the cancer lesion.

The remedy of the present invention comprises a carrier, a diluent, and an excipient that are generally used in the drug manufacturing field. For example, lactose or magnesium stearate can be used as a carrier or excipient of a tablet. Physiological saline or an isotonic solution containing glucose and another adjuvant is used as an aqueous solution of an injection, for example. Such an aqueous solution may be used in combination with an adequate solubilizer, such as alcohol, a polyalcohol such as propylene glycol, or a nonionic surfactant. Sesame oil, soybean oil, or the like is used as an oily liquid, and, as a solubilizer, benzyl benzoate, benzyl alcohol, or the like may be used in combination.

The dose varies depending on symptoms, age, body weight, and other conditions. In the case of the remedy, a dose may be 0.001 mg to 100 mg thereof at intervals of several days, several weeks, or several months, and it may be administered via subcutaneous injection, intramuscular injection, or intravenous injection. In the case of using a vector containing DNA encoding the partial region polypeptide of the REIC/Dkk-3 protein, $10^7$ to $10^9$ pfu (plaque forming unit) of the vector may be administered, for example.

The remedy of the present invention is also effective for a cancer patient having a cancer lesion confirmed to exhibit resistance to various existing treatments such as treatment with an anticancer agent.

The remedy of the present invention is confirmed to exhibit the effects of cancer cell death and/or tumor shrinkage even through single-agent administration thereof. Moreover, the combined use of this agent with an anticancer agent doubly induces anticancer effects, so that a strong tumor shrinkage effect can be expected.

Furthermore, the partial region polypeptide of the REIC/Dkk-3 protein of the present invention, DNA encoding the polypeptide, and a vector containing the DNA have anticancer immune activity, so that they can be used for: exhibiting therapeutic effects not only on a cancer lesion to which they are locally administered, but also on cancer metastatic foci; and preventing cancer metastasis.

Furthermore, simultaneous administration of various existing cancer antigen proteins, the partial region polypeptide of the REIC/Dkk-3 protein of the present invention, DNA encoding the polypeptide, and a vector containing the DNA, can cause systematic anticancer immune activation via the induction of differentiation into dendritic(-like) cells, allowing prevention of carcinogenesis itself.

The present invention is hereafter described in detail with reference to the following examples, although the present invention is not limited thereto.

Example 1

Preparation of Full-Length Human REIC/Dkk-3 Protein, and Partial Region 1 [Arg121-329] and Partial Region 2 [Gly184-Ile329] Thereof The full-length [Ala 1-Ile 329] sequence (sample I) (Ala 22 to Ile 350 of SEQ ID NO: 2) encoding a mature REIC/Dkk-3 protein and plasmid DNA encoding the REIC partial region [Arg 121-Ile 329] (sample II) of the REIC/Dkk-3 protein were transformed into *Escherichia coli* (T7 Express strain: NEB). About 10 fresh colonies were subjected to mass culture in a 1.6 liter of culture solution. IPTG (0.5 mM) was added to the culture solution (A600 to 0.7) at the logarithmic growth phase, so as to induce protein expression. Cells were cultured under expression induction conditions at 37° C. for 3 hours and then collected by centrifugation. The cells expressing proteins were lysed by ultrasonication or the like, centrifugation was performed, and then the thus expressed proteins were collected in an insoluble fraction. To remove *E. coli* cell-derived nucleic acids contaminating the insoluble fraction insofar as possible, 10 unit/mL Benzonase (Novagen) was added to the insoluble fraction dispersed in a buffer containing 20 mM Tris-HCl (pH8.0) and 5 mM MgCl$_2$, incubation was performed at 25° C. for 30 minutes, and thus nucleic acid degradation was accelerated. Subsequently, centrifugation was performed again, so that the insoluble fraction containing the high-purity REIC/Dkk-3 protein was obtained. Next, the precipitate thereof was suspended and dissolved well in Tris-HCl buffer (pH 8) containing 6 M guanidine hydrochloride, 100 mM 2-mercaptoethanol was added, incubation was performed at 37° C. for 1 hour, and thus the protein was completely reduced. At this time, protein quantification was performed by the Bradford method to determine the protein concentration. The resultant was diluted with a refolding buffer so that the final protein concentration was 0.2 mg/mL, followed by 24 hours of incubation at 25° C. The buffer (to be used at the time of refolding) containing 20 mM Tris-HCl, pH8.0, 0.4 M guanidine hydrochloride, and 30% glycerol, was prepared in advance to have a composition such that it contained oxidized glutathione (NACALAI TESQUE, INC.) in an amount (in terms of moles) ¼ that of 2-mercaptoethanol (contained in the reduced protein solution, so that it was introduced into the refolding buffer). The reduced protein solution was immediately diluted with the buffer having the aforementioned composition with stirring well using a stirrer. After refolding under the oxidation-reduction conditions, protein adsorption was performed using a column filled with an anion exchange resin (DEAE-Toyopearl 650 M, TOSOH CORPORATION). Elution was performed in 20 mM Tris-HCl buffer (pH 8.0) with a linear concentration gradient (0 to 0.8 M) of sodium chloride, and then the peak fraction of the REIC protein was collected at a sodium chloride concentration of about 0.5 M. At this time, full-length REIC [Ala 1-Ile 329] (sample I) was collected in the form of an oligomer with a disulfide (SS) bond formed between molecules. Accordingly, 30 mM dithiothreitol (DTT) was further added and then incubation was performed at 37° C. for 1 hour, thus resulting in a monomer in which intermolecular S—S bond alone was reduced to a limited extent. After this limited reduction reaction, the resultant was immediately equilibrated with phosphate buffer or MES buffer adjusted to have pH 6.0. DTT removal and buffer (pH 6.0) exchange were performed by Sephadex G25M column chromatography (GE HEALTHCARE), so that a sample that could be stably stored at 4° C. for several weeks was collected. The sample obtained at this stage is sample I. Sample I could be concentrated as necessary using a ultra-filtration filter through which only substances having a molecular weight of 10 kDa or less can pass.

With the above procedures, the REIC partial region [Arg 121-Ile 329] (sample II) was isolated as a stable monomer by anion exchange chromatography. To further perform high-purity purification, elution was performed by anion exchange HPLC using a Resource-Q column (GE HEALTHCARE) or the like and a linear concentration gradient of sodium chloride. Thus, the high-purity REIC partial region [Arg 121-Ile 329] of the REIC/Dkk-3 protein could be purified. The resultant was subjected to buffer exchange by Sephadex G25M column chromatography equilibrated with PBS (pH 7.4), so that sample II was obtained. Sample II could be concentrated as necessary using a ultrafiltration filter through which only substances having a molecular weight of 10 kDa or less can pass.

A protein encoding the partial region [Gly 184-Ile 329] (sample III) of the REIC/Dkk-3 protein was prepared as follows. Expression plasmid DNA was transformed into *Escherichia coli* (Shuffle T7 Express strain: NEB), and then about 10 fresh colonies were subjected to mass culture in a 0.8 liter of culture solution. IPTG (0.5 mM) was added to the culture solution (A600 to 0.7) at the logarithmic growth phase, so as to induce protein expression. Cells were cultured under expression induction conditions at 30° C. for 16 hours and then collected by centrifugation. The cells expressing proteins were lysed by ultrasonication or the like, centrifugation was performed, and then the thus expressed proteins were collected in a soluble fraction. In the REIC protein [Gly 184-Ile 329] used in this example, a His tag sequence was added to the N-terminal side. Thus, affinity purification was performed using TALON Metal Affinity Resin (Clontech). For further high-purity purification, the resultant was purified by anion exchange HPLC using a Resource-Q column (GE HEALTHCARE) or the like, and then subjected to buffer exchange by Sephadex G25M column chromatography equilibrated with PBS (pH 7.4), so that sample III was obtained.

The molecular weights inferred from the amino acid sequences were: 37.5 kDa in the case of the full-length REIC/Dkk-3 protein; 26.9 kDa in the case of the REIC/Dkk-3 protein partial region 1 [Arg 121-Ile 329], and 19.7 kDa in the case of the REIC/Dkk-3 protein partial region 2 [Gly 184-Ile 329]. Migration in the form of single bands toward molecular weights as inferred was confirmed by SDS-PAGE analysis.

The amino acid sequence of the full-length REIC/Dkk-3 protein is shown in SEQ ID NO: 2, the amino acid sequence of the REIC/Dkk-3 protein partial region 1 [Arg 121-Ile 329] is shown in SEQ ID NO: 5, and the amino acid sequence of the REIC/Dkk-3 protein partial region 2 [Gly 184-Ile 329] is shown in SEQ ID NO: 3. Furthermore, the sequence containing a His tag added to these sequences is shown in SEQ ID NO: 11. In addition, the amino acid sequence of the REIC/Dkk-3 protein partial region 1 [Arg 121-Ile 329] corresponds to amino acids 142 to 350 of the amino acid sequence shown in SEQ ID NO: 2.

FIG. 1 shows the outline of a method for preparing the full-length human REIC/Dkk-3 protein, the partial region 1 [Arg121-329], and the partial region 2 [Gly 184-Ile329] thereof.

Example 2

Induction of Dendritic Cell-Like Differentiation from Peripheral Blood Mononuclear Cell Preparation of Human Monocyte Human PBMCs (peripheral blood monocytes) were prepared from the blood of healthy donors by a standard method involving Ficoll-Paque centrifugation. The cell collection rate was determined by the trypan blue exclusion method. The survival rate was confirmed to be 99% or greater. For preparation of monocytes, PBMCs were resuspended in LGM-3 (serum-free lymphocyte growth medium-3; Lonza). The cells adhering to a plastic dish (subjected to incubation in a 10-cm dish at 37° C. for 2 hours) were used as monocytes. In some experiments, CD14+ monocytes were separated using CD14+ magnetic-activated cell sorting microbeads (MACS; MiltenyiBiotec). Purified CD14+ monocytes were resuspended in LGM-3 medium. Using flow cytometry, the purity was always found to exceed 95%.

Treatment of Human Monocytes

PBMCs were cultured alone (no addition), or cultured in the presence of GM-CSF (R&D Systems)+IL-4 (R&D Systems) (2 μg/ml each), the full-length human REIC/Dkk-3 protein, the partial region 1 [Arg 121-Ile 329], or the partial region 2 [Gly 184-Ile 329] (10 μg/ml) thereof prepared in Example 1. The cells were observed with a phase contrast microscope.

Figures 1, 5:
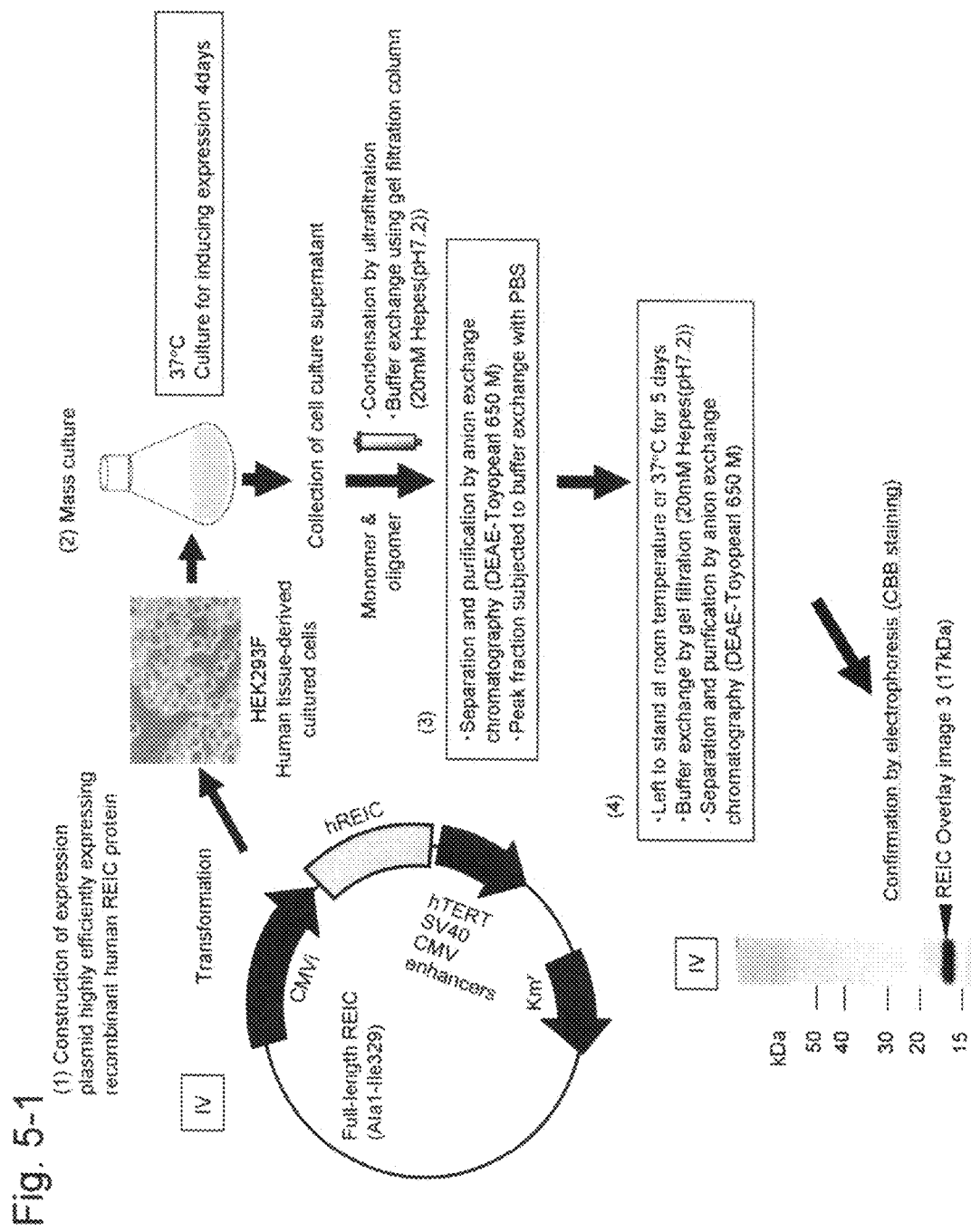
Figures 2, 5:
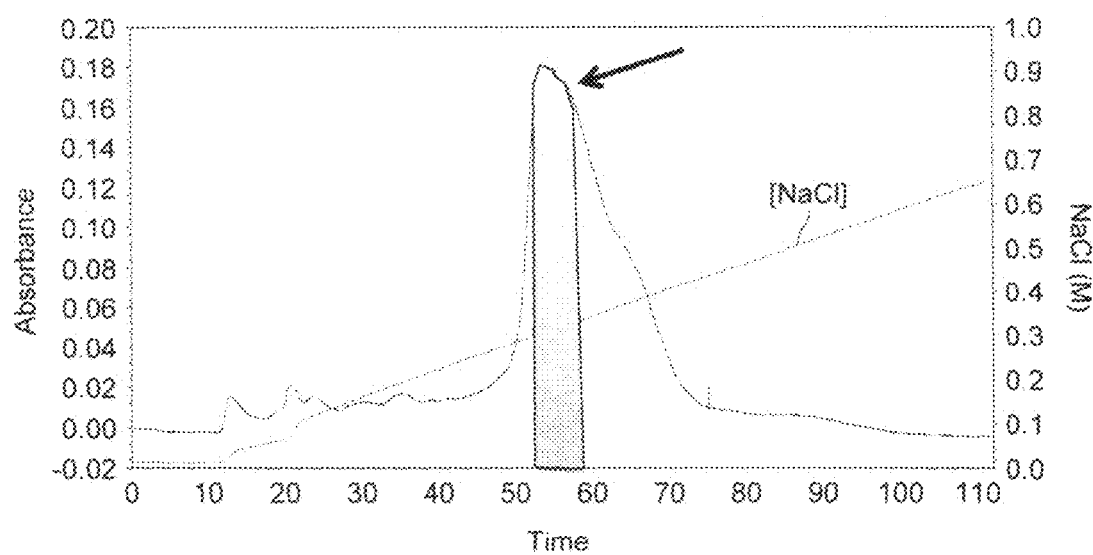

FIG. 2 shows the results of inducing dendritic cell-like differentiation on day 7 of culture in PBMCs cultured alone (no addition), or cultured in the presence of GM-CSF (R&D Systems)+IL-4 (R&D Systems) (2 μg/ml each), in the presence of the full-length human REIC/Dkk-3 protein, the partial region 1 [Arg 121-Ile 329], and the partial region 2 [Gly 184-Ile 329] (10 μg/ml) thereof prepared in Example 1. FIG. 2A shows the result of culturing PBMCs alone, FIG. 2B shows the result of adding GM-CSF+IL-4, FIG. 2C shows the result of adding the full-length REIC/Dkk-3 protein, FIG. 2D shows the result of adding the REIC/Dkk-3 protein partial region 1 [Arg 121-Ile 329], and FIG. 2E shows the result of adding the REIC/Dkk-3 protein partial region 2 [Gly184-Ile 329]. FIG. 2 shows slightly expanded phase contrast microscopic images.

As a result of morphological observation, the strongest activity of inducing dendritic-cell-like cell differentiation from peripheral blood mononuclear cells was observed in the case of the REIC/Dkk-3 protein partial region 2 [Gly 184-Ile 329].

Figures 3, 5:
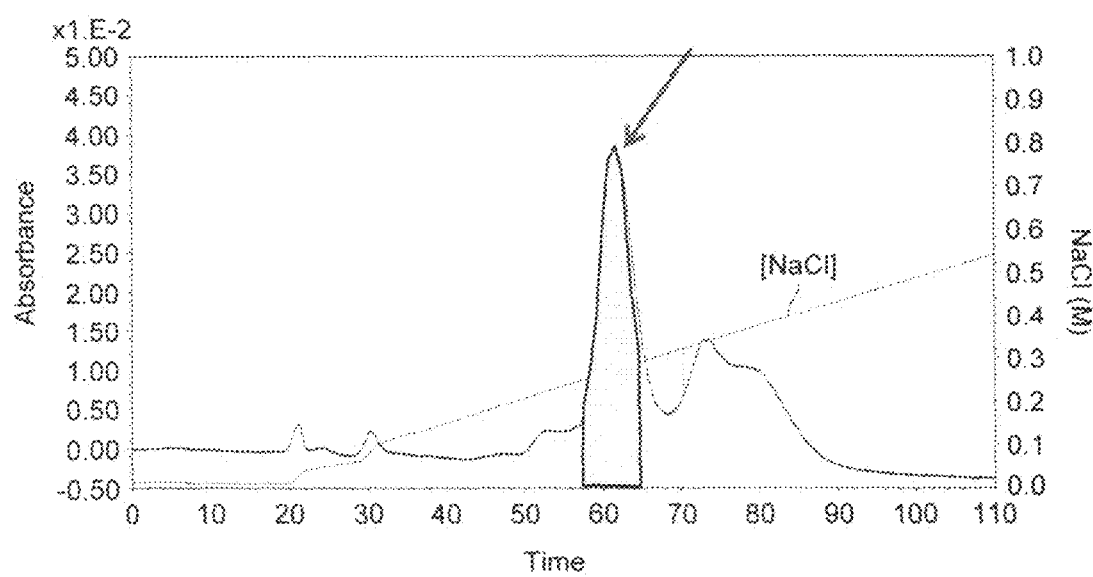

FIG. 3 shows the results of comparing differentiation induction in the case in which PBMCs alone was added, in the case in which GM-CSF+IL-4 was added, and in the case in which the REIC/Dkk-3 protein partial region 2 [Gly 184-Ile 329] was added. FIG. 3A shows the result of culturing PBMCs alone, FIG. 3B shows the result of adding GM-CSF+IL-4, FIG. 3C shows the result of adding the REIC/Dkk-3 protein partial region 2 [Gly 184-Ile 329]. FIG. 3 shows significantly expanded phase contrast microscopic images.

Dendritic-cell-like cells resulting from differentiation induction from peripheral blood mononuclear cells in the case in which the REIC/Dkk-3 protein partial region 2 had been added were morphologically smaller than dendritic cells induced with IL-4+GM-CSF. Meanwhile, no morphological difference was observed between dendritic-cell-like cells induced in the cases in which the full-length REIC/Dkk-3 protein and the REIC/Dkk-3 protein partial region 1 [Arg121-Ile329] had been added and dendritic-cell-like cells induced in the case in which the REIC/Dkk-3 protein partial region 2 had been added.

Figure 4:
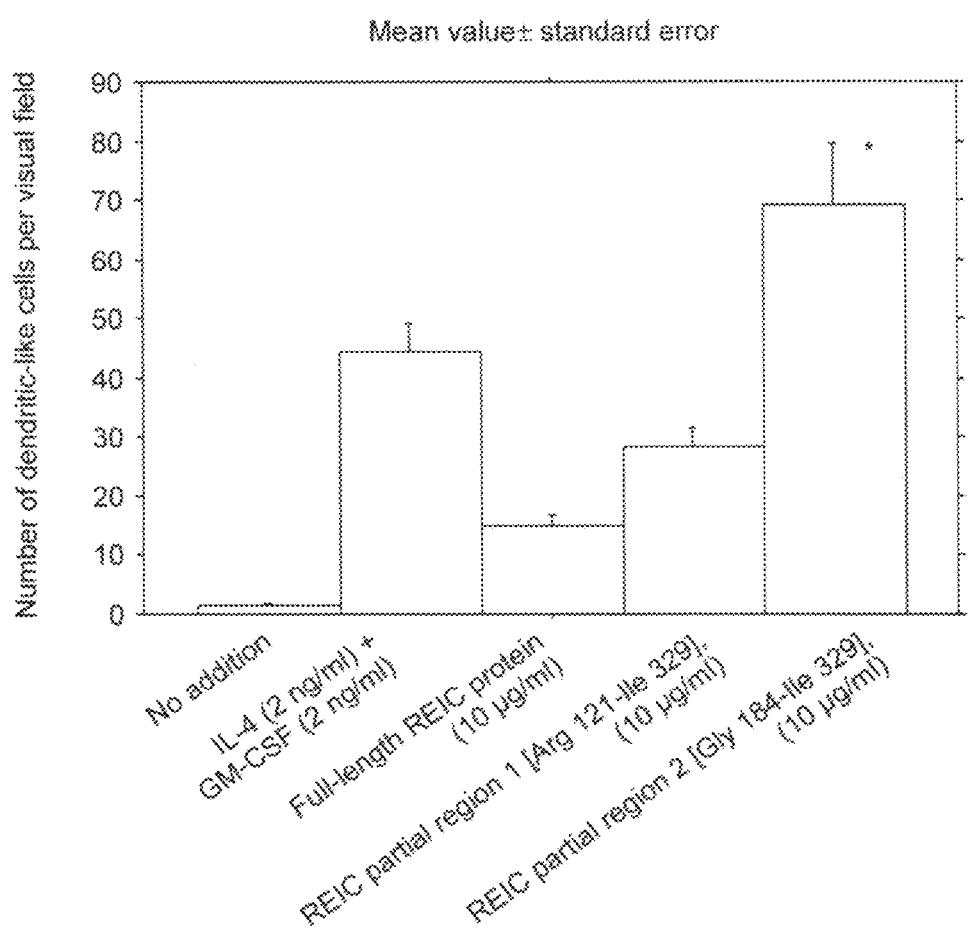
FIG. 4 shows the frequency of the occurrence of dendritic-cell-like cells resulting from differentiation induction in the presence of cells alone (no addition), GM-CSF+IL-4 (2 ng/ml each), the full-length human REIC/Dkk-3 protein, the partial region 1 [Arg 121-Ile 329], or the partial region 2 [Gly 184-Ile 329] (10 µg/ml).

FIG. 4 shows the frequency of the occurrence of dendritic-cell-like cells as a result of culturing PBMCs alone, adding GM-CSF (R&D Systems)+IL-4 (R&D Systems) (2 μg/ml each), adding the full-length human REIC/Dkk-3 protein, adding the partial region 1 [Arg 121-Ile 329], or adding the partial region 2 [Gly 184-Ile 329] (10 μg/ml). On Day 7, the resultants were stirred manually. Three (3) minutes later, the number of dendritic-cell-like cells per randomly-selected visual field was counted with the magnification of the slightly expanded photographs. The thus obtained data were converted into a graph (n=5 visual fields). As a result of morphological observation, the strongest activity of inducing dendritic-cell-like cell differentiation from peripheral blood mononuclear cells was observed in the case of the REIC/Dkk-3 protein partial region 2 [Gly 184-Ile 329]. The activity in the case in which the REIC/Dkk-3 protein partial region 2 [Gly 184-Ile 329] had been added was significantly stronger than that in the case in which the full-length REIC/Dkk-3 protein had been added and that in the case in which the partial region 1 [Arg 121-Ile 329] had been added. Furthermore, the activity in the case in which the REIC/Dkk-3 protein partial region 2 [Gly 184-Ile 329] had been added was also stronger than that in the case in which GM-CSF+IL-4 had been added.

Example 3

Preparation of the Partial Region 3 [Ser114-Phe267] of the Human REIC/Dkk-3 Protein As host cells for protein production, human kidney-derived cells FreeStyle 293-F cells (Invitrogen) at the logarithmic growth phase were used. Five (5) 500-mL flasks each containing 180 mL of a solution of the human kidney-derived cells with a concentration of 5 to 6×10⁵ cells/mL were prepared. Cells were cultured with shake (125 rpm)

over night at 37° C. in the presence of 8% $CO_2$ using Freestyle 293 Expression Media (Invitrogen). On the next day, each solution was adjusted to a concentration of $1\times10^6$ cells/mL. 180 μg each of a high expression plasmid (described below) encoding the full-length REIC [Ala1-Ile329] was mixed with 293 Fectin (Invitrogen) and then 180 mL of the solution of 293-F cells added to each 500-mL flask was transiently transfected with the mixture. After transfection, shake culture was performed for 4 days at 37° C. in the presence of 8% $CO_2$, and then culture supernatants were collected.

The thus collected culture supernatants were concentrated by ultrafiltration, the solvent was substituted with 20 mM Hepes Buffer (pH7.2) using Sephadex G25M column chromatography (GE HEALTHCARE), and then REIC protein-containing fractions were collected. Subsequently, protein adsorption was performed by anion exchange column chromatography (DEAE-Toyopearl 650M, TOSOH CORPORATION), and then elution was performed in 20 mM Hepes Buffer (pH7.2) with a linear concentration gradient (0 to 0.7M) of sodium chloride. Under conditions of the sodium chloride concentration of about 0.35 M, the peak fraction of the REIC protein was confirmed. The REIC protein was collected from a fraction containing the REIC protein, the number and the purity of which were higher than that contained in the peak fraction.

After buffer exchange with PBS using Sephadex G25M column chromatography equilibrated with PBS (pH7.4), followed by 5 days of incubation at 37° C. or room temperature, the full-length REIC [Ala1-Ile329] protein was subjected to limited proteolysis to result in the protein encoding the REIC partial region [Ser 114-Phe 267]. A protein solution containing the REIC partial region [Ser 114-Phe 267] was subjected to solvent substitution with 20 mM Hepes Buffer (pH7.2) by Sephadex G25M column chromatography (GE HEALTHCARE), so that a REIC protein-containing fraction was collected. Subsequently, protein adsorption was performed by anion exchange column chromatography (DEAE-Toyopearl 650M, TOSOH CORPORATION), and then elution was performed in 20 mM Hepes Buffer (pH7.2) with a linear concentration gradient (0 to 0.6 M) of sodium chloride. Under conditions of the sodium chloride concentration of about 0.3 M, the peak fraction of the REIC partial region [Ser 114-Phe 267] protein was confirmed. The REIC partial region [Ser 114-Phe 267] protein was collected from the peak fraction, so that sample IV was obtained. Sample IV was concentrated as necessary using an ultrafiltration filter through which substances having a molecular weight of 10 kDa or less can pass.

FIG. 5-1 shows preparation protocols. Also, FIG. 5-2 shows a chart (FIG. 5-1 (3) anion exchange chromatography) showing the result of the $1^{st}$ purification by anion exchange chromatography. FIG. 5-3 shows a chart (FIG. 5-1(4) anion exchange chromatography) showing the result of the $2^{nd}$ purification by anion exchange chromatography.

Figure 9:
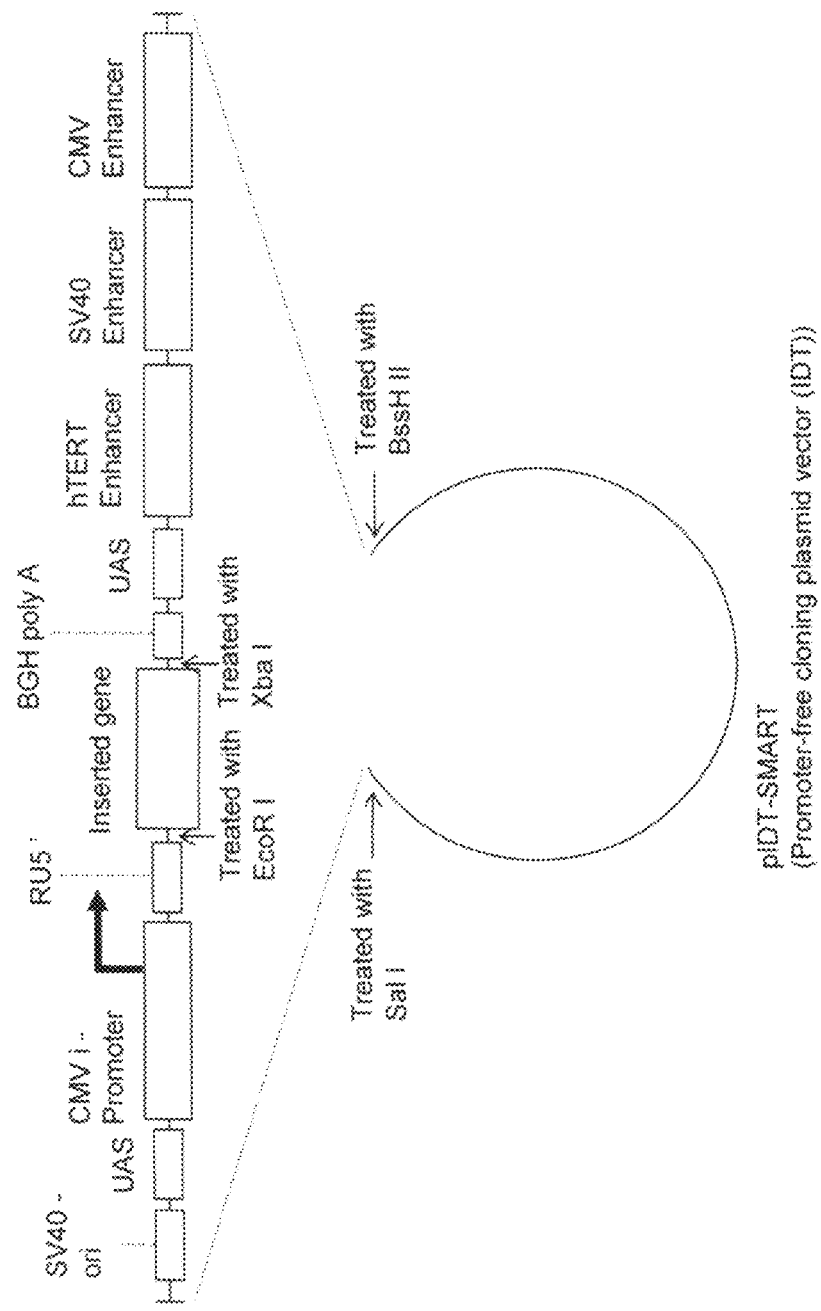
FIG. 9 shows the construct of an expression cassette contained in a high-level gene expression plasmid used in Example 3.

The high expression plasmid used in this example is a plasmid containing an expression cassette having a specific structure that enables mass production of a target protein (to be expressed by gene expression) through ultrahigh expression. The expression cassette has a structure in which a DNA construct containing the gene (to be expressed) of a protein (to be expressed) and a polyA addition sequence is located at least downstream of the $1^{st}$ promoter, and an enhancer or the $2^{nd}$ promoter is ligated downstream of the construct. At the farthest region downstream of the expression cassette, the above enhancer or the $2^{nd}$ promoter is present, and no other gene expression mechanisms are present downstream thereof. Specifically, the expression cassette to be used in the present invention has a structure in which at least a gene to be expressed is sandwiched between one $1^{st}$ promoter and at least one enhancer, or between one $1^{st}$ promoter and one $2^{nd}$ promoter. Here, the term "other gene expression mechanisms" refers to a mechanism for expressing genes other than a gene to be expressed. As a promoter, a CMVi promoter, an SV40 promoter, an hTERT promoter, a β actin promoter, or a CAG promoter can be used. As an enhancer, a CMV enhancer, an SV40 enhancer, or an hTERT enhancer can be used. Furthermore, DNA encoding a protein to be expressed may be ligated downstream of a promoter, and 1 to 4 CMV enhancers may be ligated upstream of a DNA construct containing a polyA addition sequence. Moreover, (i) RU5' ligated immediately upstream of DNA encoding a foreign protein, (ii) UAS ligated immediately upstream of an enhancer and/or promoter, or (iii) SV40-ori ligated to the farthest region upstream of an expression cassette may also be contained. FIG. 9 shows the construct of an expression cassette contained in the plasmid used herein.

Example 4

Induction of Dendritic Cell-Like Differentiation from Peripheral Blood Mononuclear Cells by the Partial Region 3 [Ser114-Phe267] of the Human REIC/Dkk-3 Protein With the method described in Example 2, human PBMCs (peripheral blood monocytes) were prepared and then cultured alone (no addition), cultured in the presence of the full-length human REIC/Dkk-3 protein, cultured in the presence of the partial region 1 [Arg 121-Ile 329] thereof prepared in Example 1, or cultured in the presence of the partial region 3 [Ser114-Phe267] (10 μg/ml) prepared in Example 3. Cells were observed with a phase-contrast microscope.

Figure 6C:
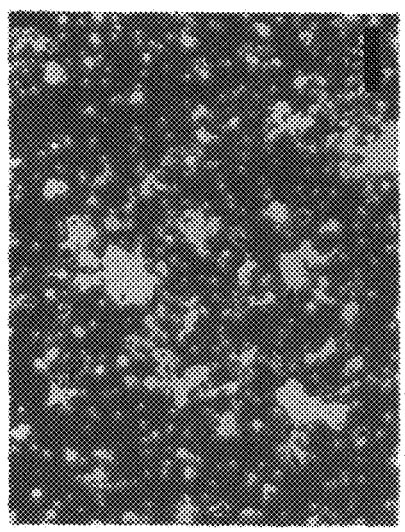
FIG. 6 shows photographs showing the induction of dendritic cell-like differentiation from peripheral blood monocytes through the addition of a human REIC protein expressed by human tissue-derived cultured cells. Specifically, these photographs are slightly expanded phase-contrast microscopic images of dendritic-cell-like cells (on day 7) resulting from differentiation induction with the presence of cells alone (no addition) (FIG. 6A), the presence of the partial region 1 [Arg 121-Ile 329] (10 µg/ml) (FIG. 6B) or the partial region 3 [Ser 114-Phe 267] (10 µg/ml) (FIG. 6C) of the REIC/Dkk-3 protein.
Figure 6B:
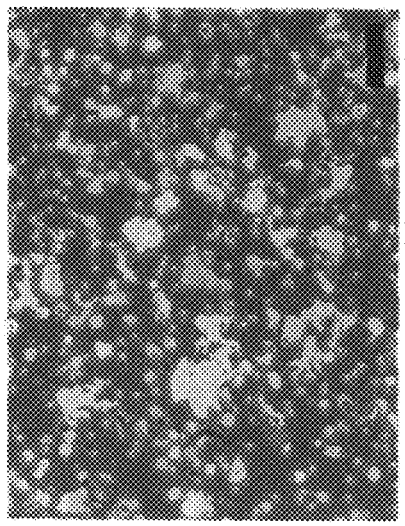
Figure 6A:
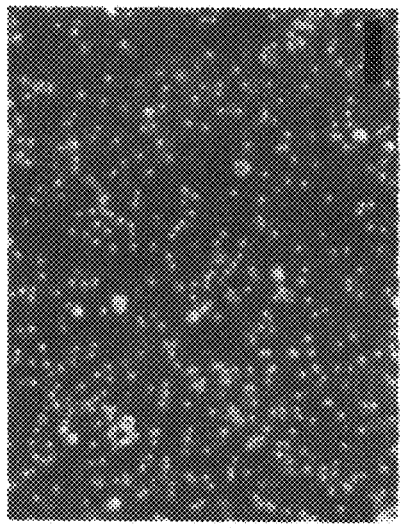

FIG. 6 shows the results of inducing dendritic cell-like differentiation on Day 7 of culture in PBMCs cultured alone (no addition), cultured in the presence of the full-length human REIC/Dkk-3 protein prepared in Example 1, and cultured in the presence of the partial region 3 [Ser114-Phe267] (10 μg/ml) prepared in Example 3, respectively. FIG. 6A shows the result of culturing PBMCs alone, FIG. 6B shows the result of adding the full-length REIC/Dkk-3 protein, FIG. 6C shows the result of adding the REIC/Dkk-3 protein partial region 3 [Ser114-Phe267]. FIG. 6 shows slightly expanded phase contrast microscopic images. As a result of morphological observation, in the case of the REIC/Dkk-3 partial region 3, activity of inducing dendritic-cell-like cell differentiation from peripheral blood mononuclear cells equivalent to or higher than that in the case of the full-length REIC/Dkk-3 protein or the partial region 1 thereof was observed. FIG. 7 shows significantly expanded images. As shown in FIG. 7, no morphological difference was observed in dendritic-cell-like cells resulting from differentiation induction from peripheral blood mononuclear cells between the case of REIC/Dkk-3 partial region 3 and the case of partial region 1.

Example 5

Stability of REIC/Dkk-3 Partial Region 3

Figure 8:
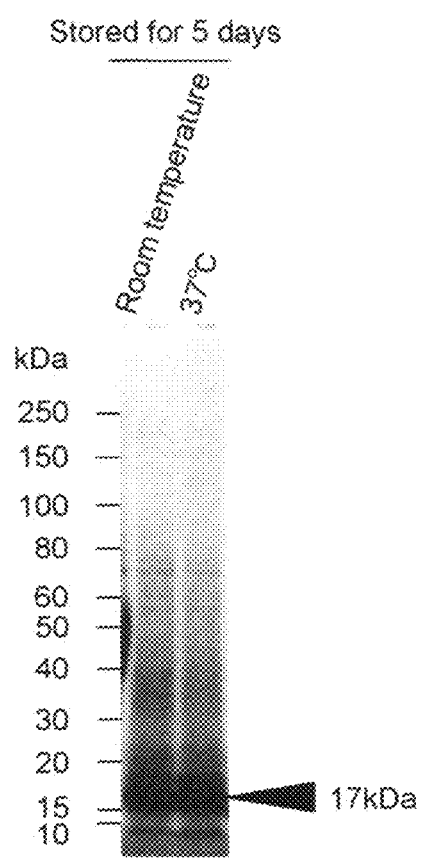
FIG. 8 shows the result of an experiment for confirming the stability of the partial region 3 [Ser 114-Phe 267] of a REIC/Dkk-3 protein.

After 5 days of incubation at 37° C. or room temperature (about 20° C.), 18 μL of each sample was separated using SDS-PAGE. The protein encoding the REIC/Dkk-3 partial region 3 having a molecular weight of about 17 kDa was detected by CBB staining. At this time, each sample was left to stand at room temperature (about 20° C.) or 37° C. for 5 days, and then subjected to SDS-PAGE, so that the degradation pattern was confirmed. FIG. 8 shows the result of SDS-PAGE. Regardless of a temperature that was too high for protein storage conditions, the partial region 3 was detected by CBB staining as a band of about 17 kDa after SDS-PAGE separation.

Furthermore, it was demonstrated that in the case of the protein solution of the partial region 3, no reactions were observed such as aggregation and precipitation even when salts (e.g., various PEGs, ammonium sulphide, and lithium sulfide) or alcohols (e.g., 2-methyl-2,4-pentandiol (MPD), ethanol, and 2-propanol) had been added and mixed therewith. Thus, it was revealed that the partial region 3 had sufficiently high stability.

Example 6

Figure 10:
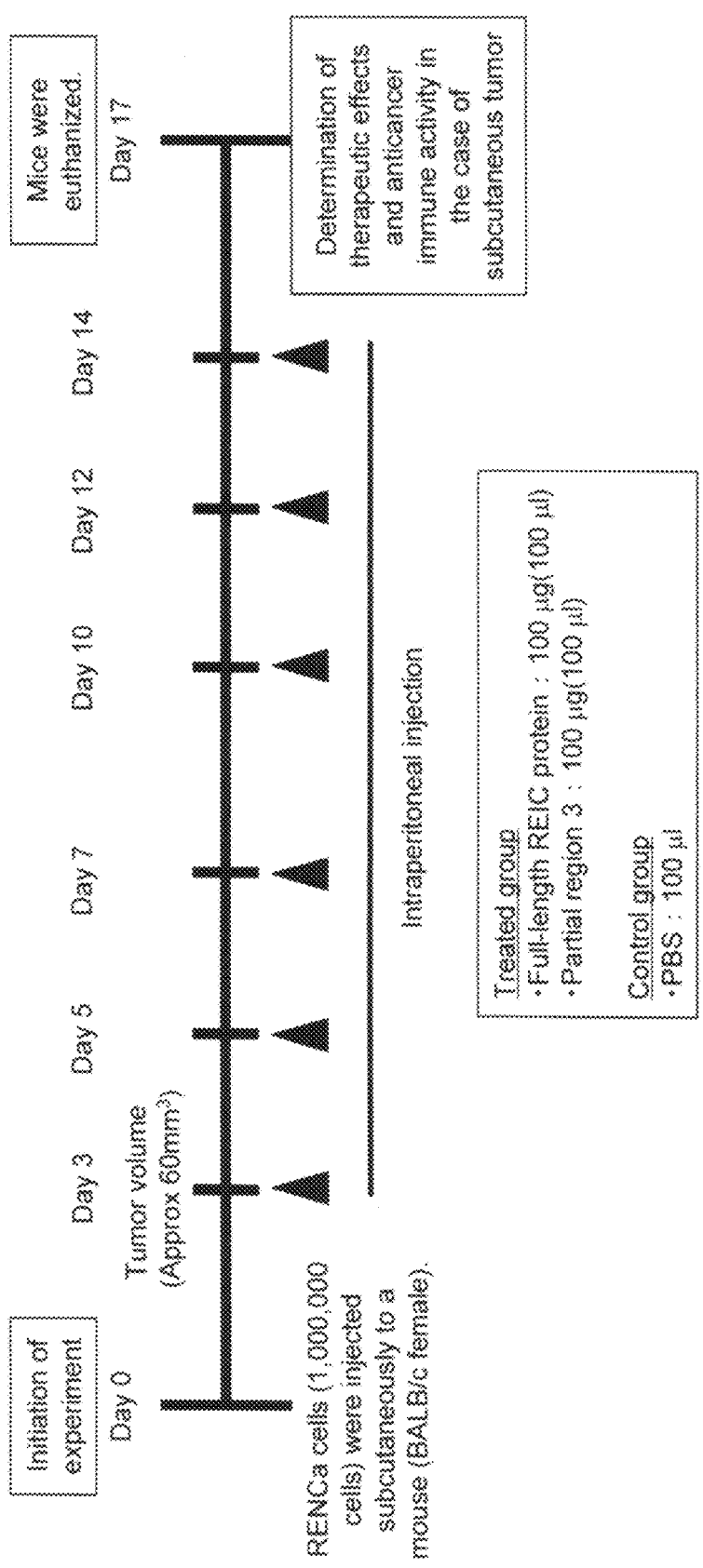
FIG. 10 shows protocols for an experiment of the intraperitoneal administration of the human full-length REIC/Dkk-3 protein and the partial region 3 [Ser 114-Phe 267].

Determination of Tumor-Suppressive Effects of the Partial Region 3 [Ser 114-Phe 267] of the REIC/Dkk-3 Protein in In Vivo Experiments RENCa cells ($1 \times 10^6$) were subcutaneously injected into mice (BALB/c, female, n=5). On Days 3, 5, 7, 10, 12, and 14 after injection (provided that Day 3 after injection was designated as the day of the start of administration of the full-length REIC protein and the partial region 3), the full-length REIC protein (100 µg (100 µl)) or the partial region 3 (100 µg (100 µl)) or PBS (100 µl) as a control was intraperitoneally injected into mice. On Day 17, therapeutic effects in subcutaneous tumors were determined, anticancer immune activity was measured (Example 7), and then mice were euthanized. FIG. 10 shows in vivo experimental protocols. Tumor volume was obtained by the following formula: 0.52×(minimum diameter)$^2$×(maximum diameter).

Figure 11A:
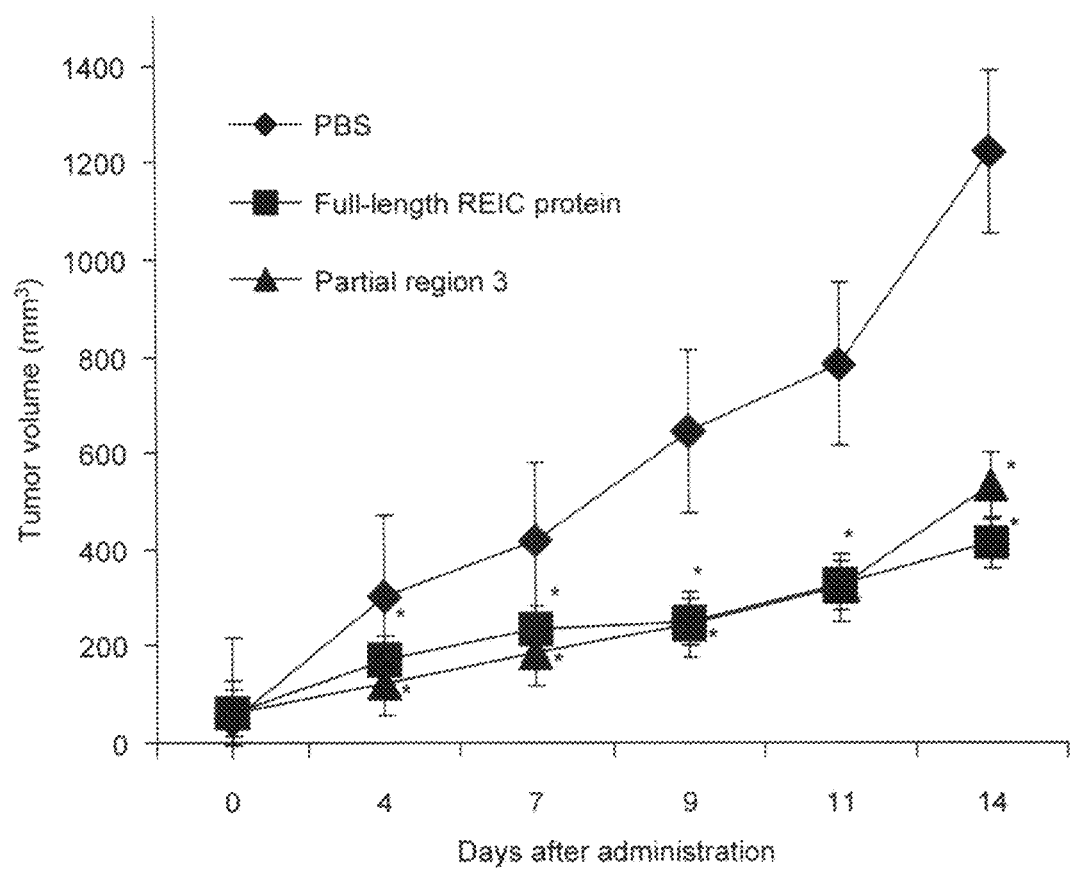
FIG. 11A shows the effects of suppressing tumor growth (changes over time in tumor volume) due to intraperitoneal administration of the human full-length REIC/Dkk-3 protein and the partial region 3 [Ser 114-Phe 267].
Figure 11B:
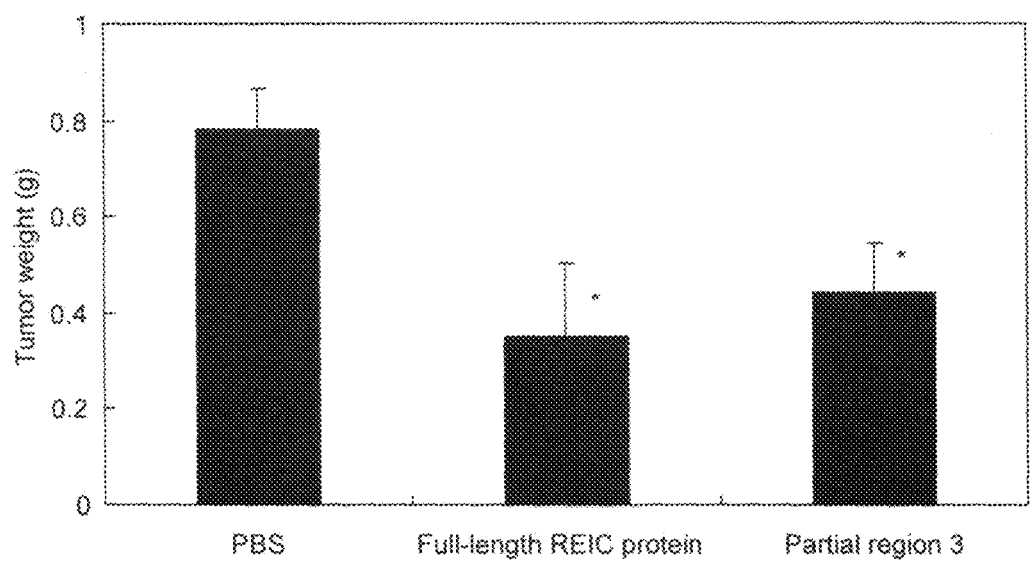
FIG. 11B shows the effects of suppressing tumor growth (tumor weight) due to the intraperitoneal administration of the human full-length REIC/Dkk-3 protein and the partial region 3 [Ser 114-Phe 267].
Figure 11C:
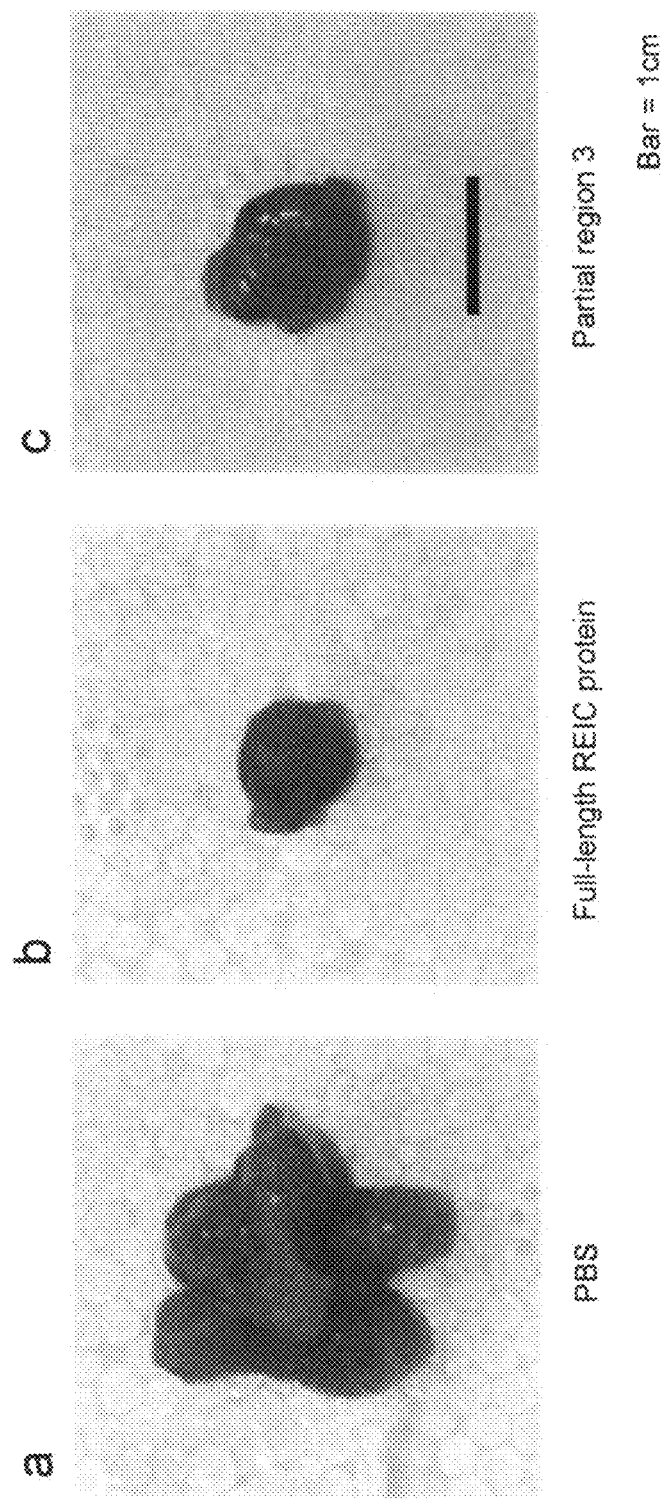
FIG. 11C shows photographs showing tumors exhibiting the effects of suppressing tumor growth due to the intraperitoneal administration of the human full-length REIC/Dkk-3 protein and the partial region 3 [Ser 114-Phe 267].

FIG. 11A shows changes over time in tumor volume after treatment. The tumor volumes of the group treated with the full-length REIC protein or treated with the partial region 3 and the group to which PBS as a control had been administered were compared. As a result, differences were found to be statistically significantly small (indicated with *). FIG. 11B shows the weights of tumors collected from mice. The tumor weights of the group treated with the full-length REIC protein or the partial region 3 and the group to which PBS had been administered were compared. As a result, differences were found to be statistically significantly small (indicated with *). FIG. 11C shows photographs of tumors collected from mice. As shown in FIG. 11A to FIG. 11C, tumor growth could be suppressed through administration of the full-length REIC protein and the partial region 3.

Example 7

Flow Cytometry of the Immunocompetent Cells in Mouse Venous Blood of Example 6

Changes in the number of the immunocompetent cells existing in mouse venous blood obtained in Example 6 were analyzed by flow cytometry. 0.2% EDTA solution (30 µl) was added to 750 µl of mouse blood collected from inferior vena cava for anticoagulation. Each of the following antibodies (1 µl each) fluorescently labeled differently (purchased from eBioscience) was added to 30 µl of blood. The resultants were stirred and then incubated at 4° C. for 60 minutes, so that the following immunocompetent cells were stained.

Bone marrow-derived immunosuppression cells (anti-GR-1 antibody, anti-CD11b antibody)
Dendritic cells (anti-CD11 antibody)
Activated dendritic cells (CD11c+/CD80+) (anti-CD11c antibody, anti-CD80 antibody)
Activated dendritic cells (CD11c+/CD86+) (anti-CD11c antibody, anti-CD86 antibody)
Helper T cells (anti-CD4 antibody)
Immunoregulatory T cells (anti-CD4 antibody, anti-Foxp3 antibody)
Cytotoxic T cells (anti-CD8 antibody)
Activated cytotoxic T cells (anti-CD69 antibody, anti-CD8 antibody)
NK cells (anti-CD3e antibody, anti-NK1.1 antibody)

Figure 12B:
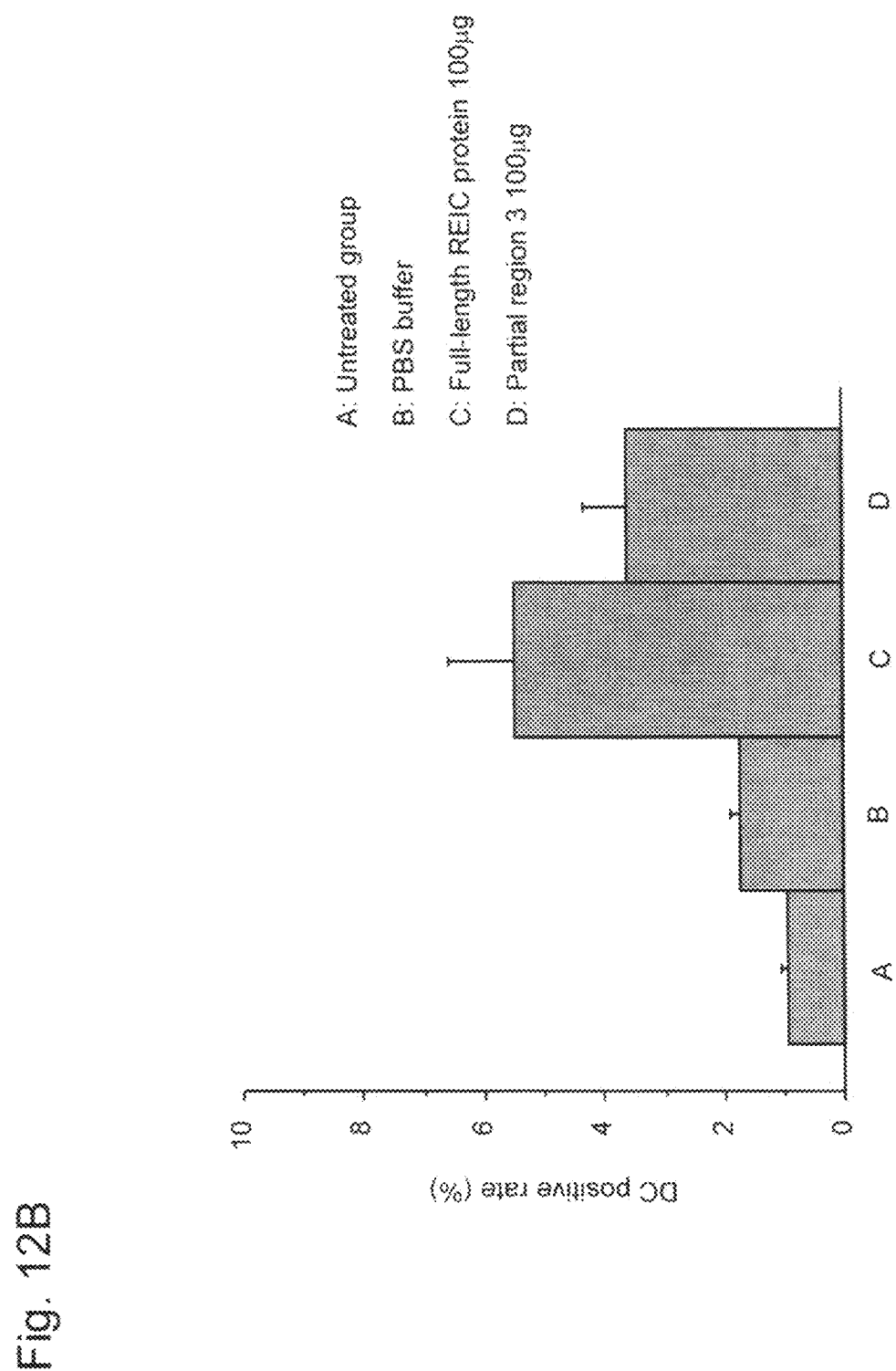
FIG. 12B is a graph showing the positive rate (%) of dendritic cells in each type of peripheral blood at the time (immediately before euthanasia) of completion of an experiment of treatment with the REIC/Dkk-3 protein (full-length or partial region 3), in an untreated group, or in a group treated with PBS buffer.
Figure 12C:
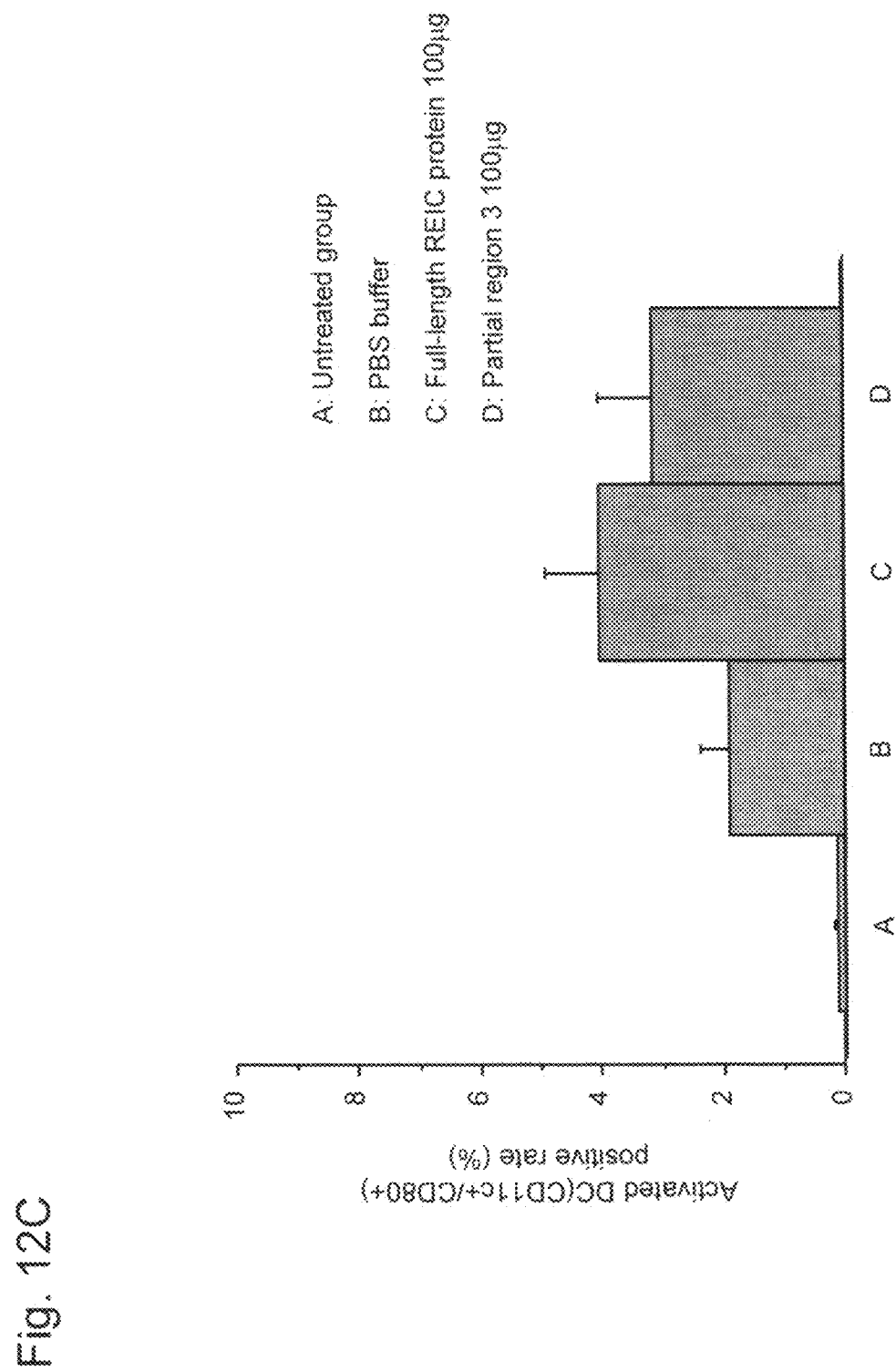
FIG. 12C is a graph showing the positive rate (%) of activated dendritic cells (CD11c+/CD80+) in each type of peripheral blood at the time (immediately before euthanasia) of completion of an experiment of treatment with the REIC/Dkk-3 protein (full-length or partial region 3), in an untreated group, or in a group treated with PBS buffer.
Figure 12D:
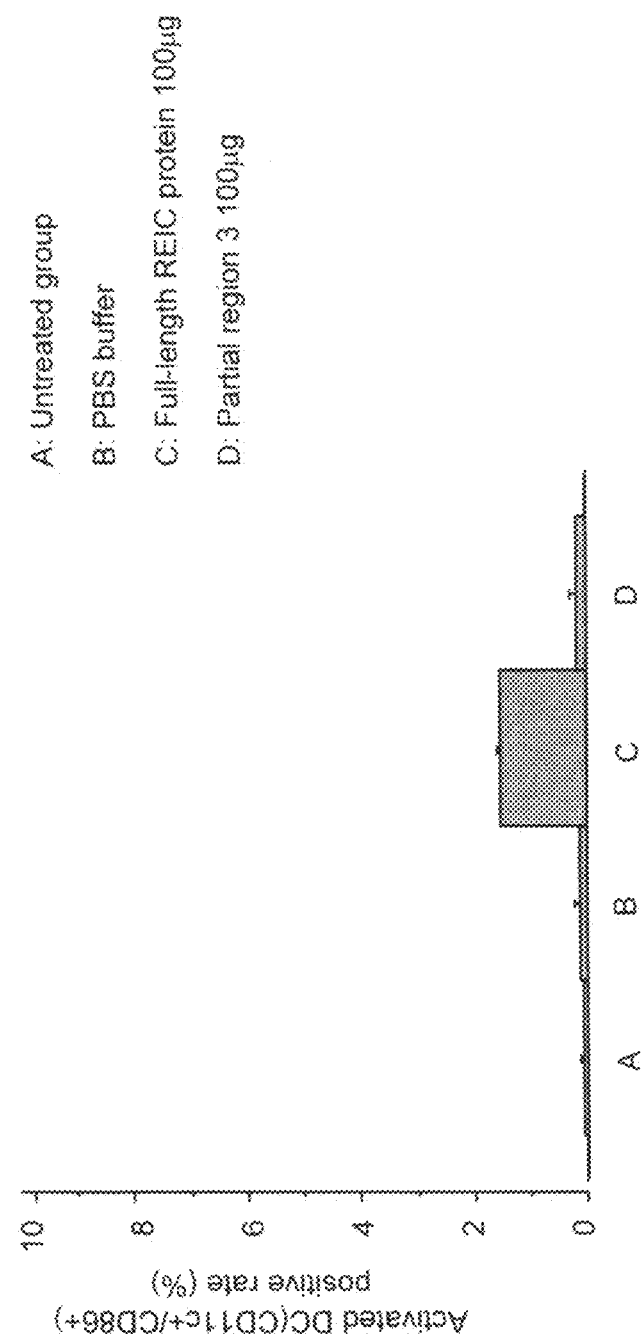
FIG. 12D is a graph showing the positive rate (%) of activated dendritic cells (CD11c+/CD86+) in each type of peripheral blood at the time (immediately before euthanasia) of completion of an experiment of treatment with the REIC/Dkk-3 protein (full-length or partial region 3), in an untreated group, or in a group treated with PBS buffer.
Figure 12E:
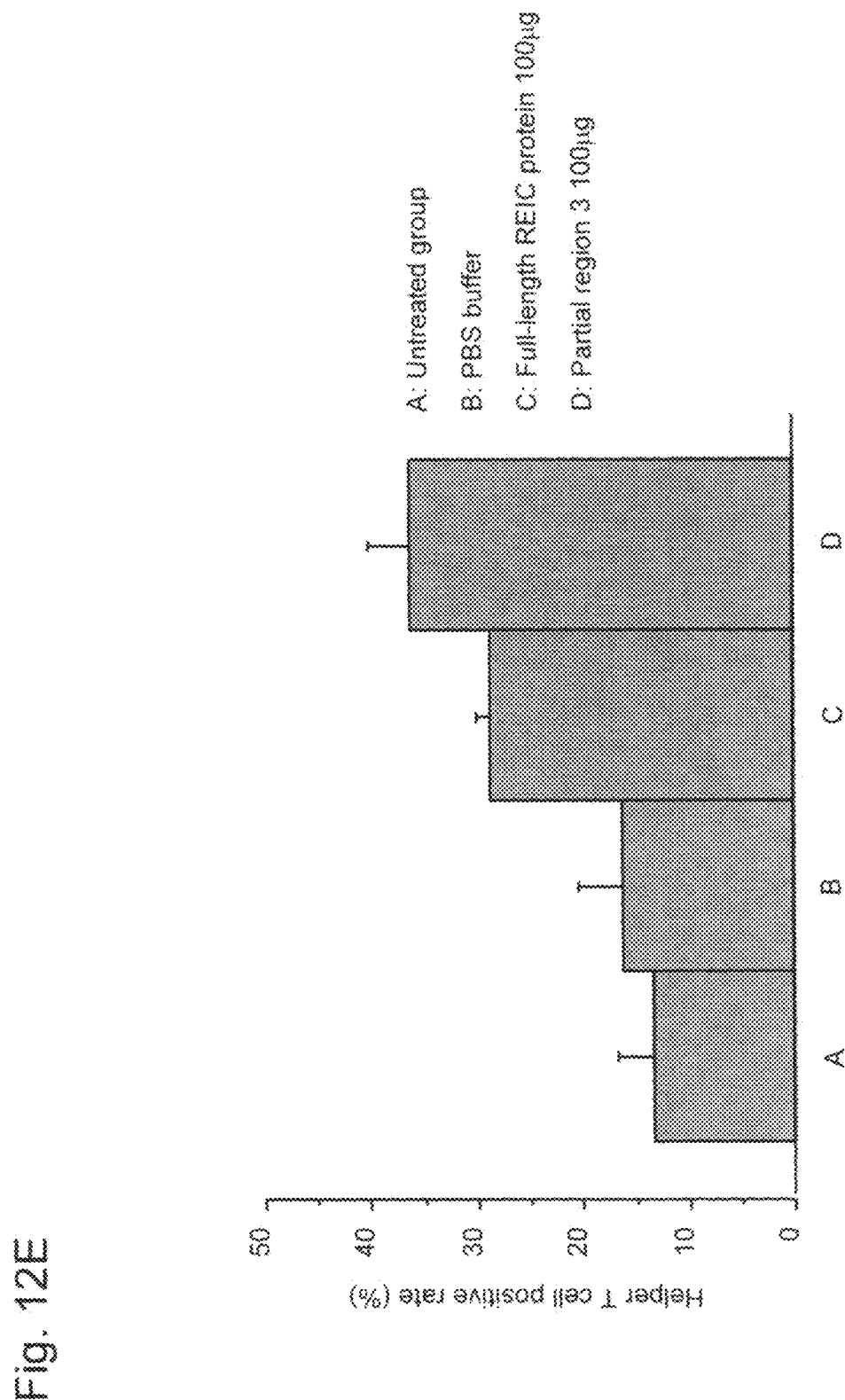
FIG. 12E is a graph showing the positive rate (%) of helper T cells in each type of peripheral blood at the time (immediately before euthanasia) of completion of an experiment of treatment with the REIC/Dkk-3 protein (full-length or partial region 3), in an untreated group, or in a group treated with PBS buffer.
Figure 12F:
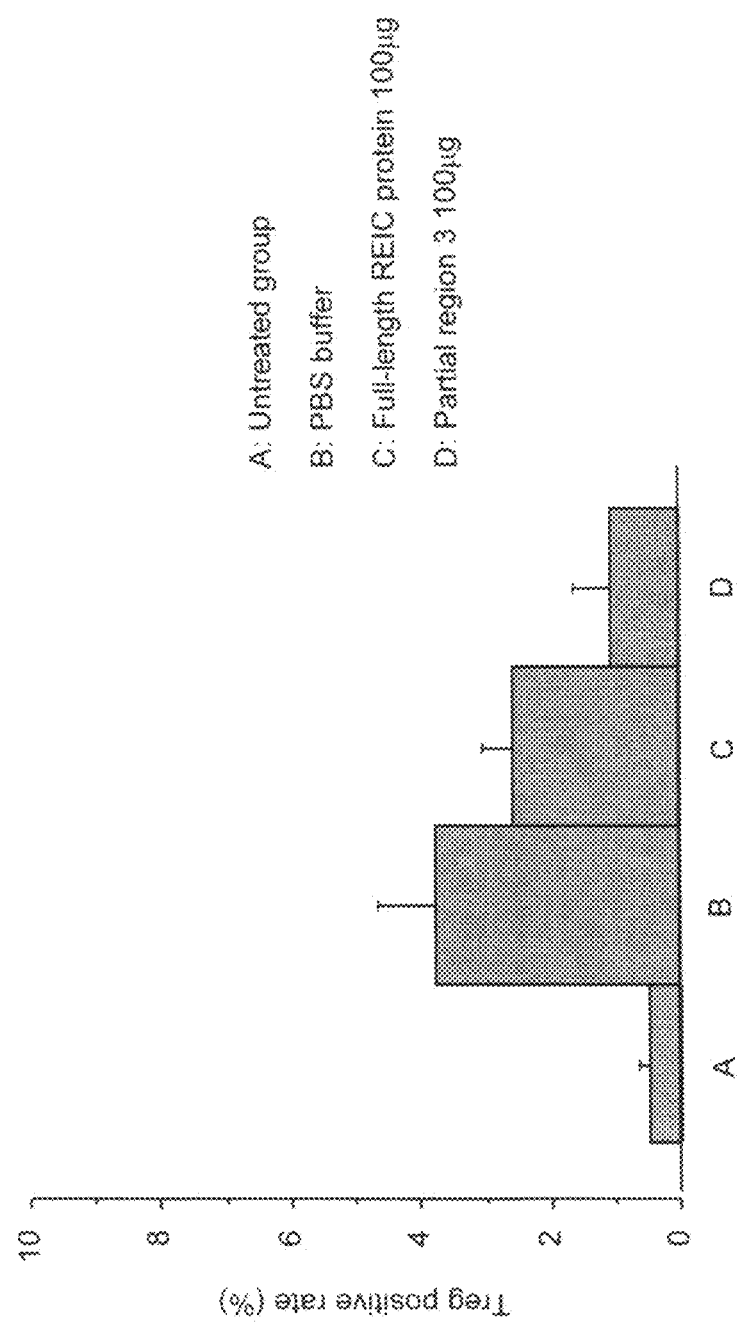
FIG. 12F is a graph showing the positive rate (%) of immunosuppressive T cells in each type of peripheral blood at the time (immediately before euthanasia) of completion of an experiment of treatment with the REIC/Dkk-3 protein (full-length or partial region 3), in an untreated group, or in a group treated with PBS buffer.
Figure 12G:
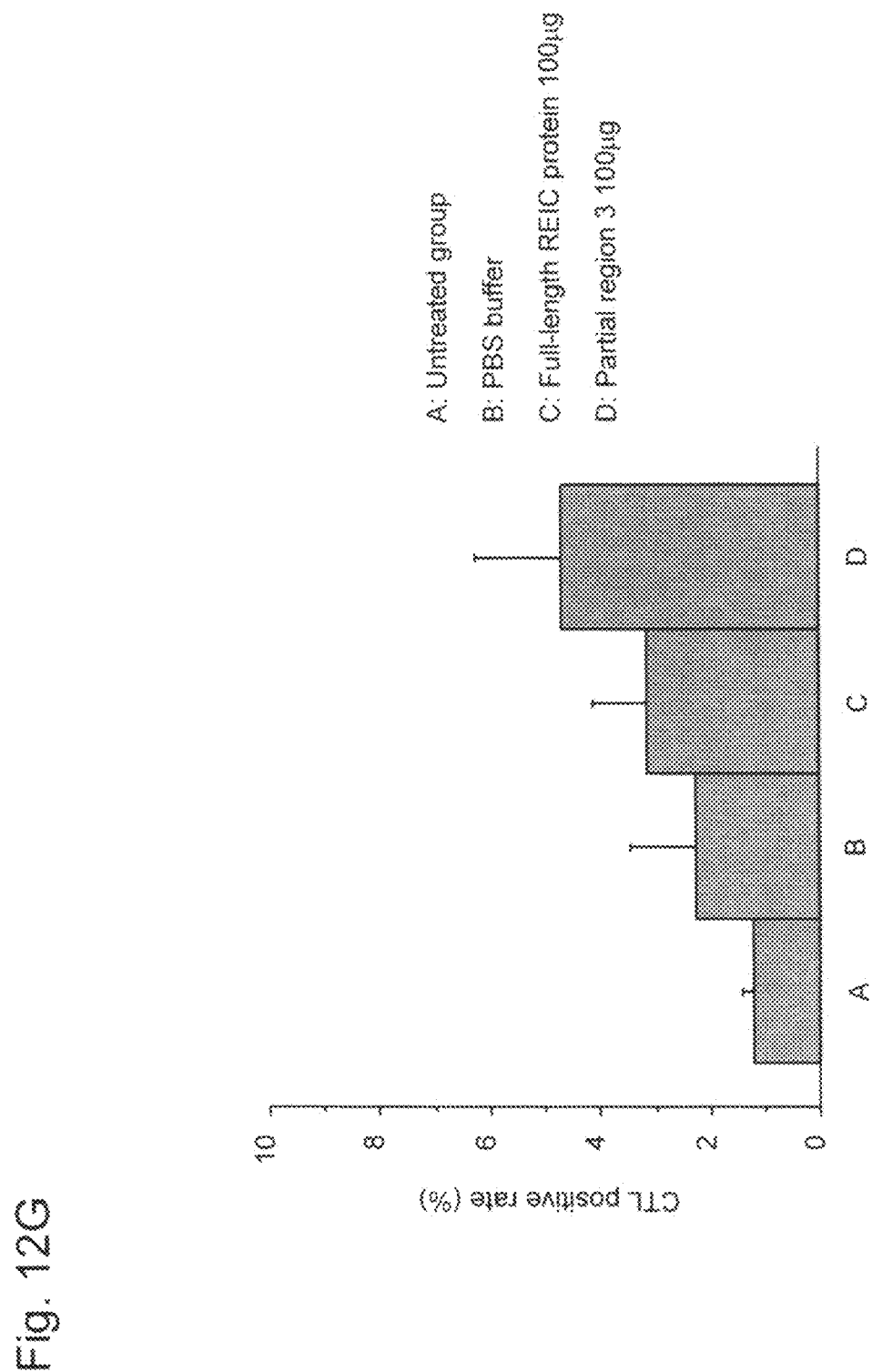
FIG. 12G is a graph showing the positive rate (%) of cytotoxic T cells in each type of peripheral blood at the time (immediately before euthanasia) of completion of an experiment of treatment with the REIC/Dkk-3 protein (full-length or partial region 3), in an untreated group, or in a group treated with PBS buffer.
Figure 12H:
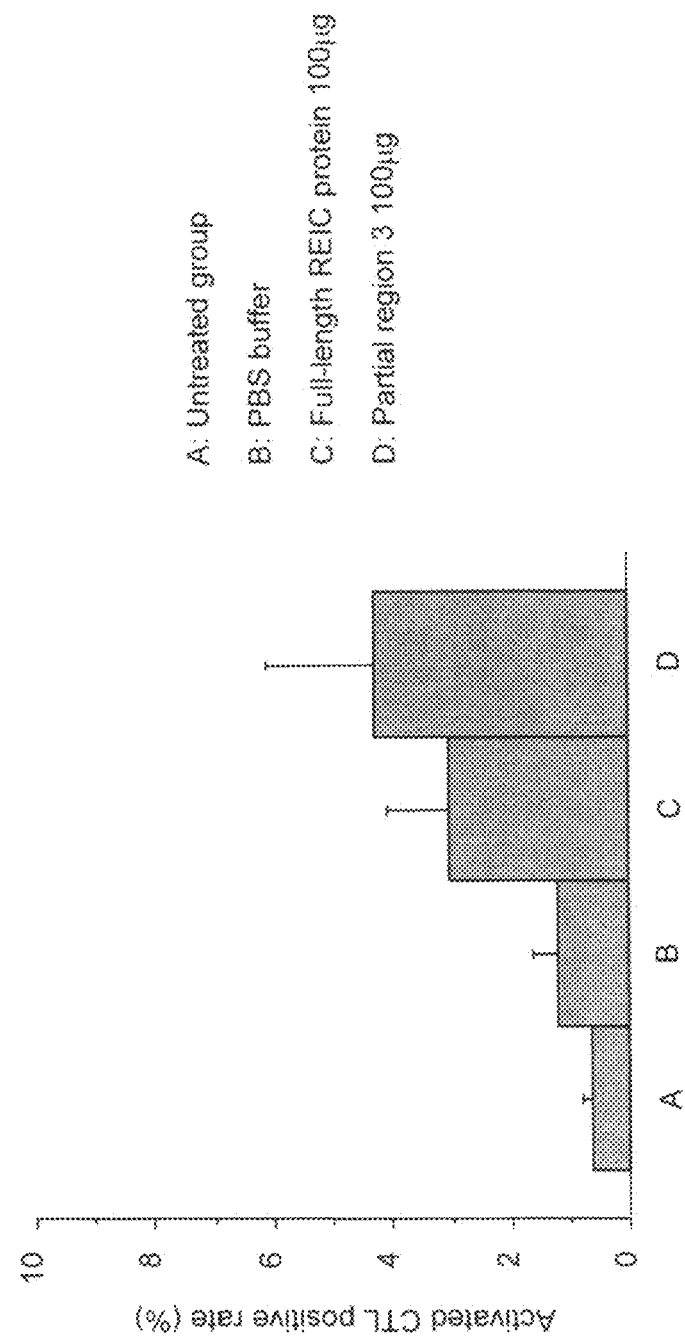
FIG. 12H is a graph showing the positive rate (%) of activated cytotoxic T cells in each type of peripheral blood at the time (immediately before euthanasia) of completion of an experiment of treatment with the REIC/Dkk-3 protein (full-length or partial region 3), in an untreated group, or in a group treated with PBS buffer.
Figure 12I:
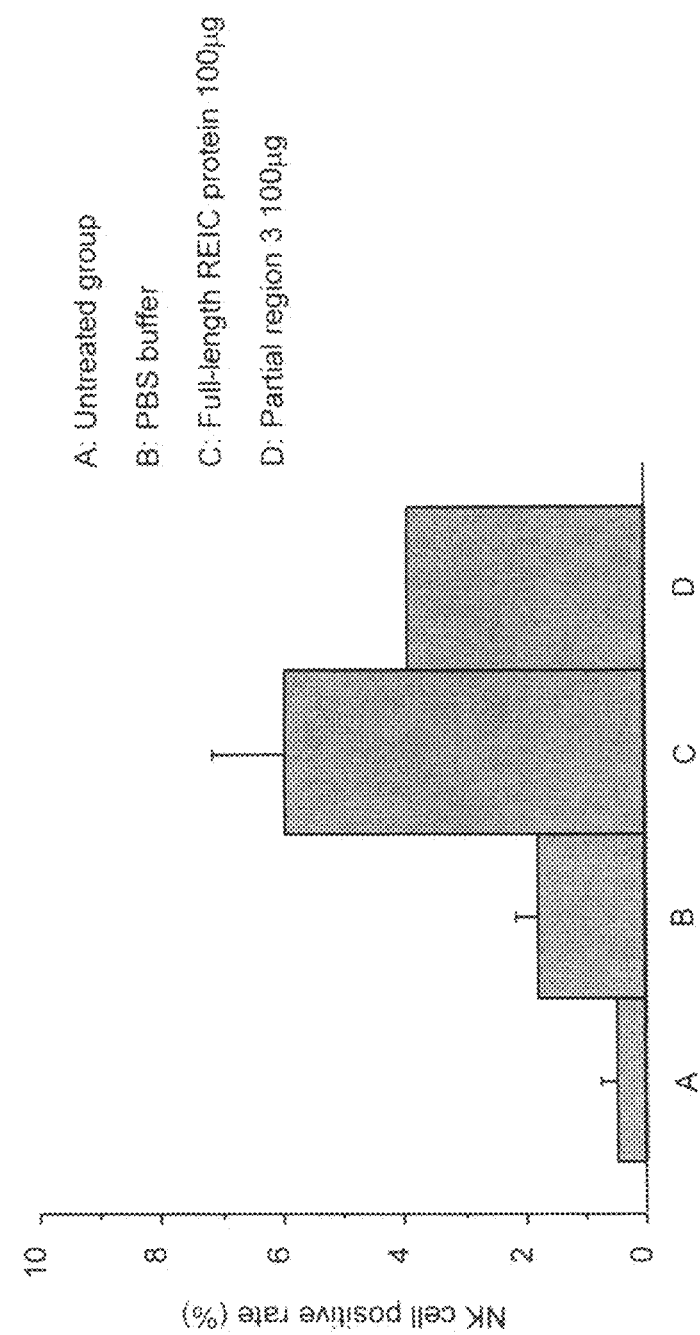
FIG. 12I is a graph showing the positive rate (%) of NK cells in each type of peripheral blood at the time (immediately before euthanasia) of completion of an experiment of treatment with the REIC/Dkk-3 protein (full-length or partial region 3), in an untreated group, or in a group treated with PBS buffer.
Figure 13:
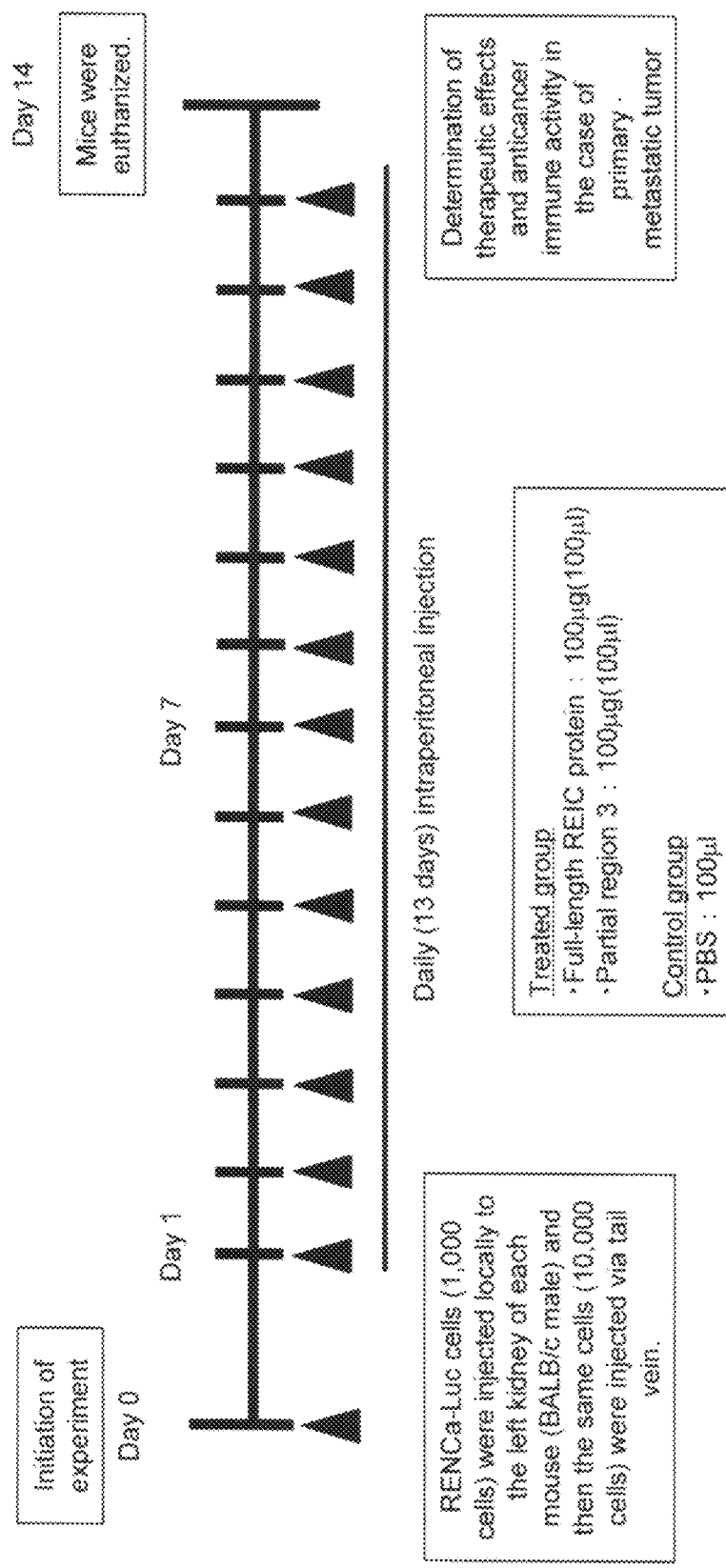
FIG. 13 shows protocols for an experiment of intraperitoneal administration of the human full-length REIC/Dkk-3 protein to orthotopic renal cell carcinoma·pulmonary metastasis model mice.

Subsequently, erythrocytes were lysed in a red blood cell lysis buffer. Cells were washed twice with PBS, suspended again in 200 µl of PBS, and thus a cell solution to be analyzed was prepared. $3 \times 10^4$ cells were collected using a FACS Calibur flow cytometer (Becton Dickinson) and then analyzed using CellQuest software (Becton Dickinson). An appropriate gate was set on the basis of the forward scatter pattern characteristic of these cells, and thus only cells within the gate were analyzed. As a result, the full-length REIC protein and the partial region 3 were observed to exhibit activity of inducing differentiation to almost all immunopotentiating cells (FIG. 12B, C, D, E, G, H, I) while also observed to exhibit activity of suppressing the differentiation induction of immunosuppressive cells (FIG. 12A, F). In particular, the partial region 3 was excellent in induction of cytotoxic T cell (CTL) differentiation (FIG. 12G H) and was observed to exhibit strong activity of suppressing immunoregulatory T cell (Treg) differentiation (FIG. 12F). As described above, it can be concluded that a protein containing the partial region 3 is applicable as an anticancer immunopotentiating agent, an anticancer agent, an antitumor agent, or an agent for inducting/suppressing immune cell differentiation. The same applies to the full-length REIC protein containing the partial region 3.

Example 8

Experiment Concerning the Anti-Tumor Effects of the Full-Length REIC Protein Using Renal Cell Carcinoma Model Mice Mouse renal cell carcinoma cells (RENCA-Luc cell line) were prepared by causing a RENCA cell line to stably express a Luciferase gene. To examine the tumor suppressive effects of the REIC protein by an in vivo experiment, renal cell carcinoma model mice were produced using the RENCA-Luc cell line. For preparation of orthotopic tumors, male BALB/C mice were anesthetized with Nembutal and then RENCA-Luc cells ($10^3$ cells) were locally injected into the left kidney. Immediately after injection, $10^4$ cells were injected via tail vein, so that a renal cell carcinoma mouse model having pulmonary metastatic foci was prepared (Day 0). A control group and a treatment group were treated as follows.

A: PBS (100 µl) was intraperitoneally administered every day (13 days) a total of 13 times.
B: REIC protein (10 µg/100 µl PBS) was intraperitoneally administered every day (13 days) a total of 13 times.
C: REIC protein (100 µg/100 µl PBS) was intraperitoneally administered every day (13 days) a total of 13 times.

Figure 14A:
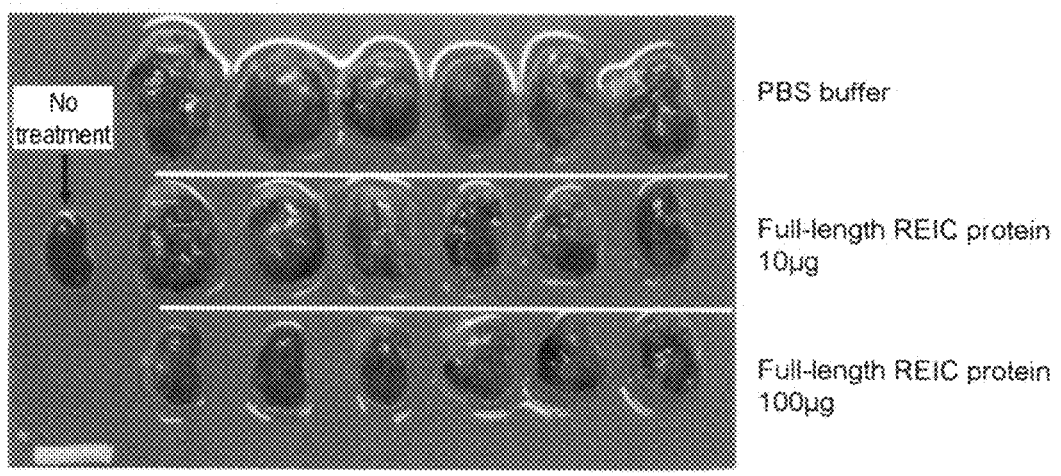
FIG. 14A is a photograph showing the tumor tissue of primary lesions of renal cancer in an experiment of intraperitoneal administration of the human full-length REIC/Dkk-3 protein (10 µg, 100 µg) to orthotopic renal cell carcinoma·pulmonary metastasis model mice.
Figure 14B:
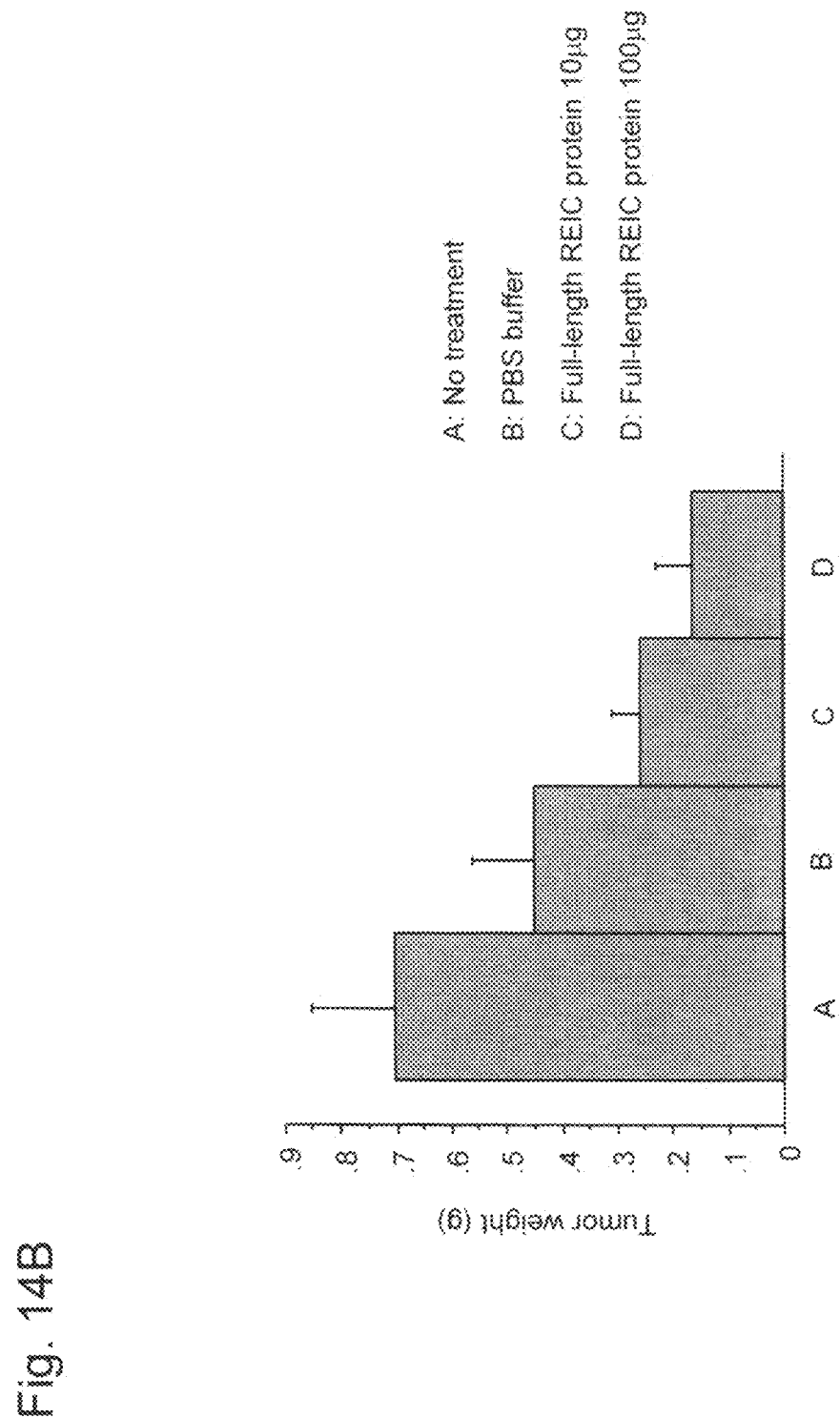
FIG. 14B is a graph showing the mean values of tumor weights (g) of the primary lesions of renal cancer at the time of (immediately before euthanasia) completion of an experiment of the treatment with the full-length REIC/Dkk-3 protein (10 µg, 100 µg) or in a group treated with PBS buffer.
Figure 15A:
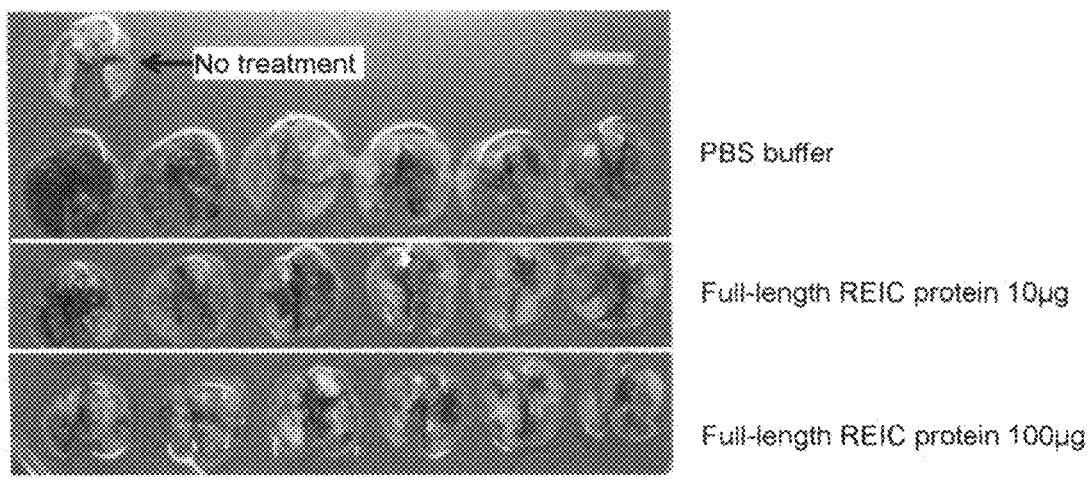
FIG. 15A shows photographs showing the tumor tissues of pulmonary metastases in an experiment of intraperitoneal administration of the human full-length REIC/Dkk-3 protein (10 µg, 100 µg) to orthotopic renal cell carcinoma·pulmonary metastasis model mice.
Figure 15B:
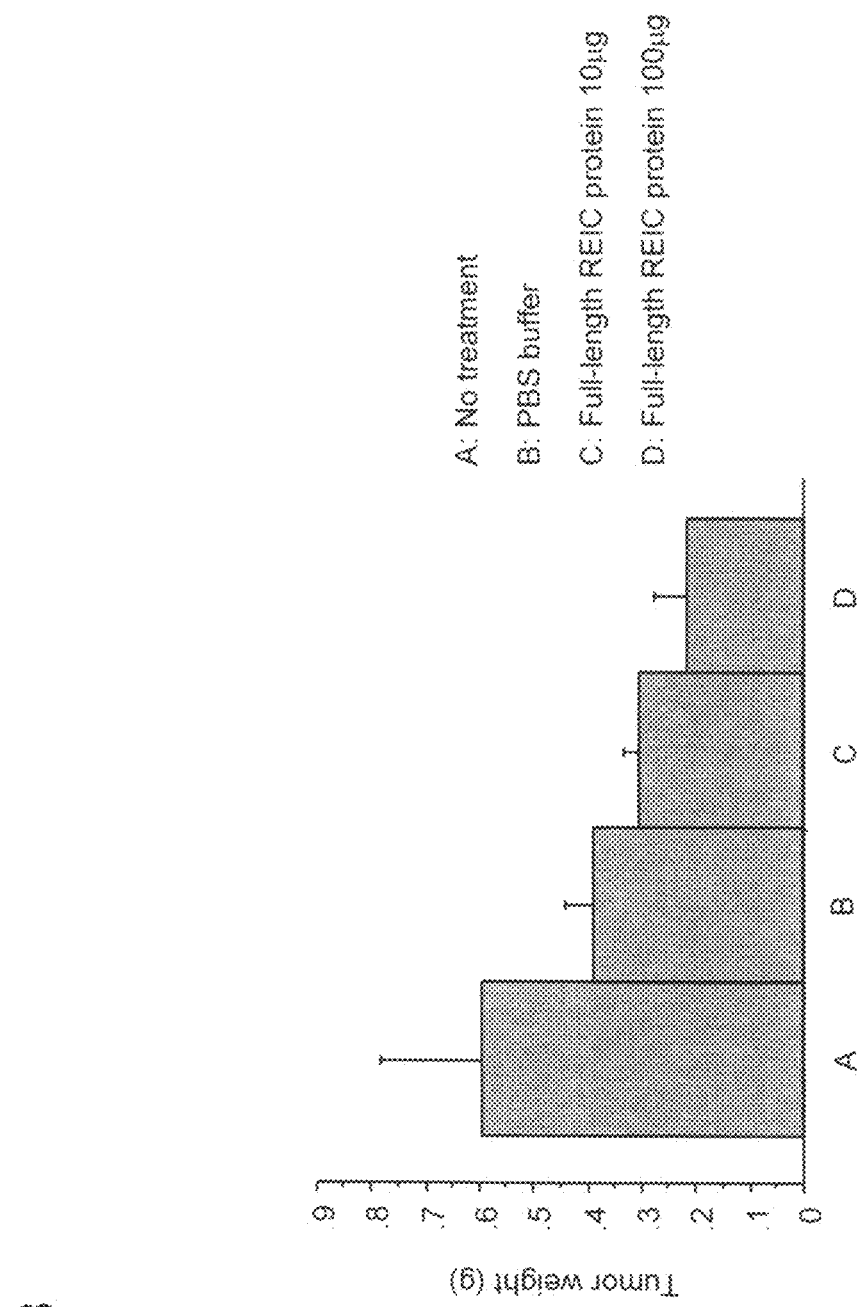
FIG. 15B is a graph showing the mean values of tumor weights (g) of pulmonary metastases at the time (immediately before euthanasia) of completion of an experiment of treatment with the full-length REIC/Dkk-3 protein (10 µg, 100 µg) or in a group treated with PBS buffer.

On Day 14 after the start of administration (Day 14), mice were euthanized. The thus excised tumors were analyzed for tumor size and tumor weight. As shown in FIG. 14A, tumor shrinkage was observed in the group treated with the REIC protein, compared with the group of untreated mice and the group treated with the buffer. It was suggested that the tumor shrinkage effect became more significant depending on the dose of the REIC protein (FIG. 14B). Tumor shrinkage was also similarly observed in pulmonary metastatic foci (FIG. 15A, B).

Example 9

Differentiation Induction Experiment Using Mouse Bone Marrow Cells

Figure 16A:
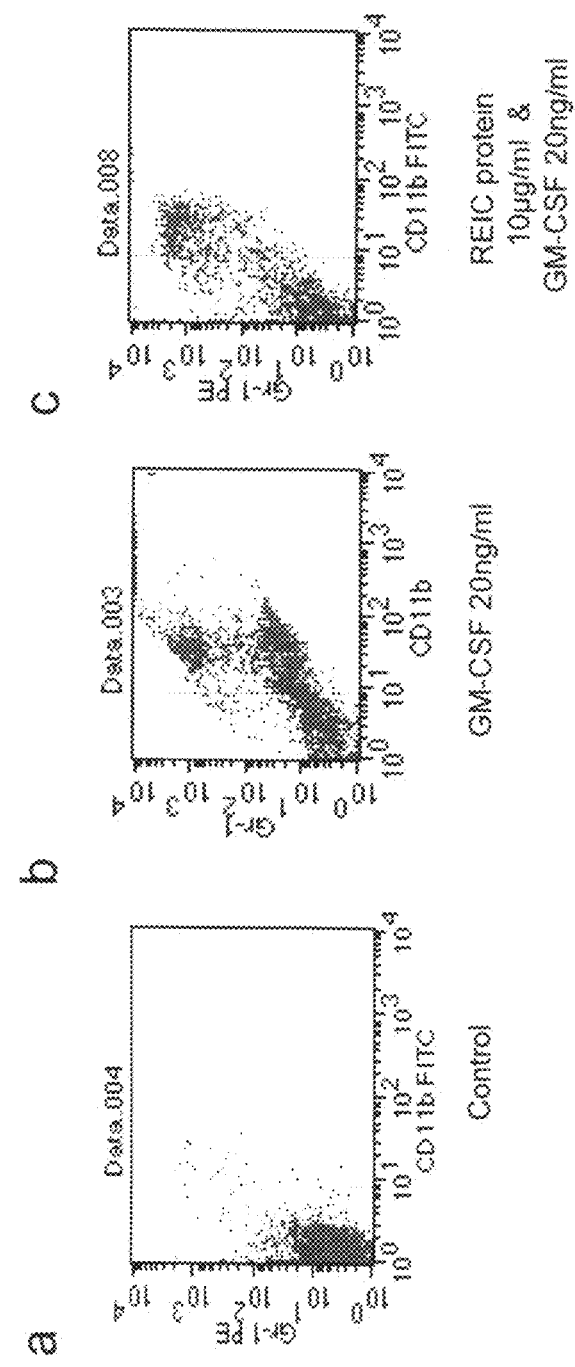
FIG. 16A shows cytograms showing the differentiation induction of MDSC when GM-CSF (20 µg/ml) (16A-a) or a mixture (16A-c) of a REIC protein (10 µg/ml) and GM-CSF (20 µg/ml) was administered to bone marrow cells collected from untreated mice. 16A-a shows the result of a control.
Figure 16B:
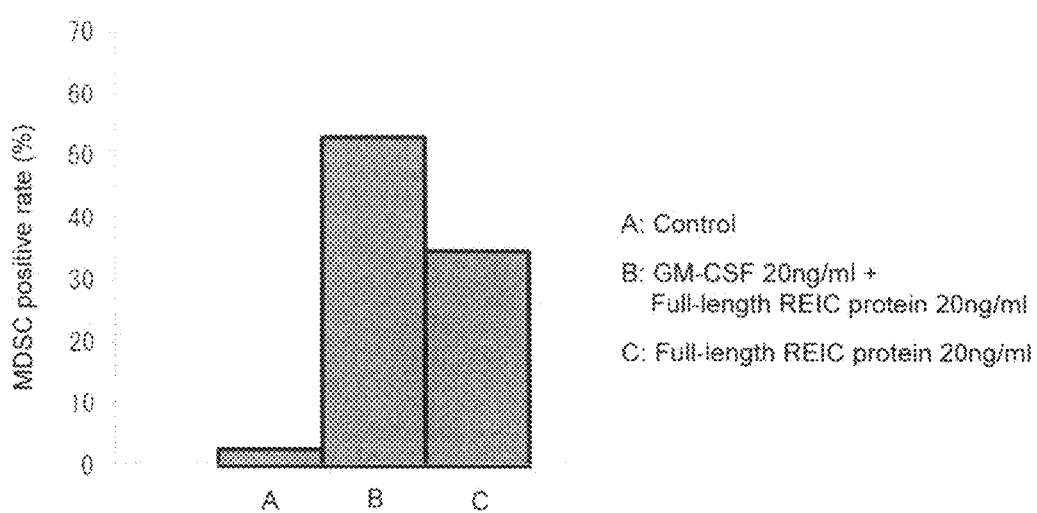
FIG. 16B is a graph showing the positive rate (%) of MDSC found from the cytogram shown in FIG. 16A.
Figures 2, 17A:
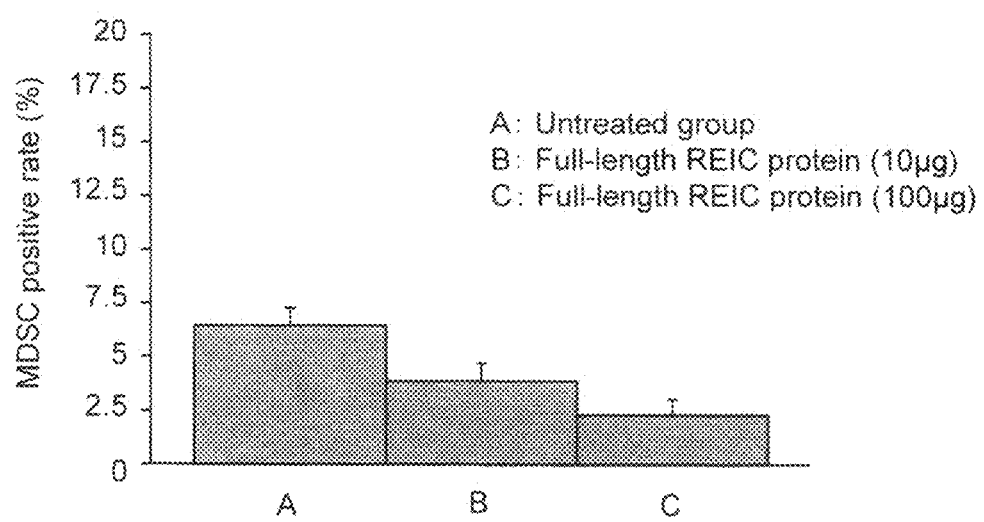
Figures 1, 17B:
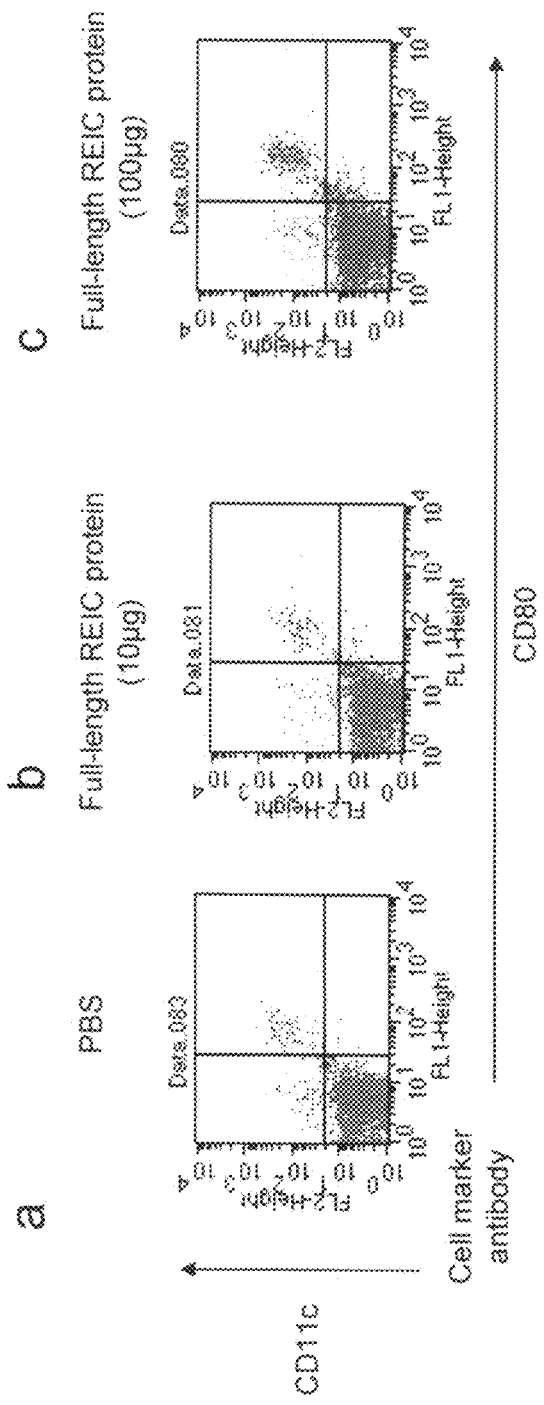
Figures 2, 17B:
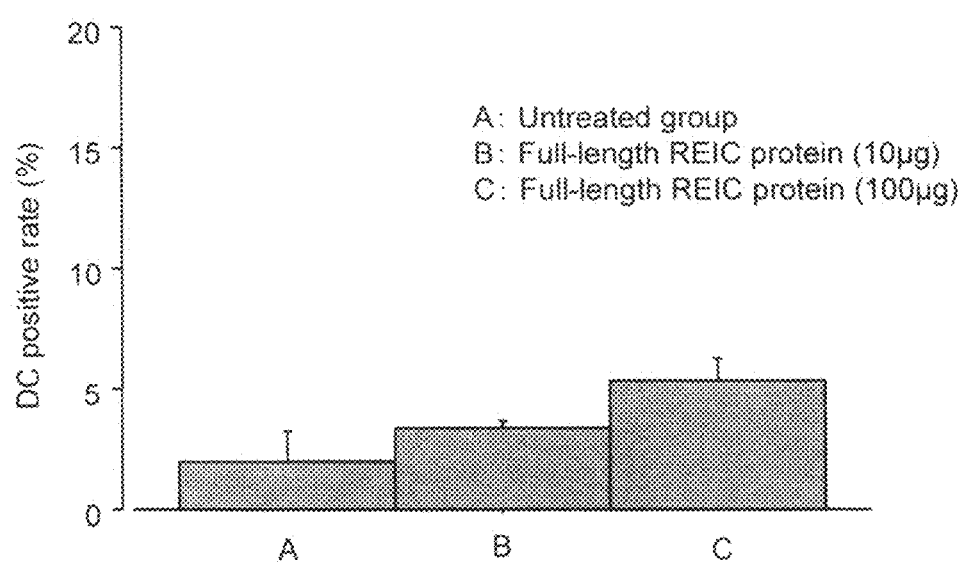
Figures 1, 17C:
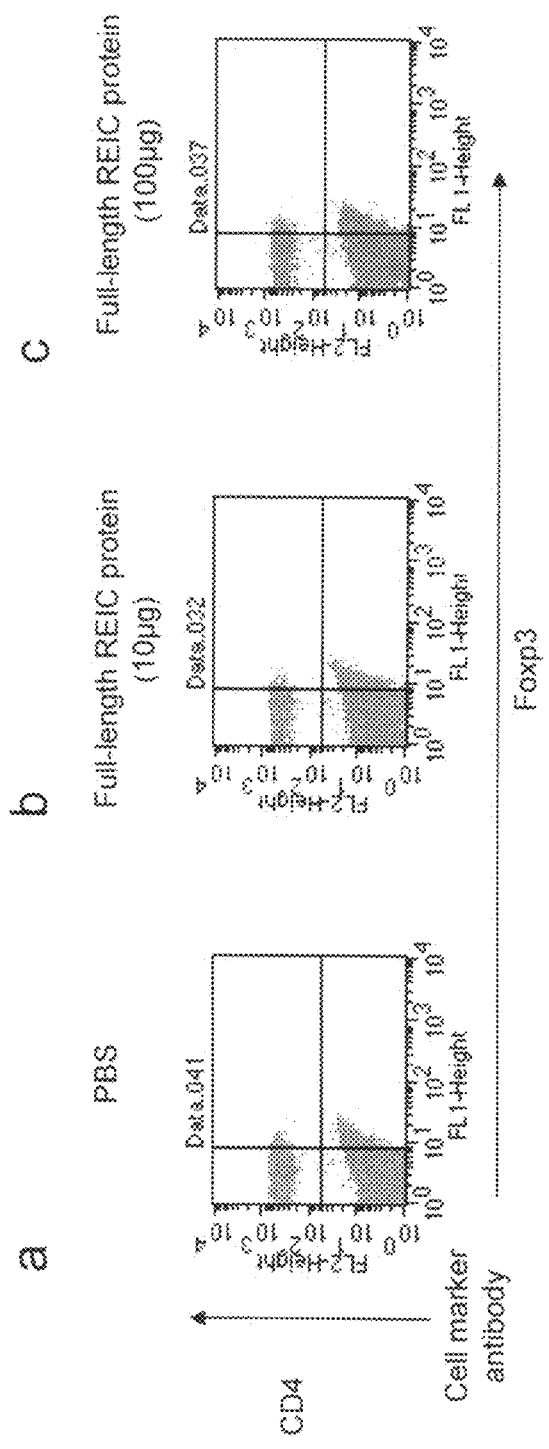
Figures 2, 17C:
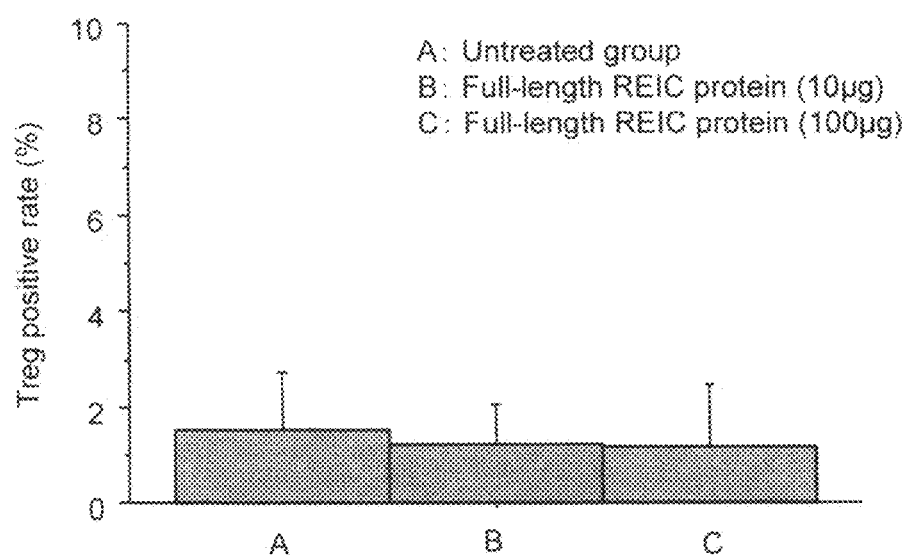
Figures 1, 17D:
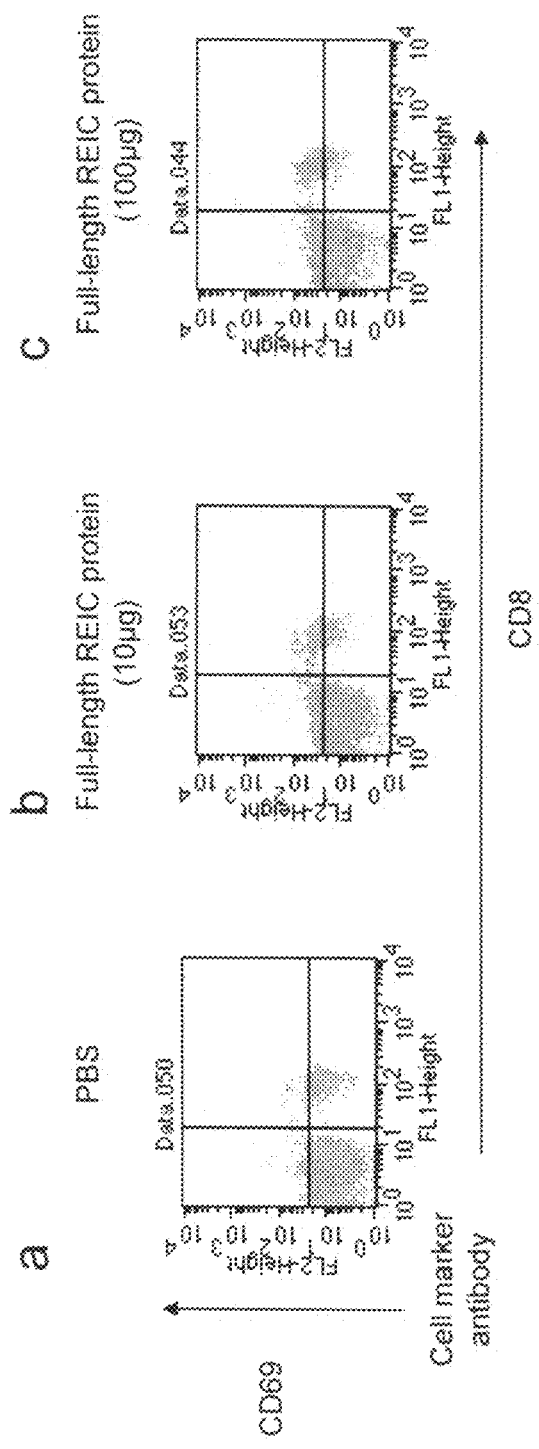
Figures 2, 17D:
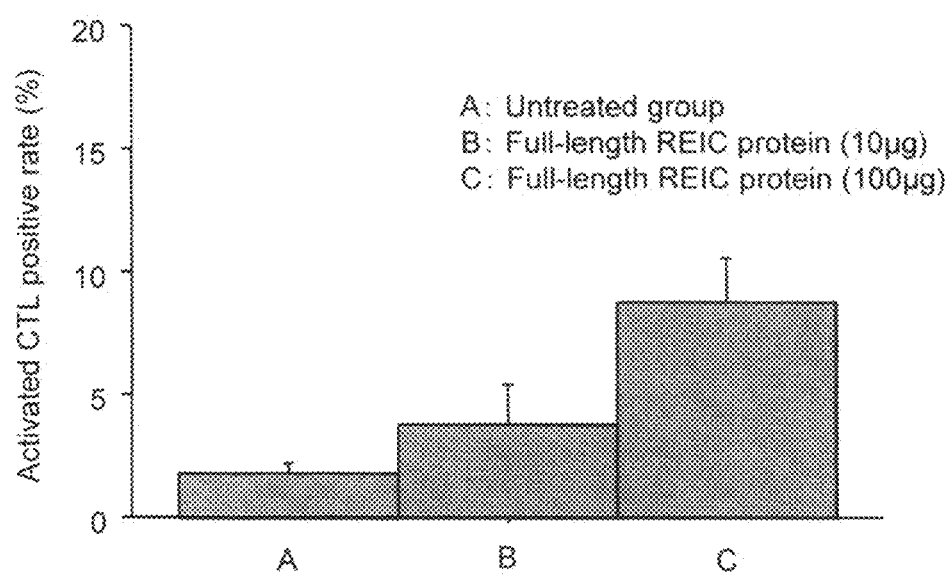
Figures 1, 17E:
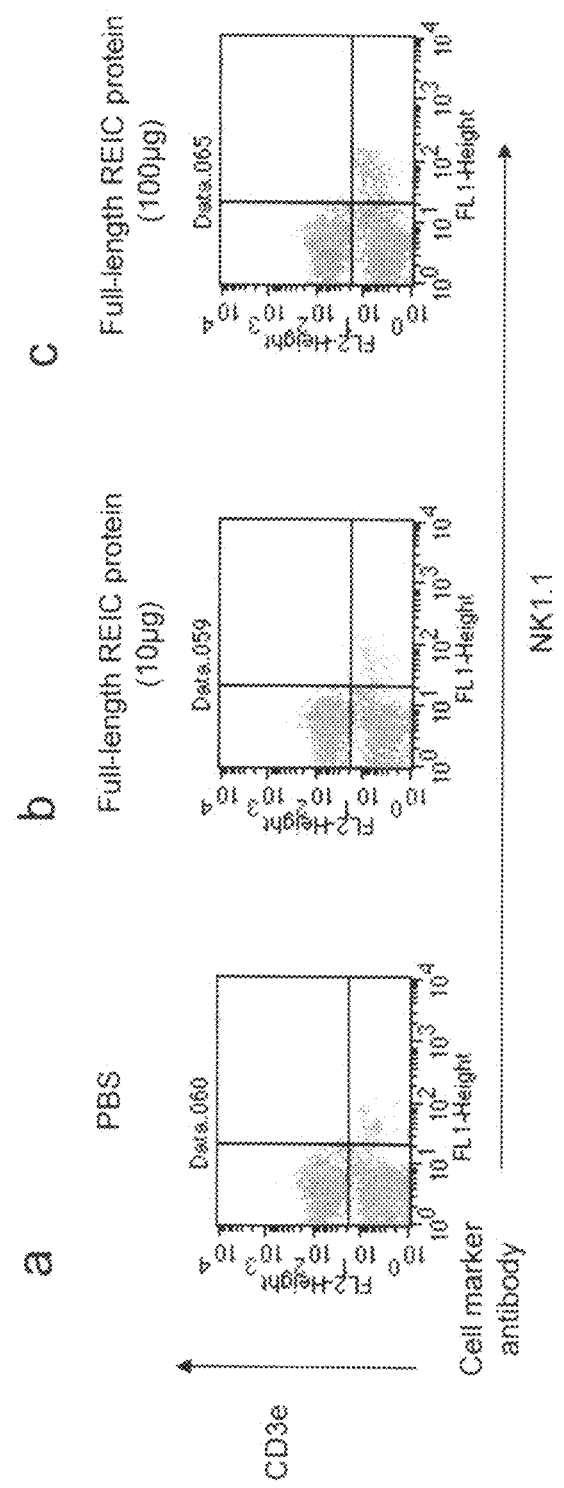
Figures 2, 17E:
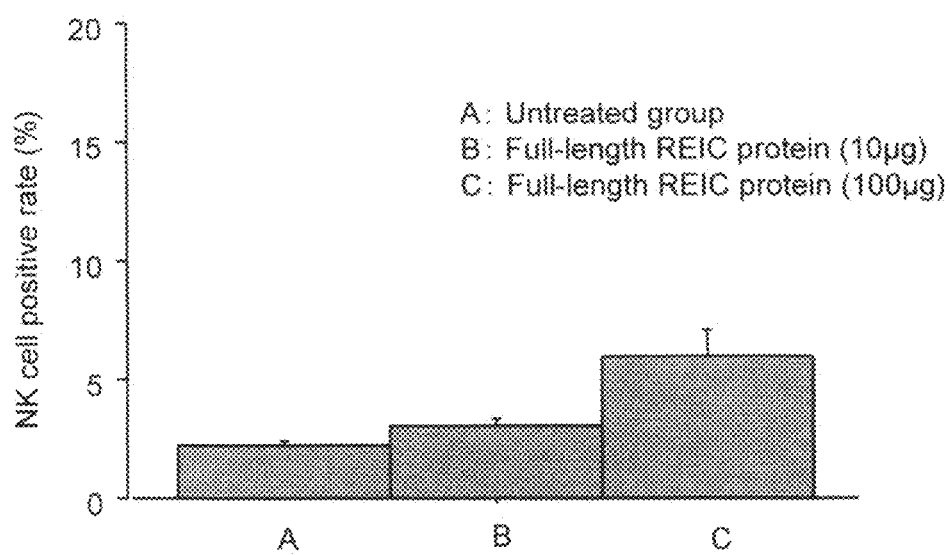

Bone marrow was collected from an untreated normal mouse and then suspended by pipetting. Mouse bone marrow cells were cultured in a flat bottom 6-well plate. On the next day, cells were washed twice with PBS, and then cells that had adhered were used for the experiment. Through the addition of GM-CSF (20 ng/ml, purchased from R&D Systems) alone or the addition of GM-CSF and the full-length REIC protein (10 µg/ml), the effects of the REIC protein to suppress the induction of the differentiation to myeloid derived suppressor cells (MDSC) were analyzed. On Day 6 after the start of the culture of mouse bone marrow cells, cells were collected by trypsin treatment and then stained with antibodies against surface antigen markers (GR-1, CD11b) of MDSC. $3 \times 10^4$ cells were analyzed using a FACS Calibur flow cytometer (Becton Dickinson). Whereas the percentage of MDSC was 2.56% in the case of no treatment, the percentage of MDSC increased to 53.04% in the case in which GM-CSF had been administered (FIG. 16A, B). This means that GM-CSF enhanced the induction of MDSC differentiation, so as to suppress the capacity of immune activation. When GM-CSF and the full-length REIC protein were mixed, differentiation to MDSC was induced at a rate (34.71%) lower than the case of GM-CSF alone. The result means that the REIC protein suppressively acts on induction of MDSC differentiation, so as to exhibit the capacity of immune activation.

Example 10

Flow Cytometry of the Immunocompetent Cells in Mouse Venous Blood of Example 8

The percentage of the immunocompetent cells in mouse venous blood obtained in Example 8 was analyzed by flow cytometry. In a manner similar to Example 7, 30 µl of a 0.2% EDTA solution was added to 750 µl of mouse peripheral blood collected from inferior vena cava for anticoagulation. Each of the following antibodies (1 µl each) fluorescently labeled differently (purchased from eBioscience) was added to 30 µl of blood, the solution was stirred, incubation was performed at 4° C. for 60 minutes, and thus each type of the following immunocompetent cells was stained.
Bone marrow-derived immunosuppression cells (anti-GR-1 antibody, anti-CD11b antibody)
Activated dendritic cells (CD11c+/CD80+) (anti-CD11c antibody, anti-CD80 antibody)
Immunoregulatory T cells (anti-CD4 antibody, anti-Foxp3 antibody)
Activated cytotoxic T cells (anti-CD69 antibody, anti-CD8 antibody)
NK cells (anti-CD3 antibody, anti-NK1.1 antibody)

Subsequently, erythrocytes were lysed in a red blood cell lysis buffer. Cells were washed twice with PBS, suspended again in 200 µl of PBS, and thus a cell solution to be analyzed was prepared. $3 \times 10^4$ cells were collected using a FACS Calibur flow cytometer (Becton Dickinson) and then analyzed using CellQuest software (Becton Dickinson). An appropriate gate was set on the basis of the forward scatter pattern characteristic of these cells, and thus only cells within the gate were analyzed. FIG. 17A to FIG. 17E show the results. In the cases of dendritic cells (FIGS. 17B-1 and B-2), activated cytotoxic T cells (CTL, FIGS. 17D-1 and D-2) and NK cells (FIGS. 17E-1 and E-2), the positive rate was found to increase depending on the dose of the REIC protein. All of these immunocompetent cells function to accelerate immunoactivity. Moreover, it was demonstrated that of MDSC (FIGS. 17A-1 and A-2) and Treg (FIGS. 17C-1 and C-2) suppressively act on the immune system, the positive rate decreases depending on the dose of the REIC protein.

As described above, it was found that the REIC protein has the function of activating the immune system by attenuating the immunosuppression system. Decreased immunocompetence in an in vivo micro environment is known to be able to accelerate tumor development and growth, which is mainly caused by the development and induction of immunosuppressive cells. Therefore, the REIC protein and a DNA vector expressing the protein are applicable as agents for inhibiting immunosuppression, such as anticancer agents, antitumor agents, agents for activating anticancer immunity, and agents for inducing immunocompetent cell differentiation.

Example 11

Analysis of Interaction Between REIC Protein and Tctex-1 by Yeast 2-Hybrid Method (Y2H)

The ProQuest Two-hybrid System (Invitrogen, Carlsbad, Calif.) was used for the yeast 2-hybrid method. The full-length cDNA of human REIC/Dkk-3 was amplified by the following two primer DNAs.

```
Forward:
                                    (SEQ ID NO: 12)
5'-ACGCGTCGACCATGCAGCGGCTTGGGGCCAC-3'

Reverse:
                                    (SEQ ID NO: 13)
5'-TTCCTTTTTTGCGGCCGCTAAATCTCTTCCCCTCCCA-3'
```

The thus amplified cDNA was inserted between Sal 1 and Not 1 enzyme cleavage sites of a pDBLeu bait vector, and then the vector was introduced into the yeast MaV203 strain. Subsequently, a REIC/Dkk-3 expressing clone was isolated and then transformed into the human heart cDNA library cloned into pPC86 (Invitrogen). Clones that had been successfully introduced were collected using selective medium supplemented with β-galactosidase substrate. Gene introduction, plasmid isolation, confirmation of DNA constructs, and preparation of yeast lysates were performed referring to the instructions of Invitrogen.

Figure 18A:
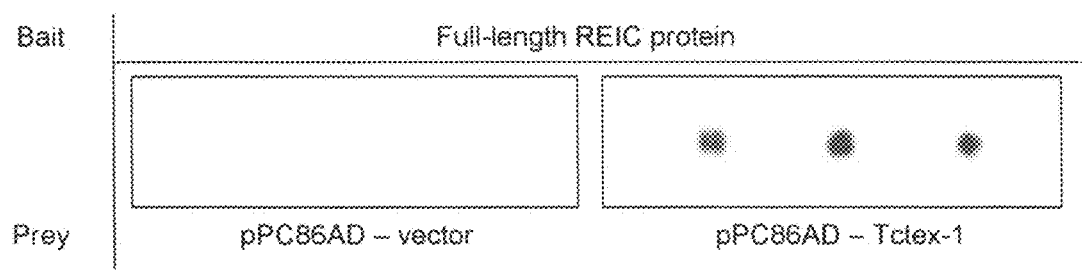
FIG. 18A shows the result of yeast 2-hybrid analysis, exhibiting an interaction between a REIC/Dkk-3 protein and a Tctex-1 protein.

To identify interaction partners for REIC/Dkk-3, the yeast 2-hybrid method screening was performed using the REIC/Dkk-3 protein as a bait. REIC/Dkk-3 expression is enhanced in mouse and human cardiac tissue, a human cDNA library of normal cardiac tissue was subjected to screening. Among clones with activated reporter genes, 4 clones were successfully cultured. Inserted genes were separated and collected from these clones by a plasmid rescue method, gene introduction was performed again, and then culture was performed using reporter selective media. FIG. 18A shows the results. In FIG. 18A, blue colonies were observed in the right panel containing Tctex-1. Blue colonies clearly indicate the interaction (association) between the REIC/Dkk-3 protein and the Tctex-1 protein. These results suggested that Tctex-1 is an interaction partner for REIC/Dkk-3 (FIG. 18A).

Example 12

Analysis of REIC-Tctex-1 Interaction by Immunoprecipitation and Western Blot

For the purpose of confirming binding partners by the immunoprecipitation method, the human full-length cDNA of REIC/Dkk-3 or Tctex-1 was inserted into a pcDNA3.1/Myc-His(−)A or a pcDNA3.2/V5/GW/D-TOPO plasmid (Invitrogen), followed by cloning. For the purpose of transient gene expression, 293T cells were transfected with the plasmid DNA using lipofectamine 2000. 293T cells were co-transfected with Myc-tagged REIC/Dkk-3 or VS-tagged Tctex-1. At 48 hours after transfection, 293T cells were lysed, a buffer (20 mM Tris-HCl, pH 7.5, 1% Triton X-100, 150 mM NaCl, 5 mM EDTA and Complete Protease Inhibitor Cocktail (Roche, Basel, Switzerland)) was added. One (1) mg of a mouse-derived non-specific IgG antibody (Santa Cruz Biotechnology, Santa Cruz, Calif.) was added to the cell lysate, incubation was performed, and then 1 ml of protein G sepharose (Invitrogen) or an anti-Myc mouse-derived monoclonal antibody (Invitrogen, Cat. No. R95025) was added. After 12 hours of incubation at 4° C., the precipitates were washed and then boiled in a buffer in which SDS had been dissolved. The precipitates were subjected to the Western blot method using a mouse-derived V5 monoclonal antibody (Invitrogen, Cat. No. R96025).

Figure 18B:
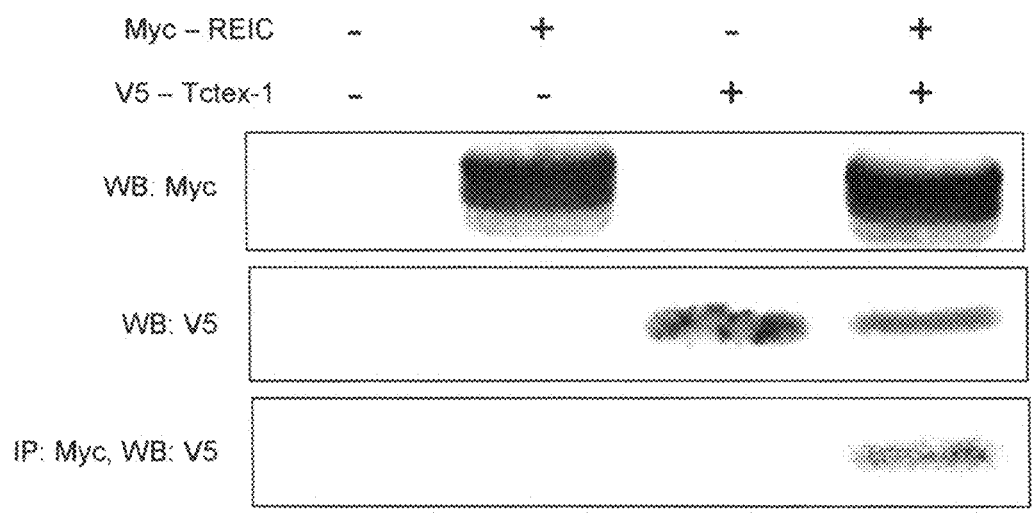
FIG. 18B shows the results of immunoprecipitation analysis, exhibiting an interaction between the REIC/Dkk-3 protein and the Tctex-1 protein and the results of Western blot analysis.

To confirm the interaction between REIC/Dkk-3 and Tctex-1, in vitro pull down assay was performed by the immunoprecipitation method. Binding assay of the V5-Tctex-1 fusion protein was performed using a cell lysate of 293T cells expressing the Myc-REIC/Dkk-3 fusion protein. Binding to Tctex-1 was detected by the Western blot method using a V5 antibody. Binding of Tctex-1 to the REIC/Dkk3 protein was detected from an immunoprecipitation sample obtained by adding the Myc antibody to cell lysates of cells co-transfected with REIC/Dkk-3 and Tctex-1. FIG. 18B shows the results. The results of Examples 11 and 12 demonstrate that the interaction between the REIC/Dkk-3 protein and the Tctex-1 protein was confirmed to take place and was reproduced by both the yeast 2-hybrid method and the immunoprecipitation method.

Example 13

Analysis of the Region of the REIC Protein Binding to Tctec-1 by the Mammalian 2-Hybrid Method (M2H)

To perform the mammalian cell 2-hybrid assay, cDNAs encoding REIC/Dkk-3 with various amino acid lengths were introduced into plasmids for cloning a pM GAL4 DNA binding domain. Furthermore, cDNA encoding full-length Tctex-1 was introduced into a plasmid for cloning a pVP16 transcriptional activity domain (Clontech Laboratories, Mountain View, Calif.). Templates for human REIC/Dkk-3 each having different amino acid lengths were generated and amplified by the PCR method using appropriate primer pairs. The complete full-length cDNA of Tctex-1 was amplified with the following primers.

```
                                      (SEQ ID NO: 14)
   Forward 5'-CCGGAATTCATGGAAGACTACCAGGCTGC-3'

(SEQ ID NO: 15)
   Reverse 5'-GGGAAGCTTTCAAATAGACAGTCCGAAGG-3
```

About $2\times10^5$ 293 T cells were co-transfected with 400 ng of pVP16, 400 ng of pM, 250 ng of pFR-Luc firefly-derived luciferase reporter plasmid (Promega, Madison, Wis.), and 10 ng of phRL-TKRenilla-derived luciferase reporter plasmid (Promega). The transfected cells were cultured for 48 hours, and then luciferase activity was measured using a dual-luciferase reporter assay system (Promega). Errors due to differences in transfection efficiency were normalized by measuring Cypridina-derived luciferase activity resulting from the transfection of phRL-TK gene.

Figure 19A:
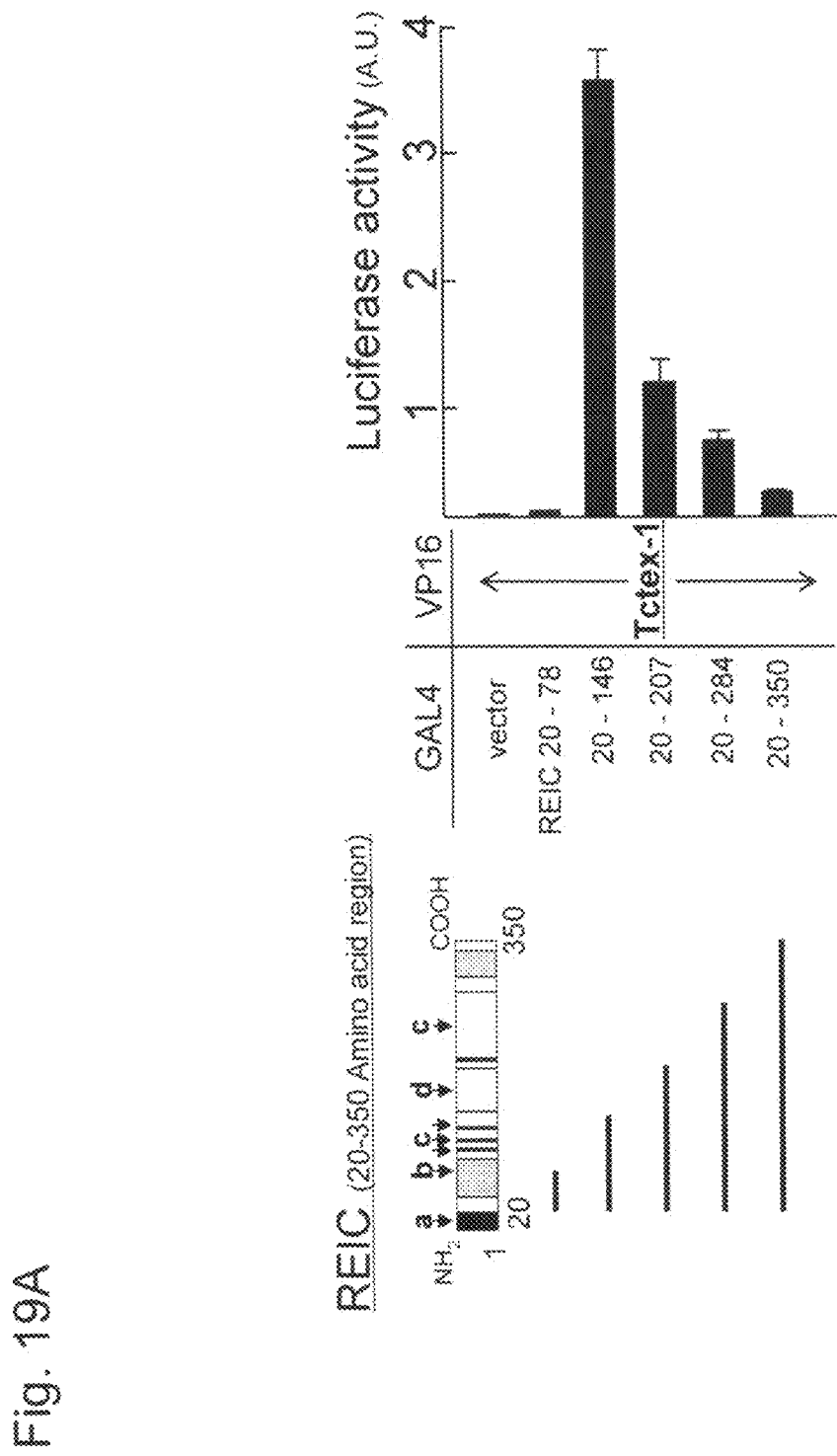
FIG. 19A shows the results of animal cell 2-hybrid analysis, exhibiting an interaction between the full-length REIC/Dkk-3 protein and the Tctex-1 protein.
Figure 19B:
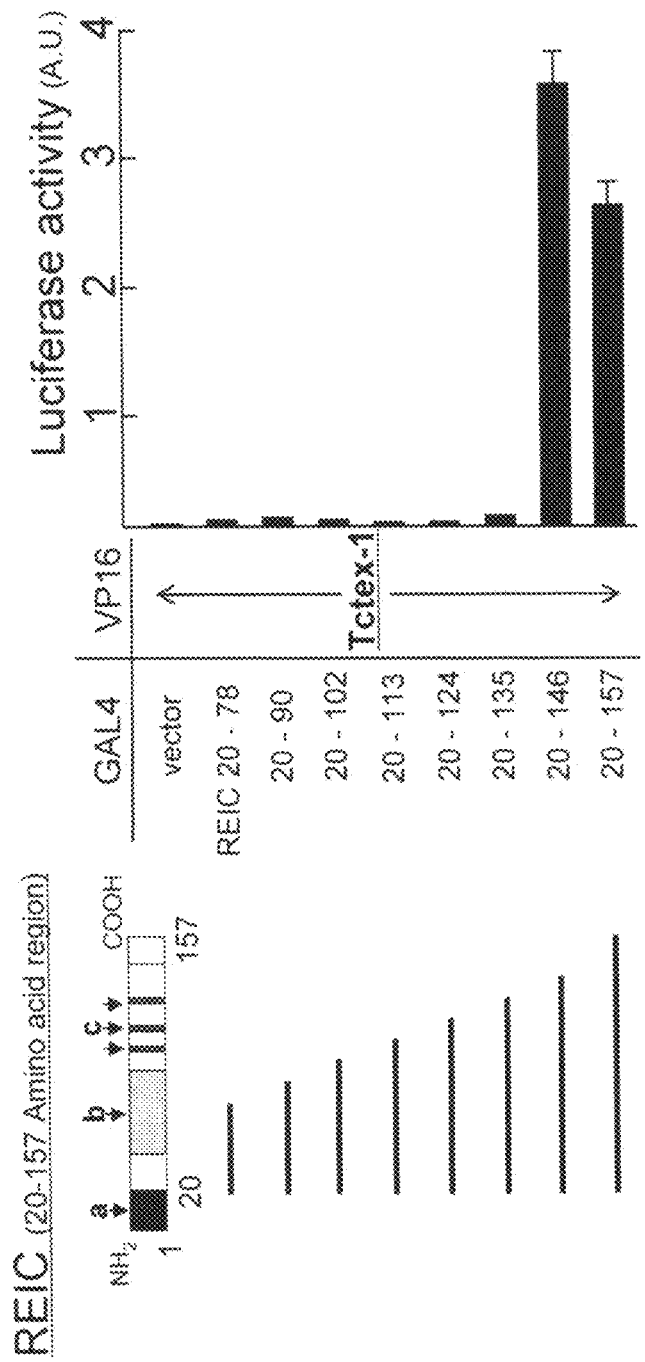
FIG. 19B shows the results of animal cell 2-hybrid analysis, exhibiting an interaction between a partial region of the human full-length REIC/Dkk-3 protein and the Tctex-1 protein.

Interaction between REIC/Dkk-3 and Tctex-1 was analyzed by the mammalian 2-hybrid method for searching for REIC/Dkk-3 partial regions important for interaction with Tctex-1. 293T cells were co-transfected with a GAL4 plasmid with REIC/Dkk-3 cDNA (of each amino acid length) introduced thereinto and a VP16 plasmid with the cDNA of full-length Tctex-1 introduced thereinto. Luciferase activity in the cell lysate of 293T cells was measured. When the activity was observed, binding of each REIC/Dkk-3 partial region to Tctex-1 was determined. As a result, it was revealed that a REIC/Dkk-3 partial region composed of 20 to 146 amino acid residues is important as a binding region binding to Tctex-1. Furthermore, it was revealed that REIC/Dkk-3 partial regions having amino acid lengths longer than that of the aforementioned partial region have low activity of binding to Tctex-1 (FIG. 19A). To further select the regions of REIC/Dkk-3 for binding to Tctex-1, REIC/Dkk-3 partial regions were shortened in stages. Luciferase activity indicating the binding with Tctex-1 was detected in REIC/Dkk-3 having 20-146 amino acids and partial regions of 20-157 amino acid residues. Only weak activity was observed for a partial region composed of 20-135 amino acid residues. These results suggest that a REIC/Dkk-3 partial region composed of 136-157 amino acid residues is involved in the interaction between REIC/Dkk-3 and Tctex-1 (FIG. 19B).

FIG. 20A shows the amino acid sequence alignment of the REIC protein and the TcTex-1 binding region of a dynein intermediate chain (DIC). Another group has reported the binding of Tctex-1 (that is, a Dynein light chain protein) with the partial region [$^{120}$SDSELGRRLHKLGVSK-VTQVDFL$^{142}$] (SEQ ID NO: 16) of the dynein intermediate chain (DIC). The Tctex-1 binding region of REIC/Dkk-3 was found to be [$^{136}$VGDEEGRRSHECIIDEDCGPSM$^{157}$] (SEQ ID NO: 17). Sequence comparison with the Tctex-1 binding region of DIC revealed that the consensus sequence was [-E-X-G-R-R-X-H-] (X denotes an arbitrary natural amino acid) (SEQ ID NO: 18).

FIG. 20B shows the amino acid sequence alignment of the Tctex-1 binding domain of the REIC protein and a known Tctex-1 binding protein. The amino acid sequence motif of the Tctex-1 binding protein was [-R/K-R/K-X-X-R/K-] (X denotes an arbitrary natural amino acid) (SEQ ID NO: 20). The amino acid sequence of the REIC/Dkk-3 binding region is consistent with other sequences in terms of the motif alone containing [-RR-]. This is characteristic unlike the motifs of other binding partners for Tctex-1.

Example 14

Analysis of the Intracellular Localization Patterns of REIC/Dkk-3 Protein and Tctex-1

Immunocytochemical staining of REIC/Dkk-3 and Tctex-1 in OUMS24 cells was performed by co-staining the endoplasmic reticulum organelle. Cells were cultured on 24-well plates under 30% to 40% confluent conditions. Furthermore, cells were fixed with 4% paraformaldehyde·100 mM phosphate buffer and then blocked with saline and 3% BSA. A rabbit-derived anti-REIC/Dkk-3 polyclonal antibody (1:200 dilution in PBS) or a rabbit-derived anti-Tctex-1 polyclonal antibody (1:100 dilution in PBS, Santa Cruz Biotechnology, sc-28537) was added, and then cells were incubated at room temperature for 2 hours. Furthermore, an Alexa488 green-fluorescent-dye-conjugated rabbit-derived secondary antibody was added, followed by 1 hour of incubation. To detect distribution in the endoplasmic reticulum, Alexa546 red-fluorescent-dye-conjugated concanavalin A (Molecular Probes) was added to cells, followed by 15 minutes of incubation at room temperature.

Figure 21A:
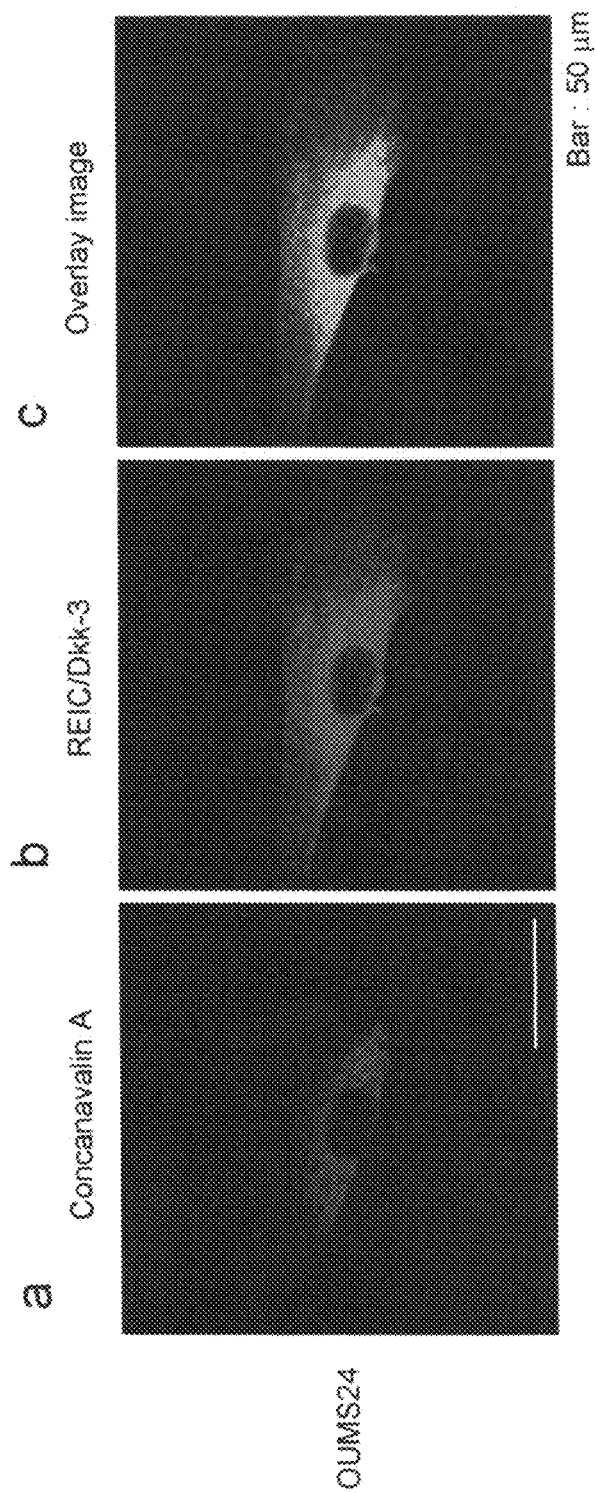
FIG. 21A shows photographs showing intracellular localization of the human full-length REIC/Dkk-3 protein and the Tctex-1 protein. Photographs in FIG. 21A were taken with a confocal microscope after double fluorescent staining (A-c) of the human full-length REIC/Dkk-3 protein (A-b) with concanavalin A (A-a) as an endoplasmic reticulum marker in human OUMS24 fibroblasts.
Figure 21B:
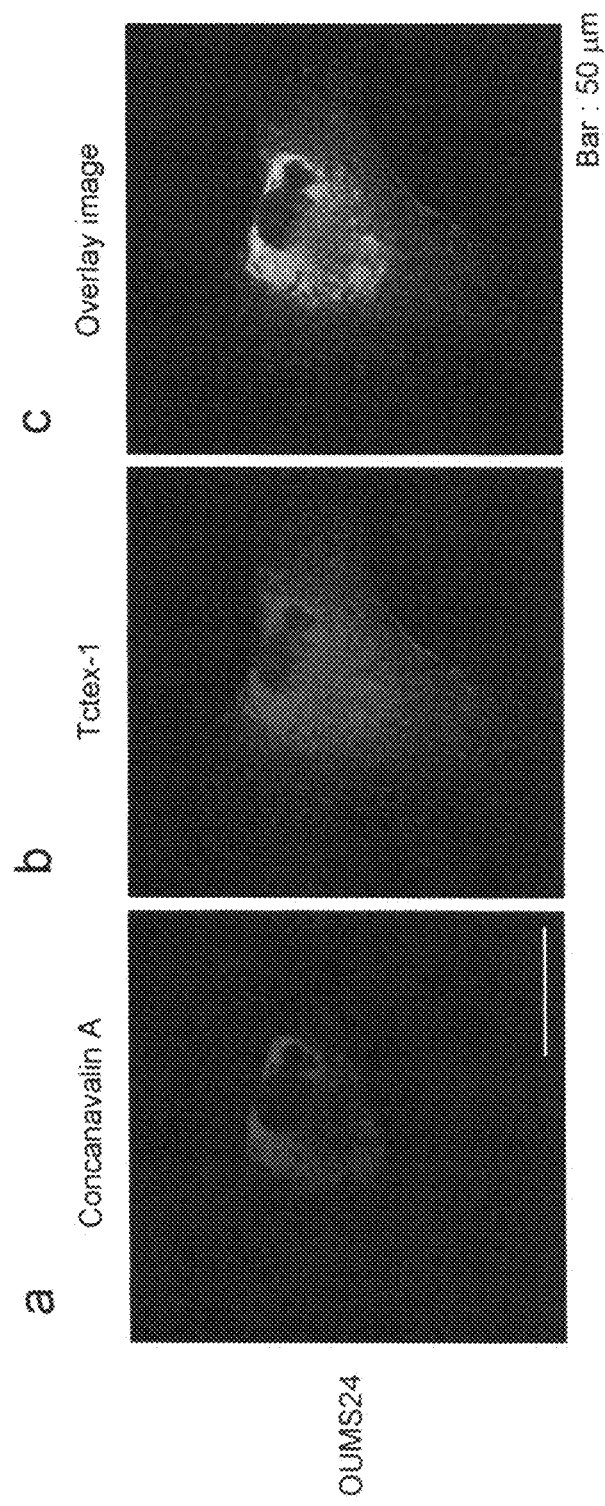
FIG. 21B shows photographs showing intracellular localization of the human full-length REIC/Dkk-3 protein and the Tctex-1 protein. Photographs in FIG. 21B were taken with a confocal microscope after double fluorescent staining (B-c) of the Tctex-1 protein (B-b) with concanavalin A (B-a) as an endoplasmic reticulum marker in human OUMS24 fibroblasts.

In recognition of interaction between REIC/Dkk-3 and Tctex-1 revealed by various assay systems, co-localization of the 2 proteins within cells was analyzed. It has been reported that REIC/Dkk-3 is localized not only in the endoplasmic reticulum, but also in the cytoplasm. Our recent studies have demonstrated that in cells stably expressing the REIC/Dkk-3 protein, the REIC/Dkk-3 protein is localized in the endoplasmic reticulum. Accordingly, to confirm localization of the REIC/Dkk-3 protein and the Tctex-1 protein in the endoplasmic reticulum, an immunofluorescence double staining method was performed using concanavalin A (that is, a fluorescent dye-conjugated endoplasmic reticulum localized marker protein). FIG. 21A shows confocal microscopic images showing the results of double fluorescent staining of the human full-length REIC protein with endoplasmic reticulum marker concanavalin A in OUMS24 human fibroblasts. Red (bright portion in FIG. 21A-a) indicates concanavalin A and green (bright portion in FIG. 21A-b) indicates the full-length REIC protein. The overlay region of the endoplasmic reticulum and the full-length REIC protein is indicated in yellow (bright portion in FIG. 21A-c) (overlay image). FIG. 21B shows confocal microscopic images showing the results of double fluorescent staining of the Tctex-1 protein with endoplasmic reticulum marker concanavalin A in OUMS24 human fibroblasts. Red (bright portion in FIG. 21B-a) indicates concanavalin A and green (bright portion in FIG. 21B-b) indicates the Tctex-1 protein. The overlay region of the endoplasmic reticulum and the Tctex-1 protein is indicated in yellow (bright portion in FIG. 21A-c) (overlay image). As shown in overlay images in FIG. 21A and FIG. 21B, most portions were stained with yellow. Therefore, as expected, REIC/Dkk-3 (FIG. 21A) and Tctex-1 (FIG. 21B) were both localized in the endoplasmic reticulum and the intracellular localization patterns of these proteins in OUMS24 normal fibroblasts were consistent with each other. Specifically, it can be concluded that both REIC/Dkk-3 and Tctex-1 are co-localized around the endoplasmic reticulum and that an interaction partner of REIC/Dkk-3 is Tctex-1.

Example 15

Analysis of the Function of Tctex-1 as a Factor to Accelerate the Capacity of REIC to Induce Apoptosis Adenovirus REIC/Dkk-3 (Ad-REIC) was prepared as follows. A full-length cDNA of REIC/Dkk-3 was inserted into a pAxCAwt cosmid vector and then the vector was introduced into an adenovirus vector by the COS-TPC method (Takara Bio Inc., Shiga, Japan). An adenovirus vector (Ad-LacZ) into which a LacZ gene had been introduced was used as a control.

An apoptosis assay method is as described below. To examine the rate of in vitro apoptosis induction after each treatment, PC3 prostate cancer cells were cultured in flat-bottom 6-well culture plates for 24 hours. The cultured PC3 cells were treated with a GFP-expression plasmid (Clonetech), a Tctex-1-expression plasmid (pcDNA3.2/V5/GW/D-TOPO), or a Tctex-1-sh-RNA plasmid (sc-43319-SH, Santa Cruz Biotechnology) added thereto for 6 hours and then media were exchanged with fresh media. FuGENE HD (Roche) was used for the transfection. The transfection efficiency of the GFP plasmid was 60% or more at 48 hours after addition of the plasmid. At 24 hours after transefction with the GFP expression plasmid, Ad-LacZ and Ad-REIC were added at 50 MOI (multiplicity of infection) in serum free medium for 2 hours of reaction, and then the medium was exchanged with fresh medium. After 48 hours of culture, a 2 µg/ml Hoechst 33342 solution was added to the medium, and then it was left to stand in the dark for 10 minutes. Hoechst 33342 is an intercalating reagent for evaluation of total chromatin content and detection of the degree of chromatin condensation. Highly condensed or fragmented cell nuclei were observed by fluorescence microscopy, and dead cells (apoptotic cells for which apoptosis induction had occurred) were identified. Apoptotic cells were counted by microscopic observation performed for 5 different fields. 100 cells were counted per microscopic image.

Statistical analyses (statistical tests) were conducted as described below. Data are shown as the mean±SE. Student's unpaired t-test was conducted for statistical analyses between the two groups. Differences (between the two) with P values of less than 0.05 were considered to be statistically significant.

Figure 22A:
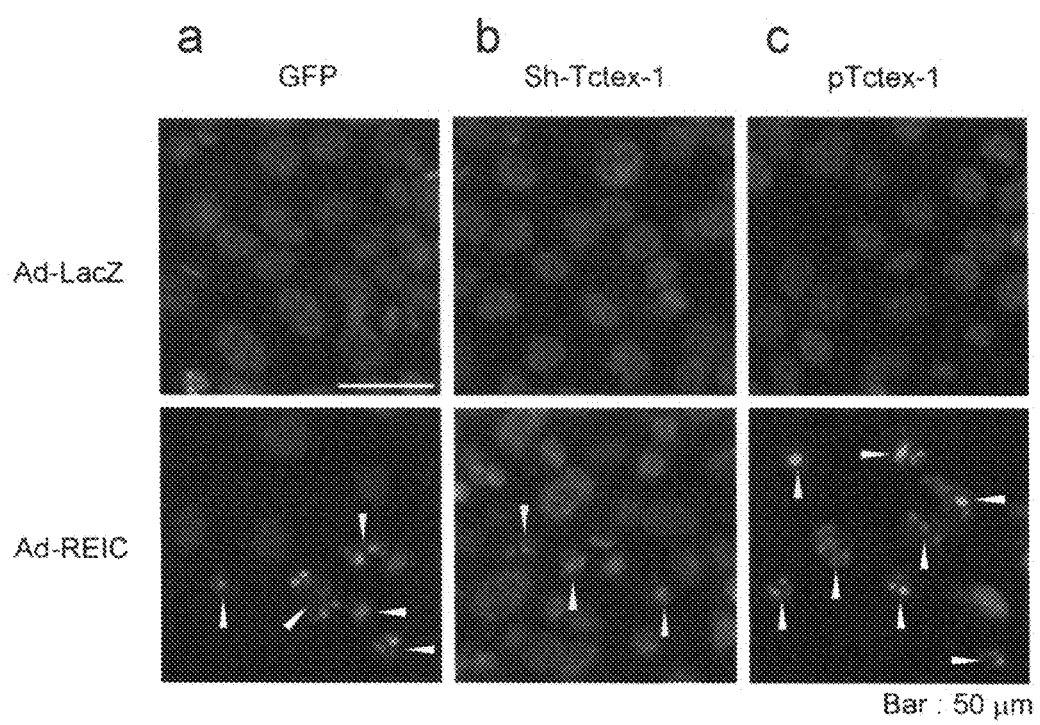
FIG. 22A shows photographs showing images taken by fluorescence microscopy after Hochest staining, which indicate that the capacity of Ad-REIC to induce apoptosis was decreased by a decreased Tctex-1 expression level, but was enhanced by amplified Tctex-1 expression. Photographs on the top show the results of using Ad-LacZ, photographs on the bottom show the results of using Ad-REIC, and "a," "b," and "c" indicate the results of administration of a GFP plasmid, shRNA-Tctex-1, and a Tctex-1 expression plasmid, respectively.
Figure 22B:
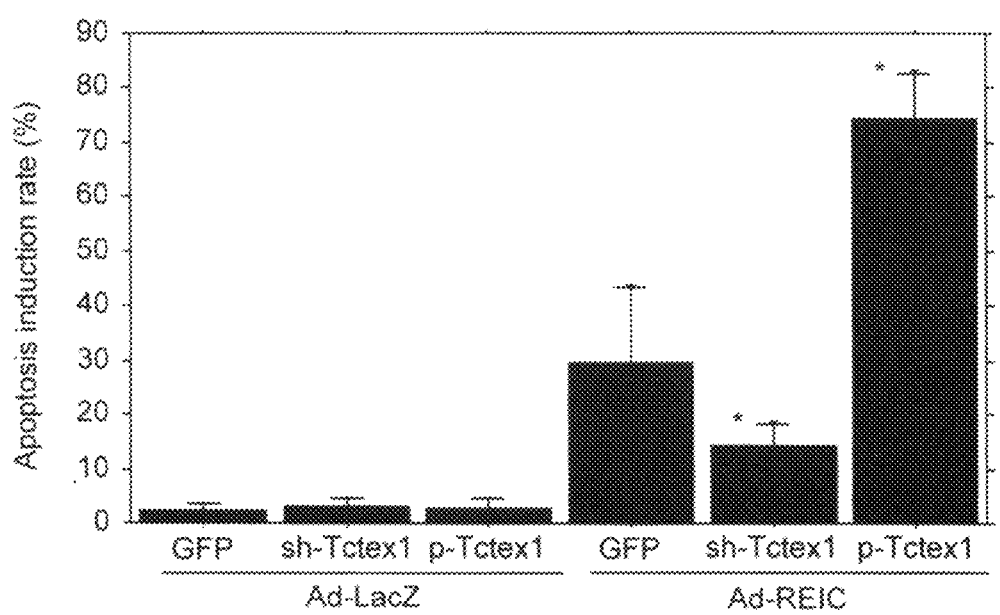
FIG. 22B is a graph showing apoptosis induction rates, indicating that the capacity of Ad-REIC to induce apoptosis was decreased by a decreased Tctex-1 expression level, but was enhanced by amplified Tctex-1 expression.

To examine the functional effects of Tctex-1 on REIC/Dkk-3 apoptotic activity (the capacity to induce apoptosis), a model system (established by the present inventors through their previous studies) of apoptosis induction by REIC/Dkk-3 overexpression using Ad-REIC in PC3 human prostate cancer cells was used. According to the results of Western blot analyses, PC3 expressed endogenous Tctex-1 protein but did not express the REIC/Dkk-3 protein. FIG. 22A shows the results of apoptosis assay using Hoechst 33342. In the results of the assay, apoptosis took place in PC3 to which Ad-REIC had been administered, but apoptosis did not take place in cells treated with Ad-LacZ (indicated with arrows in FIG. 22A). FIG. 22A shows that the capacity of Ad-REIC to induce apoptosis was decreased by a decreased Tctex-1 expression level, but was enhanced by amplified expression thereof. The apoptosis incidences in the groups treated with Ad-REIC were, specifically, 30%, 15%, and 75%, respectively, in the group treated with the GFP plasmid, the group treated with shRNA-Tctex-1, and the group treated with the Tctex-1 expression plasmid (FIG. 22B). Specifically, this suggests that the capacity of Ad- REIC to induce apoptosis is reduced by a decrease in Tctex-1 expression level, but is enhanced by amplified expression. It was revealed that compared with the group treated with the GFP plasmid to which Ad-REIC had been administered, the group treated with shRNA-Tctex-1 exhibited a decreased apoptosis incidence. Meanwhile, it was demonstrated that the Tctex-1 expression plasmid accelerates apoptosis induction. The results suggest that the Tctex-1 expression level is positively correlated with apoptosis induction by REIC/Dkk-3 overexpression using Ad-REIC. Therefore, it can be concluded that Tctex-1 accelerates apoptosis induction by REIC/Dkk-3.

INDUSTRIAL APPLICABILITY

The partial region polypeptide of the REIC/Dkk-3 protein of the present invention has the following effects, compared with IL-2, a cytokine group having many conventionally known immunoactivation effects, and the full-length REIC/Dkk-3 protein.
(1) The partial region polypeptide has anti-tumor effects even in the single-agent form through anticancer immune activation.
(2) Because of the REIC/Dkk-3 protein's own property such that many types of cancer lack REIC/Dkk-3 gene expression or exhibit REIC/Dkk-3 gene expression at low levels, a REIC/Dkk-3 protein preparation is effective for wide-ranging types of cancer.
(3) With anticancer immune activation by the REIC/Dkk-3 protein, effects of improving or preventing cancer not only at cancer lesions to which it is administered, but also cancer metastatic foci, can be expected.
(4) This agent is administered simultaneously with various existing cancer antigen proteins, so that anticancer immunity can be systematically activated via induction of differentiation to dendritic(-like) cells and prevention of carcinogenesis itself becomes possible.

Moreover, the size of the partial region polypeptide of the REIC/Dkk-3 protein of the present invention is small, so that it can be easily produced at low cost.

The REIC/Dkk-3 protein partial region of the present invention can be used as a cancer immunotherapeutic agent and is useful for cancer prevention and treatment.

Sequence Listing Free Text
SEQ ID NO: 11 synthesis
SEQ ID NOS: 12-15 primers
SEQ ID NOS: 16-28 synthesis All publications, patents, and patent applications cited herein are incorporated herein by reference in their entirety.

The invention claimed is:

1. A cDNA consisting of a partial region of a REIC/Dkk-3 cDNA, which consists of the nucleotide sequence shown in SEQ ID NO:8.

2. A vector having a cDNA consisting of a partial region of REIC/Dkk-3 cDNA which consists of the nucleotide sequence shown in SEQ ID NO:8 and includes no other region of REIC/Dkk-3 cDNA than that shown in SEQ ID NO:8 and a heterologous promoter and/or enhancer.

3. An agent for inducing dendritic-cell-like cell differentiation from monocytes, containing a cDNA consisting of a partial region of a REIC/Dkk-3 cDNA, which consists of the nucleotide sequence shown in SEQ ID NO:8 or a vector having a cDNA consisting of a partial region of a REIC/Dkk-3 cDNA, which consists of the nucleotide sequence shown in SEQ ID NO:8, but includes no other region of REIC/Dkk-3 cDNA than that shown in SEQ ID NO:8 and a heterologous promoter and/or enhancer as an active ingredient.

4. An agent for accelerating the induction of differentiation to immunoactivation cells selected from the group consisting of dendritic cells, helper T cells, CTL, and NK cells, containing a cDNA consisting of a partial region of a REIC/Dkk-3 cDNA, which consists of the nucleotide sequence shown in SEQ ID NO:8, or a vector having a cDNA consisting of a partial region of a REIC/Dkk-3 cDNA, which consists of the nucleotide sequence shown in SEQ ID NO:8, but includes no other region of REIC/Dkk-3 cDNA than that shown in SEQ ID NO:8 and a heterologous promoter and/or enhancer as an active ingredient.

5. An agent for inhibiting the induction of differentiation to immunosuppressively functioning cells that are myeloid-derived suppressor cells (MDSC) or immunoregulatory T cells (Treg), containing a cDNA consisting of a partial region of a REIC/Dkk-3 cDNA, which consists of the nucleotide sequence shown in SEQ ID NO:8, or a vector having a cDNA consisting of a partial region of a REIC/Dkk-3 cDNA, which consists of the nucleotide sequence shown in SEQ ID NO:8, but includes no other re ion of REIC/Dkk-3 cDNA than that shown in SE) ID NO:8 and a heterologous promoter and/or enhancer as an active ingredient.

6. An anticancer agent containing a cDNA consisting of a partial region of a REIC/Dkk-3 cDNA, which consists of the nucleotide sequence shown in SEQ ID NO:8 or a vector having a cDNA consisting of a partial region of a REIC/Dkk-3 cDNA, which consists of the nucleotide sequence shown in SEQ ID NO:8, but includes no other region of REIC/Dkk-3 cDNA than that shown in SEQ ID NO:8 and a heterologous promoter and/or enhancer as an active ingredient.

* * * * *